United States Patent
Petsko et al.

(10) Patent No.: US 11,332,504 B2
(45) Date of Patent: *May 17, 2022

(54) METHODS OF REDUCING FUS/TLS- OR TDP-43-MEDIATED NEURONAL CYTOTOXICITY BY UPF1

(71) Applicant: Brandeis University, Waltham, MA (US)

(72) Inventors: Greg Petsko, New York, NY (US); Dagmar Ringe, Cambridge, MA (US); Shulin Ju, Beavercreek, OH (US)

(73) Assignee: Brandeis University, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/739,561

(22) Filed: Jan. 10, 2020

(65) Prior Publication Data

US 2020/0131236 A1 Apr. 30, 2020

Related U.S. Application Data

(63) Continuation of application No. 14/434,737, filed as application No. PCT/US2013/063858 on Oct. 8, 2013, now Pat. No. 10,533,038.

(Continued)

(51) Int. Cl.

| *A61K 38/00* | (2006.01) |
| --- | --- |
| *A61K 49/00* | (2006.01) |
| *C07K 14/00* | (2006.01) |
| *C07K 14/48* | (2006.01) |
| *C12N 15/00* | (2006.01) |
| *C12N 15/09* | (2006.01) |
| *C12N 15/12* | (2006.01) |
| *C12N 15/13* | (2006.01) |
| *C12N 15/11* | (2006.01) |
| *C07K 14/47* | (2006.01) |
| *A61K 38/17* | (2006.01) |
| *G01N 33/50* | (2006.01) |
| *A61K 9/00* | (2006.01) |
| *C12Q 1/02* | (2006.01) |
| *A61K 31/7125* | (2006.01) |
| *A61K 48/00* | (2006.01) |
| *A61K 31/7088* | (2006.01) |
| *A61K 31/711* | (2006.01) |
| *A61K 31/7105* | (2006.01) |
| *A61K 31/7115* | (2006.01) |
| *C12Q 1/6883* | (2018.01) |
| *A61K 35/12* | (2015.01) |
| *C12N 15/85* | (2006.01) |

(Continued)

(52) U.S. Cl.

CPC ............ *C07K 14/47* (2013.01); *A61K 9/0019* (2013.01); *A61K 38/17* (2013.01); *C12Q 1/025* (2013.01); *G01N 33/5058* (2013.01); *A01K 67/0275* (2013.01); *A01K 2207/05* (2013.01); *A01K 2207/10* (2013.01); *A01K 2207/20* (2013.01); *A01K 2217/206* (2013.01); *A01K 2267/03* (2013.01); *A01K 2267/0306* (2013.01); *A01K 2267/0318* (2013.01); *A01K 2267/0393* (2013.01); *A61K 31/7088* (2013.01); *A61K 31/711* (2013.01); *A61K 31/7105* (2013.01); *A61K 31/7115* (2013.01); *A61K 31/7125* (2013.01); *A61K 35/12* (2013.01); *A61K 38/00* (2013.01); *A61K 38/1709* (2013.01); *A61K 48/00* (2013.01); *A61K 48/005* (2013.01); *A61K 48/0066* (2013.01); *A61K 2300/00* (2013.01); *A61P 3/00* (2018.01); *C12N 15/85* (2013.01); *C12Q 1/6883* (2013.01); *C12Q 2600/106* (2013.01); *G01N 33/5023* (2013.01); *G01N 2333/47* (2013.01); *G01N 2500/10* (2013.01); *G01N 2800/56* (2013.01)

(58) Field of Classification Search

CPC ............ A61K 2300/00; A61K 31/7105; A61K 31/713; A61K 31/00; A61K 38/00; A61K 48/005; A61K 38/17; A61K 48/00; A61K 9/0019; A61K 31/711; C12Q 1/6883; C12Q 2600/158; C12Q 2600/118; C12Q 2600/106; C12Q 2600/112; C07K 14/47; C07K 14/435; G01N 33/6896; G01N 2500/10; G01N 33/5058; G01N 2800/2835; C12N 15/85; G06F 19/01; G06F 19/18; A01K 2267/0318

See application file for complete search history.

(56) References Cited

U.S. PATENT DOCUMENTS 8,486,635 B2 7/2013 Hutton et al.
8,603,814 B2 12/2013 Pe'ery et al.

(Continued)

FOREIGN PATENT DOCUMENTS

WO WO-98/45322 A2 10/1998
WO WO-2014/058866 A2 4/2014

OTHER PUBLICATIONS

Ward et al. Cell Death and Disease; 2014; 5:e1572; doi:10.1038/cddis.2014.508.*

(Continued)

*Primary Examiner* — Chang-Yu Wang
(74) *Attorney, Agent, or Firm* — Choate, Hall & Stewart LLP; John P. Rearick; Nicholas J. Pace

(57) ABSTRACT

Nonsense-mediated mRNA decay (NMD) polypeptides, nucleic acids encoding NMD polypeptides, and methods of using such polypeptides and nucleic acids in the treatment of ALS and in screening for agents for the treatment of ALS are described.

7 Claims, 1 Drawing Sheet

Specification includes a Sequence Listing.

Related U.S. Application Data

(60) Provisional application No. 61/712,322, filed on Oct. 11, 2012.

(51) Int. Cl.
*A61P 3/00* (2006.01)
*A01K 67/027* (2006.01)

(56) References Cited

U.S. PATENT DOCUMENTS

| | | | |
|---|---|---|---|
| 9,271,998 | B2 | 3/2016 | Pe'ery et al. |
| 10,533,038 | B2 | 1/2020 | Petsko et al. |
| 2003/0032158 | A1 | 2/2003 | Peltz et al. |
| 2004/0127577 | A1 | 7/2004 | Blaugrund et al. |
| 2010/0105034 | A1 | 4/2010 | Hutton et al. |
| 2011/0039911 | A1 | 2/2011 | Pe'ery et al. |
| 2013/0345142 | A1 | 12/2013 | Hutton et al. |
| 2014/0073685 | A1 | 3/2014 | Pe'ery et al. |
| 2014/0206637 | A1 | 7/2014 | Pe'ery et al. |
| 2015/0259391 | A1 | 9/2015 | Petsko et al. |

OTHER PUBLICATIONS

Sama et al. ASN Neuro. 2014;1-18. doi:10.1177/17509141454472.*
Budini et al.,J. Mol. Neurosci. 2011; 45:473-479.*
Polymenidou et al., Nat Neurosci. 2011;14:459-468.*
Jackson et al. Gene therapy, 2015; 20:20-28.*
Park et al. Nat. Commun.2020; 11:3106. doi.org/10.1038/s41467-020-16939-6.*
Alaoui-Ismaili, M.H. and Falb, D., Design of second generation therapeutic recombinant bone morphogenetic proteins, Cytokine Growth Factor Rev., 20(5-6): 501-7 (2009).
Author Not Known, ALZFORUM: Networking for a Cure, DC: ALS Treatment Possibilities Presented at SfN, Satellite, 9 pages (Nov. 30, 2011).
Barmada, S. J. et al, Amelioration of toxicity in neuronal models of amyotrophic lateral sclerosis by hUPF1, PNAS, 112(25): 7821-7826 (2015).
Bruijn, L.I. et al., Unraveling the Mechanisms Involved in Motor Neuron Degeneration in ALS, Annu. Rev. Neurosci., 27: 723-749 (2004).
Burgess, W. H. et al, Possible dissociation of the heparin-binding and mitogenic activities of heparin-binding (acidic fibroblast) growth factor-1 from its receptor-binding activities by site-directed mutagenesis of a single lysine residue, J. Cell Biol., 111(5 Pt 1): 2129-38 (1990).
Chen, Y. et al., DNA/RNA helicase gene mutations in a form of juvenile amyotrophic lateral sclerosis (ALS4), American Journal of Human Genetics, 74(6):1128-1135 (2004).
Guo, H.H. et al, Protein tolerance to random amino acid change, PNAS, 101(25): 9205-10 (2004).
Ilieva, H. et al., Non-cell autonomous toxicity in neurodegenerative disorders: ALS and beyond, The Journal of Cell Biology, 187(6):761-772 (2009).
International Search Report for PCT/US2013/063858, 4 pages (dated Aug. 19, 2014).
Jackson, K.L. et al, Preservation of forelimb function by UPF1 gene therapy in a rat model of TDP-43-induced motored paralysis, Gene Ther., 22(!): 20-28 (2015).
Ju, et al., A Yeast Model of FUS/TLS-Dependent Cytotoxicity, PLoS Biol, 9(4): e1001052, pp. 1-17 (2011).
Kryndushkin, D. and Shewmaker, F., Modeling ALS and FTLD proteinopathies in yeast, An efficient approach for studying protein aggregation and toxicity, Prion, 5(4): 250-257 (2011).
Kwiatkowski, T.J. et al., Mutations in the FUS/TLS gene on chromosome 16 cause familial amyotrophic lateral sclerosis, Science, 323(5918):1205-1208 (2009).

Lagier-Tourenne, C. et al., TDP-43 and FUS/TLS: emerging roles in RNA processing and neurodegeneration, Hum. Mol. Genet., 19: R46-R64 (2010).
Lagier-Tourenne, C. and Cleveland, D.W., Rethinking ALS: the FUS about TDP-43, Cell, 136(6): 1001-1004, 8 pages (2009).
Maquat, L.E. and Carmichael, G.G., Quality control of mRNA function, Cell, 104(2):173-176 (2001).
Maquat, L.E., Nonsense-mediated mRNA decay in mammals, Journal of Cell Science, 118(9):1773-1776 (2005).
Maruyama, H. et al., Mutations of optineurin in amyotrophic lateral sclerosis, Nature, 465(7295):223-226 (2010).
Nicholson, P. and Mühlemann, O., Cutting the nonsense: the degradation of PTC-containing mRNAs, Biochemical Society Transactions, 38(6):1615-1620 (2010).
Nishimura, A.L. et al., A mutation in the vesicle-trafficking protein VAPB causes late-onset spinal muscular atrophy and amyotrophic lateral sclerosis, American Journal of Human Genetics, 75(5):822-831 (2004).
Pawson, T. and Nash, P., Assembly of cell regulatory systems through protein interaction domains, Science, 300(5618): 445-52 (2003).
Rehwinkel, J. et al., Nonsense-mediated mRNA decay factors act in concert to regulate common mRNA targets, RNA, 11(10):1530-1544 (2005).
Rehwinkel, J. et al., Nonsense-mediated mRNA decay: Target genes and functional diversification of effectors, Trends Biochemical Science, 31(11):639-646 (2006).
Rosen, D.R. et al., Mutations in Cu/Zn superoxide dismutase gene are associated with familial amyotrophic lateral sclerosis, Nature, 362(6415):59-62 (1993).
Rothstein, J.D. et al., Current hypotheses for the underlying biology of amyotrophic lateral sclerosis, Annals of Neurology, 65(1):S3-S9 (2009).
Rothstein, J.D., Therapeutic horizons for amyotrophic lateral sclerosis, Curr. Opin. in Neurobiol., 6: 679-687 (1996).
Sreedharan, J. et al., TDP-43 mutations in familial and sporadic amyotrophic lateral sclerosis, Science, 319(5870):1668-1672 (2008).
Takahashi, K. and Yamanaka, K., Induction of pluripotent stem cells from mouse embryonic and adult fibroblast cultures by defined factors, Cell, 126(4):663-676 (2006).
Vaccaro, A. et al., Mutant TDP-43 and FUS Cause Age-Dependent Paralysis and Neurodegeneration in C. elegans, PLoS ONE, 7(2): e31321 1-10 (2012).
Vance, C. et al., Mutations in FUS, an RNA processing protein, cause familial amyotrophic lateral sclerosis type 6, Science, 323(5918):1208-1211 (2009).
Wittkopp, N. et al., Nonsense-mediated mRNA decay effectors are essential for zebrafish embryonic development and survival, Molecular and Cellular Biology, 29(13):3517-3528 (2009).
Written Opinion for PCT/US2013/063858, 7 pages (dated Aug. 19, 2014).
Hergesheimer, R. C. et al., The debated toxic role of aggregated TDP-43 in amyotrophic lateral sclerosis: a resolution in sight?, Brain, 142:1176-1194 (2019).
Ortega, J. A. et al., Nucleocytoplasmic Proteomic Analysis Uncovers eRF1 and Nonsense-Mediated Decay as Modifiers of ALS/FTD C9orf72 Toxicity, Neuron, 106:90-107 (2020).
Scotter, E. L. et al., TDP-43 Proteinopathy and ALS: Insights into Disease Mechanisms and Therapeutic Targets, Neurotherapeutics, 12:352-363 (2015).
Kervestin, S. and Jacobson, A., NMD: a multifaceted response to premature translation termination, Nature, 13:700-712 (2012).
Neumann, M., Molecular Neuropathology of TDP-43 Proteinopathies, International Journal of Molecular Sciences, 10:232-246 (2009).

* cited by examiner

METHODS OF REDUCING FUS/TLS- OR TDP-43-MEDIATED NEURONAL CYTOTOXICITY BY UPF1

CROSS REFERENCE TO RELATED APPLICATIONS

The present application is a continuation of U.S. application Ser. No. 14/434,737 (now U.S. Pat. No. 10,533,038), filed Apr. 9, 2015, which is a national phase application under 35 U.S.C. § 371 of PCT International Application No. PCT/US2013/063858, filed Oct. 8, 2013, which claims the benefit of U.S. provision application Ser. No. 61/712,322, filed Oct. 11, 2012, the contents of each of which are herein incorporated by reference in their entirety.

BACKGROUND

Amyotrophic lateral sclerosis (ALS, also called Lou Gehrig's disease) is a relentlessly progressive, fatal neurodegenerative disease with a prevalence of about 5 people out of 100,000 each year and an average age of onset of about 60 years. Patients with ALS suffer from degeneration of motor neurons in the brain and spinal cord, which leads to progressive muscular weakness. ALS accounts for about 1/300 to 1/400 of all deaths, which means that about 1,000,000 people now alive in the United States will develop ALS. Death typically occurs 3-5 years after disease onset, due to respiratory paralysis. There is no effective treatment for the disease; the only approved ALS drug (riluzole) extends the lifespan of some ALS patients by only about 3 months. Thus, there remains a need for new therapeutic approaches for treatment of ALS.

SUMMARY

The present disclosure encompasses the surprising discovery that agents involved in nonsense-mediated mRNA decay (NMD) can protect neuronal cells from damage associated with TDP-43 or FUS/TLS. The present invention therefore provides NMD agents for use in medicine, and specifically in treatment or prevention (e.g., delay of onset) of certain neurological disorders including specifically amyotrophic lateral sclerosis (ALS). For example, in various aspects, the present disclosure provides methods of reducing FUS/TLS or TDP-43 toxicity in a neuronal cell or glial cell suffering from or susceptible to such toxicity, comprising providing to the cell (e.g., in vitro or in vivo) a therapeutically effective amount of an NMD polypeptide, thereby reducing the FUS/TLS or TDP-43 toxicity in the cell. In some embodiments, the step of providing comprises administering a composition comprising the NMD polypeptide, a nucleic acid encoding the NMD polypeptide, and/or an activator of the NMD polypeptide. In some embodiments, the NMD polypeptide is a UPF1, UPF2, UPF3, SMG1, SMG5, SMG6, or SMG7 polypeptide. In some embodiments, the cell is a human neuronal cell or a human glial cell.

In various aspects, the present disclosure provides methods of treating a disease, disorder or condition associated with FUS/TLS or TDP-43 toxicity, comprising administering to a subject suffering from or susceptible to the disease, disorder or condition a therapeutically effective amount of an NMD polypeptide, a nucleic acid encoding an NMD polypeptide, and/or an activator or an NMD polypeptide, thereby treating the disease, disorder or condition. In some embodiments, the therapeutically effective amount is correlated with a statistically significant probability of reducing FUS/TLS or TDP-43 toxicity in a neuronal cell or a glial cell. In some embodiments, the therapeutically effective amount is correlated with a statistically significant probability of enhancing mRNA processing in a neuronal cell or a glial cell. In some embodiments, the disease, disorder or condition is not associated with SOD1 toxicity. In some embodiments, the NMD polypeptide, nucleic acid encoding the NMD polypeptide, and/or the activator of the NMD polypeptide is administered into the CNS of the subject, such as by intrathecal injection.

In various aspects, the present disclosure provides methods of treating ALS in a human subject, comprising: administering to a subject suffering from or susceptible to ALS a therapeutically effective amount of an NMD polypeptide, thereby treating the ALS in the subject. In some embodiments, the therapeutically effective amount is correlated with a statistically significant probability of reducing toxicity in a human neuronal cell or a human glial cell. In some embodiments, the toxicity is FUS/TLS or TDP-43 toxicity. In some embodiments, the toxicity is not SOD1 toxicity. In some embodiments, the therapeutically effective amount is correlated with a statistically significant probability of enhancing mRNA processing in a human neuronal cell or a human glial cell.

In various aspects, the present disclosure provides methods of identifying an agent useful in the treatment of ALS, comprising: contacting a population of neuronal cells or glial cells that are suffering from or susceptible to FUS/TLS or TDP-43 toxicity with a test agent; determining a number of viable cells in the population after the contacting step; and comparing the number of viable cells to a control; wherein a test agent that increases the number of viable cells relative to the control is identified as an agent useful in the treatment of ALS. In some embodiments, the neuronal cells or the glial cells are transfected with a nucleic acid encoding FUS/TLS or TDP-43.

In various aspects, the present disclosure provides methods of identifying an agent useful in the treatment of ALS, comprising: contacting a population of neuronal cells or glial cells that are suffering from or susceptible to FUS/TLS or TDP-43 toxicity with a test agent; determining a level of mRNA processing in the population of neuronal cells or glial cells after the contacting step; and comparing the level of mRNA processing to a control; wherein a test agent that increases the level of mRNA processing relative to the control is identified as an agent useful in the treatment of ALS.

In various aspects, the present disclosure provides methods of identifying an agent useful in the treatment of ALS, comprising: contacting a first population of neuronal cells or glial cells that are suffering from or susceptible to FLS/TLS or TDP-43 toxicity with a test agent; determining a first number of viable cells in the first population after the contacting step; administering an NMD polypeptide to a second population of neuronal cells or glial cells that are suffering from or susceptible to FUS/TLS or TDP-43 toxicity; and determining a second number of viable cells in the second population after the administration step; wherein a first number of viable cells that is comparable to the second number of viable cells indicates the test agent is an agent useful in the treatment of ALS.

In various aspect, the present disclosure provides pharmaceutical compositions for treating ALS comprising an NMD polypeptide, a nucleic acid encoding an NMD polypeptide, or an activator of an NMD polypeptide, and a pharmaceutically acceptable excipient. In some embodiments, the pharmaceutical composition further comprising a targeting agent. In some embodiments, upon administration to a subject, the targeting agent selectively targets the composition to the brain.

In various aspect, the present disclosure provides methods of treating ALS in a human subject suffering from or susceptible to ALS, comprising: administering to the human subject a therapeutically effective amount of a UPF1 polypeptide, wherein the therapeutically effective amount is correlated with a statistically significant probability of reducing toxicity in a human neuronal cell or a human glial cell, thereby treating the ALS. In some embodiments, the subject has a mutation in an ALS2 gene, a VAPB gene, a SETX gene, a TDP-43 gene, a FUS/TLS gene, or an OPTN gene. In some embodiments, the subject does not have a mutation in a SOD1 gene.

BRIEF DESCRIPTION OF THE DRAWINGS

The following figures are presented for the purpose of illustration only, and are not intended to be limiting.

Figure 1A:
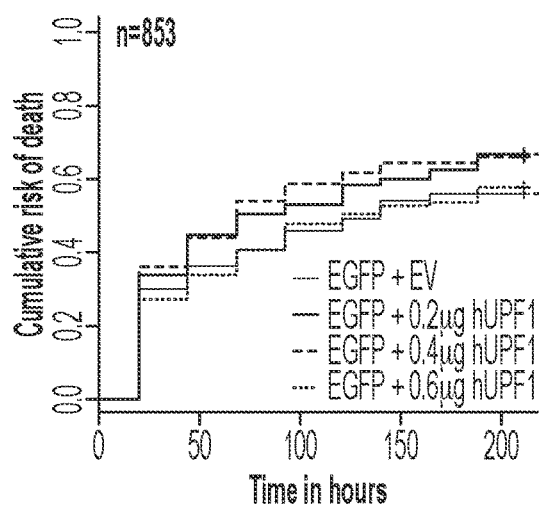
FIG. 1A is a graphical representation of cell death of neurons following expression of UPF1.

All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Other features and advantages of the invention will be apparent from the following detailed description, and from the claims.

Definitions

In order for the present invention to be more readily understood, certain terms are first defined below. Additional definitions for the following terms and other terms its are set forth throughout the specification.

Approximately or about: As used herein, the term in "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" means the prevention, reduction or palliation of a state, or improvement of the state of a subject. Amelioration includes, but does not require, complete recovery or complete prevention of a disease condition.

Characteristic portion: As used herein, the term a "characteristic portion" of a substance, in the broadest sense, is one that shares some degree of sequence or structural identity with respect to the whole substance. In certain embodiments, a characteristic portion shares at least one functional characteristic with the intact substance. For example, in some embodiments, a "characteristic portion" of a polypeptide or protein is one that contains a continuous stretch of amino acids, or a collection of continuous stretches of amino acids, that together are characteristic of a polypeptide or protein. In some embodiments, each such continuous stretch generally contains at least 2, 5, 10, 15, 20, 50, or more amino acids. In some embodiments, such a continuous stretch includes certain residues whose position and identity are fixed; certain residues whose identity tolerates some variability (i.e., one of a few specified residues is accepted); and optionally certain residues whose identity is variable (i.e., any residue is accepted). In general, a characteristic portion of a substance (e.g., of a polypeptide or protein) is one that, in addition to the sequence and/or structural identity specified above, shares at least one functional characteristic with the relevant intact substance. In some embodiments, a characteristic portion may be biologically active.

Characteristic sequence: A "characteristic sequence" is a sequence that is found in all members of a family of polypeptides or nucleic acids, and therefore can be used by those of ordinary skill in the art to define members of the family.

Combination therapy: The term "combination therapy", as used herein, refers to those situations in which two or more different pharmaceutical agents are administered in overlapping regimens so that the subject is simultaneously exposed to both agents. When used in combination therapy, two or more different agents may be administered simultaneously or separately. This administration in combination can include simultaneous administration of the two or more agents in the same dosage form, simultaneous administration in separate dosage forms, and separate administration. That is, two or more agents can be formulated together in the same dosage form and administered simultaneously. Alternatively, two or more agents can be simultaneously administered, wherein the agents are present in separate formulations. In another alternative, a first agent can be administered just followed by one or more additional agents. In the separate administration protocol, two or more agents may be administered a few minutes apart, or a few hours apart, or a few days apart.

Comparable: The term "comparable", as used herein, refers to a system, set of conditions, effects, or results that is/are sufficiently similar to a test system, set of conditions, effects, or results, to permit scientifically legitimate comparison. Those of ordinary skill in the art will appreciate and understand which systems, sets of conditions, effects, or results are sufficiently similar to be "comparable" to any particular test system, set of conditions, effects, or results as described herein.

Correlates: The term "correlates", as used herein, has its ordinary meaning of "showing a correlation with". Those of ordinary skill in the art will appreciate that two features, items or values show a correlation with one another if they show a tendency to appear and/or to vary, together. In some embodiments, a correlation is statistically significant when its p-value is less than 0.05; in some embodiments, a correlation is statistically significant when its p-value is less than 0.01. In some embodiments, correlation is assessed by regression analysis. In some embodiments, a correlation is a correlation coefficient.

Homology: As used herein, the term "homology" refers to the overall relatedness between polymeric molecules, e.g., between nucleic acid molecules (e.g., DNA molecules and/ or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90% 95% or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Improve, increase, or reduce: As used herein, the terms "improve," "increase" or "reduce," or grammatical equivalents, indicate values that are relative to a reference (e.g., baseline) measurement, such as a measurement taken under comparable conditions (e.g., in the same individual prior to initiation of treatment described herein, or a measurement in a control individual (or multiple control individuals) in the absence of treatment) described herein.

NMD agent: As used herein, the term "NMD agent" refers to an NMD polypeptide, a nucleic acid that encodes an NMD polypeptide, or an agent that increases NMD polypeptide level and/or activity. In some embodiments, an NMD agent is a therapeutic agent.

NMD polypeptide: As used herein, the term "NMD polypeptide" refers to a polypeptide whose amino acid sequence includes at least one characteristic sequence of and/or shows at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71% or 70% identity with a protein involved in nonsense-mediated mRNA decay (e.g., UPF1, UPF2, UPF3, SMG1, SMG5, SMG6, or SMG7). A wide variety of NMD sequences from flies, vertebrates, and mammals are known in the art, such as those described herein; in some embodiments, an NMD polypeptide shares at least one characteristic sequence of and/or shows the specified degree of overall sequence identity with one of the UPF1, UPF2, UPF3, SMG1, SMG5, SMG6, or SMG7 set forth herein (each of which may be considered a "reference" NMD polypeptide). In some embodiments, an NMD polypeptide as described herein shares at least one biological activity with a reference NMD polypeptide as set forth herein. In some such embodiment, the shared biological activity relates to nonsense-mediated mRNA decay.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids.

Providing: As used herein, the term "providing" refers to performing a manipulation that causes an entity of interest to be present at a level and/or with an activity higher than that observed under otherwise comparable conditions prior to or absent the manipulation. In some embodiments, providing consists of or comprises administering the entity itself (alone or as part of a composition); in some embodiment, providing consists of or comprises administering an agent that causes an increase in level and/or activity of the entity of interest. For example, where the entity of interest is or comprises a polypeptide, in some embodiments, "providing" the polypeptide consists of or comprises administering the polypeptide (e.g., to a cell, whether isolated or in an organism); in some embodiments, "providing" the polypeptide consists of or comprises administering a nucleic acid encoding the polypeptide; in some embodiments, "providing" the polypeptide consists of or comprises administering an agent that results in increased expression of an endogenous copy of the polypeptide (e.g., by stimulating one or more of transcription, RNA processing, translation, etc. and/or by inhibiting an inhibitor of one of these).

Reference: A "reference" entity, system, amount, set of conditions, etc., is one against which a test entity, system, amount, set of conditions, etc. is compared as described herein. For example, in some embodiments, a "reference"

individual is a control individual who is not suffering from or susceptible to any form of ALS disease; in some embodiments, a "reference" individual is a control individual afflicted with the same form of ALS disease as an individual being treated, and optionally who is about the same age as the individual being treated (to ensure that the stages of the disease in the treated individual and the control individual(s) are comparable).

Subject: As used herein, the term "subject", "individual", or "patient" refers to any organism upon which embodiments of the invention may be used or administered, e.g., for experimental, diagnostic, prophylactic, and/or therapeutic purposes. Typical subjects include animals (e.g., mammals such as mice, rats, rabbits, non-human primates, and humans; insects; worms; etc.).

Target cell or target tissue: As used herein, the terms "target cell" or "target tissue" refers to any cell, tissue, or organism that is affected by ALS to be treated, or any cell, tissue, or organism in which a protein involved in ALS is expressed. In some embodiments, target cells, target tissues, or target organisms include those cells, tissues, or organisms in which there is a detectable or abnormally high amount of FUS or TDP-43 (e.g., comparable to that observed in patients suffering from or susceptible to ALS). In some embodiments, target cells, target tissues, or target organisms include those cells, tissues, or organisms that display a disease-associated pathology, symptom, or feature.

Therapeutic agent: As used herein, the phrase "therapeutic agent" refers to any agent that, when administered to a subject, has a therapeutic effect and/or elicits a desired biological and/or pharmacological effect.

Therapeutic regimen: As used herein, the term "therapeutic regimen" refers to any method used to partially or completely alleviate, ameliorate, relieve, inhibit, prevent, delay onset of, reduce severity of and/or reduce incidence of one or more symptoms or features of a particular disease, disorder, and/or condition. It may include administration of one or more doses, optionally spaced apart by regular or varied time intervals. In some embodiments, a therapeutic regimen is one whose performance is designed to achieve and/or is correlated with achievement of (e.g., across a relevant population of cells, tissues, or organisms) a particular effect, e.g., reduction or elimination of a detrimental condition or disease such as ALS. In some embodiments, treatment includes administration of one or more therapeutic agents either simultaneously, sequentially or at different times, for the same or different amounts of time. In some embodiments, a "treatment regimen" includes genetic methods such as gene therapy, gene ablation or other methods known to induce or reduce expression (e.g., transcription, processing, and/or translation of a particular gene product, such as a primary transcript or mRNA).

Therapeutically effective amount: As used herein, the term "therapeutically effective amount" refers to an amount of a therapeutic agent (e.g., an NMD polypeptide) which confers a therapeutic effect on the treated subject, at a reasonable benefit/risk ratio applicable to any medical treatment. Such a therapeutic effect may be objective (i.e., measurable by some test or marker) or subjective (i.e., subject gives an indication of or feels an effect). In some embodiments, "therapeutically effective amount" refers to an amount of a therapeutic agent or composition effective to treat, ameliorate, or prevent (e.g., delay onset of) a relevant disease or condition, and/or to exhibit a detectable therapeutic or preventative effect, such as by ameliorating symptoms associated with the disease, preventing or delaying onset of the disease, and/or also lessening severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, or on combination with other therapeutic agents. Alternatively or additionally, a specific therapeutically effective amount (and/or unit dose) for any particular patient may depend upon a variety of factors including the particular form of ALS being treated; the severity of the ALS; the activity of the specific therapeutic agent employed; the specific composition employed; the age, body weight, general health, sex and diet of the patient; the time of administration, route of administration, and/or rate of excretion or metabolism of the specific therapeutic agent employed; the duration of the treatment; and like factors as is well known in the medical arts.

Treatment: As used herein, the term "treatment" (also "treat" or "treating") refers to any administration of a therapeutic agent (e.g., an NMD polypeptide) according to a therapeutic regimen that achieves a desired effect in that it partially or completely alleviates, ameliorates, relieves, inhibits, delays onset of, reduces severity of and/or reduces incidence of one or more symptoms or features of a particular disease, disorder, and/or condition (e.g., ALS); in some embodiments, administration of the therapeutic agent according to the therapeutic regimen is correlated with achievement of the desired effect. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION

The present disclosure encompasses the surprising discovery that UPF1 can prevent neuronal toxicity due to TDP-43 or FUS/TLS. UPF1 is a protein involved in nonsense-mediated mRNA decay (NMD). Accordingly, the disclosure provides, among other things, various therapeutic modalities, including use of NMD polypeptides (e.g., UPF1, UPF2, UPF3, SMG1, SMG5, SMG6, or SMG7) to treat amyotrophic lateral sclerosis (ALS).

Amyotrophic Lateral Sclerosis (ALS)

ALS, which exists as both inherited and random forms, is characterized by degeneration of spinal motor neurons, leading to paralysis and death. While most forms of ALS are sporadic and idiopathic (sALS), about 10% of cases are inherited in a Mendelian fashion and are designated familial ALS (fALS). The present invention provides compositions and methods useful in treating ALS.

Using genetic analysis, several genes that cause fALS have been identified. The first mutations were identified in SOD1, which encodes the ubiquitously expressed copper/zinc superoxide dismutase. These variants are involved in about 20% of fALS cases worldwide (Rosen et al., Nature 362:59-62 (1993)). Other genes involved in fALS include genes coding for alsin (ALS2), vesicle associated membrane protein B (VAPB) (Nishimura et al., Am. J. Hum. Genet. 75:822-831 (2004)), senataxin (SETX) (Chen et al., Am. J. Hum. Genet. 74:1128-1135 (2004)), TAR-DNA-binding protein (TDP-43) (Sreedharan et al., Science 319:1668-1672 (2008)), fused in sarcoma or translocated in liposarcoma (FUS/TLS) (Kwiatkowski et al., Science 323:1205-1208 (2009); Vance et al., Science 323:1208-1211 (2009)), and optineurin (OPTN) (Maruyama et al., Nature 465:223-226 (2010)). FUS/TLS is a nucleic acid binding protein that, when mutated, can cause a subset of fALS and can also increase risk for the sporadic disease. Although FUS/TLS is normally located predominantly in the nucleus, pathogenic mutant forms of FUS/TLS traffic to, and form inclusions in, the cytoplasm of affected spinal motor neurons or glia.

Studies of these genes have provided insight into the biochemical processes that may underlie ALS. Putative mechanisms of toxicity targeting motor neurons include glutamate excitotoxicity, oxidative damage, proteasome inhibition, mitochondrial dysfunction, ER stress, axonal transport defects, growth factor signaling deficiency, and glial cell dysfunction (Rothstein et al., Ann. Neurol. 65:S3-S9 (2009); Ilieva et al., J. Cell Biol. 187:761-772 (2009)).

Nonsense-Mediated mRNA Decay

In mammalian cells, expression of protein-encoding genes requires a series of steps in which pre-mRNA is processed to mRNA in the nucleus before mRNA is translated into protein in the cytoplasm. These steps are subject to quality control to ensure that only completely processed mRNA is exported to the cytoplasm (see, e.g., Maquat et al., Cell 104:173-176 (2001)). One form of quality control, called mRNA surveillance or nonsense-mediated mRNA decay (NMD), degrades mRNAs that prematurely terminate translation more than 50-55 nucleotides upstream of an exon-exon junction as a means to prevent the synthesis of potentially harmful truncated proteins (see, e.g., Maquat, J. Cell Sci. 118:1773-1776 (2005); Nicholson et al., Biochem. Soc. Trans. 38:1615-20 (2010)). A number of proteins are involved in NMD in mammalian cells, including UPF1, UPF2, UPF3, SMG1, SMG5, SMG6, and SMG7 (Wittkopp et al., Mol. Cell. Biol. 29:3517-3528 (2009); Rehwinkel et al, Trends Biochem. Sci. 31:639-646 (2006); Rehwinkel et al., RNA 11:1530-1544 (2005)). According to the present disclosure, any NMD polypeptides can be used to treat ALS in methods described herein.

Nucleic Acid Sequences Encoding NMD Polypeptides

Methods and compositions described herein include, for example, nucleic acids encoding NMD polypeptides (e.g., UPF1, UPF2, UPF3, SMG1, SMG5, SMG6, or SMG7). According to the present disclosure, such nucleic acids (and polypeptides) are useful in the treatment of ALS. In some embodiments, such nucleic acids have or include nucleotide sequences as set forth in SEQ ID NO:1, 3, 5, 7, 9, 11, or 13, or characteristic sequence elements thereof or therein. In some embodiments, useful nucleic acids show at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% overall sequence identity with one or more of SEQ ID NO:1, 3, 5, 7, 9, 11, or 13. Alternatively or additionally, in some embodiments, useful nucleic acids include at least 5, 6, 7, 8, 9, 10, 11, 12, 13, 14, 15, 16, 17, 18, 19, 20, 21, 22, 23, 24, 25 or more contiguous residues found in SEQ ID NO:1, 3, 5, 7, 9, 11 or 13. In some embodiments, useful nucleic acids are generated in vitro; in some embodiments, useful nucleic acids are generated in vivo. In some embodiments, useful nucleic acids are generated using genetic engineering techniques (e.g., for production and/or mutagenesis of a reference sequence). To give but a few examples, in some embodiments, nucleic acid variants (e.g., of SEQ ID NO:1, 3, 5, 7, 9, 11 or 13) are generated using techniques such as site directed mutagenesis, random chemical mutagenesis, Exonuclease III deletion procedures, and standard cloning techniques. In some embodiments, useful nucleic acids are generating using chemical synthesis and/or modification procedures.

A variety of methods of making nucleic acids that are "variants" with respect to a reference nucleic acid (e.g., a naturally-occurring or other reference nucleic acid) are well known in the art. These include, for example, procedures in which nucleic acid sequences obtained from natural isolates are modified to generate nucleic acids that encode polypeptides having characteristics that enhance their value in industrial or laboratory applications. In such some embodiments of such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants can be created using error prone PCR (see, e.g., Leung et al., Technique 1:11-15, 1989; and Caldwell et al., PCR Methods Applic. 2:28-33, 1992). In error prone PCR, PCR is performed under conditions where the copying fidelity of the DNA polymerase is low, such that a high rate of point mutations is obtained along the entire length of the PCR product. Briefly, in such procedures, nucleic acids to be mutagenized are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mM KCl, 10 mM Tris HCl (pH 8.3), and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated that these parameters can be varied as appropriate. The mutagenized nucleic acids are then cloned into an appropriate vector and the activities of the polypeptides encoded by the mutagenized nucleic acids are evaluated.

Variants can also be created using oligonucleotide directed mutagenesis to generate site-specific mutations in any cloned DNA of interest. Oligonucleotide mutagenesis is described in, for example, Reidhaar-Olson et al., Science 241:53-57 (1988). Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered, and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No. 5,965,408. Still another method of generating variants is sexual PCR mutagenesis. In sexual PCR mutagenesis, forced homologous recombination occurs between DNA molecules of different, but highly related, DNA sequence in vitro as a result of random fragmentation of the DNA molecule based on sequence homology. This is followed by fixation of the crossover by primer extension in a PCR reaction. Sexual PCR mutagenesis is described in, for example, Stemmer, Proc. Natl. Acad. Sci., USA 91:10747-10751 (1994).

Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such "mutator" strains have a higher random mutation rate than that of a wild-type strain. Propagating a DNA sequence in one of these strains will generate random mutations within the DNA. Mutator strains suitable for use for in vivo mutagenesis are described in, for example, PCT Publication No. WO 91/16427.

Variants can also be generated using cassette mutagenesis. In cassette mutagenesis, a small region of a double stranded DNA molecule is replaced with a synthetic oligonucleotide "cassette" that differs from the native sequence. The oligonucleotide often contains a completely and/or partially randomized native sequence. Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., Proc. Natl. Acad. Sci., USA 89:7811-7815 (1992).

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., Biotech. Res. 11:1548-1552 (1993). Random and site-directed mutagenesis are described in, for example, Arnold, Curr. Opin. Biotech. 4:450-455 (1993). In some embodiments, variants are created using shuffling procedures wherein portions of a plurality of nucleic acids that encode distinct polypeptides are fused together to create chimeric nucleic acid sequences that encode chimeric polypeptides as described in, for example, U.S. Pat. Nos. 5,965,408 and 5,939,250.

In some embodiments, nucleic acids for use in accordance with the present disclosure comprise naturally-occurring nucleotide residues. In some embodiments, nucleic acids for use in accordance with the present disclosure include one or more nucleotide "analogs". A nucleotide analog is a nucleotide (i.e., an entity that is incorporated into a nucleic acid polymer without significantly disrupting the structure and/or function of that polymer) whose chemical structure differs from that of reference naturally-occurring ribonucleic or deoxyribonucleic acid residues adenine, guanine, cytosine, thymine, and uracil. In some embodiments, a nucleotide analog differs from its reference nucleotide at the base moiety, sugar moiety, and/or phosphate backbone. In some embodiments, a nucleotide analog contributes to one or more altered features in a nucleic acid polymer into which it is incorporated as compared with a comparable nucleic acid polymer containing its reference nucleotide rather than the analog. For example, in some embodiments, such analog-containing polymer shows improved, stability, hybridization, and/or solubility.

In some embodiments, base moiety alterations found in nucleotide analogs include deoxyuridine for deoxythymidine and 5-methyl-2'-deoxycytidine or 5-bromo-2'-deoxycytidine for deoxycytidine. In some embodiments, sugar moiety alterations found in nucleotide analogs include modification of the 2' hydroxyl of the ribose sugar to form 2'-O-methyl or 2'-O-allyl sugars. In some embodiments, deoxyribose phosphate backbone alterations found in nucleotide analogs include morpholino nucleic acids, in which each base moiety is linked to a six-membered, morpholino ring, or peptide nucleic acids, in which the deoxyphosphate backbone is replaced by a pseudopeptide backbone and the four bases are retained (see, e.g., Summerton et al., Antisense Nucleic Acid Drug Dev. 7:187-195 (1997); Hyrup et al., Bioorgan. Mcd. Chem. 4:5-23(1996)). Alternatively or additionally, nucleotide analogs may have a phosphorothioate or phosphorodithioate backbone, a phosphoroamidite, or an alkyl phosphotriester backbone.

In certain instances, an NMD polynucleotide or variant for use in accordance with the present disclosure includes alterations to codon(s) to optimize for expression in a particular host cell. For example, for expression in *E. coli*, an NMP polynucleotide or variant can include one or more altered codons as described in, e.g., Grosjean et al., Gene 18:199-209 (1982).

NMD Polypeptides

In some embodiments, methods and compositions described utilize NMD polypeptides (e.g., UPF1, UPF2, UPF3, SMG1, SMG5, SMG6, or SMG7 polypeptides). According to the present disclosure, such polypeptides are useful in the treatment of ALS. In some embodiments, such polypeptides useful in the practice of the present disclosure have or include amino acid sequences as set forth in SEQ ID NO:2, 4, 6, 8, 10, 12, or 14, or characteristic sequence elements thereof or therein. In some embodiments, useful polypeptides show at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% overall sequence identity with one or more of SEQ ID NO:2, 4, 6, 8, 10, 12, or 14. Alternatively or additionally, in some embodiments, useful polypeptides include at least about 5, 10, 15, 20, 25, 30, 35, 40, 45, 50, 75, 100, or 150 or more contiguous amino acid residues found in SEQ ID NO:2, 4, 6, 8, 10, 12, or 14.

In some embodiments, a useful polypeptide differs from its reference polypeptide (e.g., a polypeptide having or including an amino acid sequence as set forth in SEQ ID NO:2, 4, 6, 8, 10, 12, or 14, or characteristic sequence elements thereof or therein) by one or more amino acid residues. For example, in some embodiments, the difference is a conservative or nonconservative substitution of one or more amino acid residues. Conservative substitutions are those that substitute a given amino acid in a polypeptide by another amino acid of similar characteristics. Typical conservative substitutions are the following replacements: replacement of an aliphatic amino acid, such as alanine, valine, leucine, and isoleucine, with another aliphatic amino acid; replacement of a serine with a threonine or vice versa; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

In some embodiments, useful NMD polypeptides include a substituent group on one or more amino acid residues. Still other useful polypeptides are associated with (e.g., fused, linked, or coupled to) another moiety (e.g., a peptide or molecule). For example, useful NMD polypeptides can be fused, linked, or coupled to an amino acid sequence (e.g., a leader sequence, a secretory sequence, a proprotein sequence, a second polypeptide, or a sequence that facilitates purification, enrichment, or stabilization of the polypeptide). In certain other embodiments, a polypeptide includes a targeting agent, e.g., a targeting agent described herein.

A variety of methods of making polypeptides are known in the art and can be used to make NMD polypeptides. For example, NMD polypeptides can be recombinantly produced by utilizing a host cell system engineered to express a nucleic acid encoding an NMD polypeptide (e.g., a nucleic acid described herein). Alternatively or additionally, an NMD polypeptide can be produced by activating an endogenous gene (e.g., a nucleic acid encoding an NMD polypeptide present endogenously in a cell). Alternatively or additionally, an NMD polypeptide can be partially or fully prepared by chemical synthesis. Alternatively or additionally, an NMD polypeptide can be purified from natural sources.

Where an NMD polypeptide is recombinantly produced, any expression system can be used. Known expression systems include, without limitation, for example, egg, baculovirus, plant, yeast, or mammalian cells.

In some embodiments, an NMD polypeptide suitable for use in methods described herein are produced in mammalian cells. Non-limiting examples of mammalian cells that can be used include BALB/c mouse myeloma line (NSW, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

Targeting Agents

An NMD agent described herein can be provided in association with and/or can include a targeting agent.

The present disclosure is not limited to any particular targeting agent, and a variety of targeting agents can be used. Examples of such targeting agents include, but are not limited to, nucleic acids (e.g., RNA and DNA), polypeptides (e.g., receptor ligands, signal peptides, avidin, Protein A, and antigen binding proteins), polysaccharides, biotin, hydrophobic groups, hydrophilic groups, drugs, and any organic molecules that bind to target cells or target tissues (e.g., receptors on target cells or target tissues).

Targeting agents can be associated with NMD agents in any of a number of ways. For example, polypeptide targeting agents can be coupled to or fused to an NMD polypeptide. In other embodiments, a targeting agent is associated (e.g., covalently or noncovalently bound) to an NMD agent with either short (e.g., direct coupling), medium (e.g., using small-molecule bifunctional linkers such as SPDP (Pierce Biotechnology, Inc., Rockford, Ill.)), or long (e.g., PEG bifunctional linkers (Nektar Therapeutics, Inc., San Carlos, Calif.)) linkages.

In some instances, targeting agents are or comprise antigen binding proteins or antibodies or binding portions thereof. Antibodies can be generated to allow for specific targeting of antigens or immunogens (e.g., target cell or target tissue specific antigens). Such antibodies include, but are not limited to, polyclonal antibodies; monoclonal antibodies or antigen binding fragments thereof; modified antibodies such as chimeric antibodies, reshaped antibodies, humanized antibodies, or fragments thereof (e.g., Fv, Fab', Fab, F(ab')$_2$); or biosynthetic antibodies, e.g., single chain antibodies, single domain antibodies (DAB), Fvs, or single chain Fvs (scFv) (see, e.g., in Harlow et al., Using Antibodies: A Laboratory Manual: Portable Protocol I. Cold Spring Harbor Laboratory (Dec. 1, 1998); Zola, Monoclonal Antibodies: Preparation and Use of Monoclonal Antibodies and Engineered Antibody Derivatives, Springer Verlag (Dec. 15, 2000; 1st edition)). Antibody attachment can be performed by any known method e.g., through standard covalent binding to free amine groups (see, e.g., Torchilin et al., Hybridoma 6:229-240 (1987); Torchilin et al, Biochim. Biophys. Acta 1511:397-411 (2001); Masuko et al., Biomacromol. 6:800-884 (2005)).

In some instances, a targeting agent is or comprises a nucleic acid (e.g., RNA or DNA). In some examples, nucleic acid targeting agents are designed to hybridize by base pairing to a particular nucleic acid (e.g., chromosomal DNA, mRNA, or ribosomal RNA). In some situations, nucleic acid targeting agents bind a ligand on a target cell or target tissue. For example, a nucleic acid can bind human nerve growth factor (Binkley et al., Nuc. Acids Res. 23:3198-205 (1995)). Nucleic acids that bind ligands can be identified by known methods, such as SELEX procedures (see, e.g., U.S. Pat. Nos. 5,475,096; 5,270,163; and 5,475,096; and WO 97/38134; WO 98/33941; and WO 99/07724). In some embodiments, targeting agents can be or comprise aptamers, for example that bind to particular sequences.

In some embodiments, a targeting agent binds to a receptor on the surface of a brain cell to facilitate cellular uptake. For example, a targeting agent can be mannose-6-phosphate (M6P), bis-phosphorylated oligosaccharides, or IGF-II, which are useful for targeting the cation-independent mannose-6-phosphate receptor (CI-MPR) on a brain cell. In some embodiments, a targeting agent is or comprises ascorbate, which is taken up by a sodium-dependent-vitamin C transporter (SVCT2), (see, e.g., Tsukaguchi et al., Nature 399:70-75 (1999)), which is useful for targeting to a brain cell.

Therapeutic Administration

NMD agents (e.g., NMD polynucleotides, a nucleic acid encoding an NMD polypeptide, or an agent that increases NMD polypeptide level and/or activity) described herein can be used to treat ALS, e.g., subjects suffering from or susceptible to ALS. The route and/or mode of administration of an NMD agent described herein can vary depending upon the desired results. One with skill in the art, i.e., a physician, is aware that dosage regimens can be adjusted to provide the desired response, e.g., a therapeutic response.

Methods of administration include, but are not limited to, intradermal, intramuscular, intraperitoneal, intravenous, subcutaneous, intranasal, epidural, oral, sublingual, intracerebral, intrathecal, intravaginal, transdermal, rectal, by inhalation, or topical, particularly to the ears, nose, eyes, or skin. The mode of administration is left to the discretion of the practitioner.

In some instances, an NMD agent described herein (e.g., a pharmaceutical formulation of an NMD agent) can effectively cross the blood brain barrier and enter the brain. In other instances, an NMD agent can be delivered using techniques designed to permit or to enhance the ability of the formulation to cross the blood-brain barrier. Such techniques are known in the art (e.g., WO 89/10134; Cloughesy et al., J. Neurooncol. 26:125-132 (1995); and Begley, J. Pharm. Pharmacol. 48:136-146 (1996)). Components of a formulation can also be modified (e.g., chemically) using methods known in the art to facilitate their entry into the CNS.

For example, physical methods of transporting compositions across the blood-brain barrier include, but are not limited to, circumventing the blood-brain barrier entirely, or by creating openings in the blood-brain barrier. Circumvention methods include, but are not limited to, direct injection into the brain (see e.g., Papanastassiou et al., Gene Therapy 9: 398-406 (2002)) and implanting a delivery device in the brain (see e.g., Gill et al., Nature Med. 9: 589-595 (2003); and Gliadel Wafers™, Guildford Pharmaceutical). Methods of creating openings in the barrier include, but are not limited to, ultrasound (see e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding an NMD agent (see, e.g., U.S. Patent Publ. No. 20030083299).

Lipid-based methods can also be used to transport an NMD agent across the blood-brain barrier. Exemplary, non-limiting methods include encapsulating an NMD agent in liposomes that are coupled to a targeting agent described herein (e.g., an antibody that binds to receptors on vascular endothelium of the blood-brain barrier (see, e.g., U.S. Patent Publ. No. 20020025313). In certain other embodiments, a targeting agent is coated in low-density lipoprotein particles (see, e.g., U.S. Patent Publ. No. 20040204354) or apolipoprotein E (see, e.g., U.S. Patent Publ. No. 20040131692).

In some embodiments, an NMD agent is delivered to the CNS of a subject, e.g., by administering into the cerebrospinal fluid (CSF) of a subject in need of treatment. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al., Adv. Tech. Stand. Neurosurg. 18:143-192 (1991), and Omaya, Cancer Drug Deliv. 1:169-179 (1984).

In some instances, an NMD agent described herein is administered locally. This can be achieved, for example, by local infusion during surgery, topical application (e.g., in a cream or lotion), by injection, by means of a catheter, by means of a suppository or enema, or by means of an implant, said implant being of a porous, non-porous, or gelatinous material, including membranes, such as sialastic membranes, or fibers. In some situations, an NMD agent described herein is introduced into the central nervous system, circulatory system or gastrointestinal tract by any suitable route, including intraventricular injection, intrathecal injection, paraspinal injection, epidural injection, enema, and by injection adjacent to a peripheral nerve.

Specifically, various devices can be used for intrathecal delivery of NMD agents described herein. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. Various other devices may be used to effect intrathecal administration of a therapeutic composition. For example, formulations containing NMD agents can be administered using an Ommaya reservoir that is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver an NMD agent, which is injected into the reservoir. Other devices for intrathecal administration of therapeutic compositions or formulations to an individual are described in U.S. Pat. No. 6,217,552. Alternatively, an NMD agent can be intrathecally given, for example, by a single injection, or continuous infusion. It should be understood that the dosage treatment may be in the form of a single dose administration or multiple doses.

In some embodiments, intrathecal administration can be performed by either lumbar puncture (i.e., slow bolus) or via a port-catheter delivery system (i.e., infusion or bolus).

Relative to intravenous administration, a single dose volume suitable for intrathecal administration is typically small. Typically, intrathecal delivery maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before intrathecal administration. In those cases, a suitable single dose volume may be e.g., more than about 3 ml, 4 ml, 5 ml, 6 nil, 7 ml, 8 ml, 9 ml, 10 ml, 15 ml, or 20 ml.

Pulmonary administration can also be employed, e.g., by use of an inhaler or nebulizer, and formulation with an aerosolizing agent, or via perfusion in a fluorocarbon or synthetic pulmonary surfactant.

An NMD agent described herein can be formulated as a pharmaceutical composition that includes a suitable amount of a physiologically acceptable excipient (see, e.g., Remington's Pharmaceutical Sciences pp. 1447-1676 (Alfonso R. Gennaro, ed., 19th ed. 1995)). Such physiologically acceptable excipients can be, e.g., liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one situation, the physiologically acceptable excipients are sterile when administered to an animal. The physiologically acceptable excipient should be stable under the conditions of manufacture and storage and should be preserved against the contaminating action of microorganisms. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable physiologically acceptable excipients are described in Remington's Pharmaceutical Sciences pp. 1447-1676 (Alfonso R. Gennaro, ed., 19th ed. 1995). The pharmaceutical compositions, if desired, can also contain minor amounts of wetting or emulsifying agents, or pH buffering agents.

Liquid carriers can be used in preparing solutions, suspensions, emulsions, syrups, and elixirs. An NMD agent described herein can be suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives described herein, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. The liquid carriers can be in sterile liquid form for administration. The liquid carrier for pressurized compositions can be halogenated hydrocarbon or other pharmaceutically acceptable propellant.

In other instances, an NMD agent described herein is formulated for intravenous administration. Compositions for intravenous administration can comprise a sterile isotonic aqueous buffer. The compositions can also include a solubilizing agent. Compositions for intravenous administration can optionally include a local anesthetic such as lidocaine to lessen pain at the site of the injection. The ingredients can be supplied either separately or mixed together in unit dosage form, for example, as a dry lyophilized powder or water-free concentrate in a hermetically sealed container such as an ampule or sachette indicating the quantity of active agent. Where an NMD agent described herein is administered by infusion, it can be dispensed, for example, with an infusion bottle containing sterile pharmaceutical grade water or saline. Where an NMD agent described herein is administered by injection, an ampule of sterile water for injection or saline can be provided so that the ingredients can be mixed prior to administration.

An NMD agent described herein can be administered rectally or vaginally in the form of a conventional suppository. Suppository formulations can be made using methods known to those in the art from traditional materials, including cocoa butter, with or without the addition of waxes to alter the suppository's melting point, and glycerin. Water-soluble suppository bases, such as polyethylene glycols of various molecular weights, can also be used.

The amount of an NMD agent described herein that is effective for treating ALS can be determined using standard clinical techniques known to those with skill in the art. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner.

Compositions described herein (e.g., therapeutically effective amounts of compositions described herein) can be administered as single administrations or as multiple administrations. Such compositions can be administered at regular intervals, depending on the nature, severity and extent of the subject's condition (e.g., ALS). In some embodiments, a therapeutically effective amount of a therapeutic agent (e.g., an NMD agent) is administered intrathecally periodically at regular intervals (e.g., once every year, once every six months, once every five months, once every three months, bimonthly (once every two months), monthly (once every month), biweekly (once every two weeks), or weekly).

As used herein, the term "therapeutically effective amount" is largely determined based on the total amount of the therapeutic agent contained in pharmaceutical compositions described herein. Generally, a therapeutically effective amount is sufficient to achieve a meaningful benefit to a subject (e.g., treating, modulating, curing, preventing and/or ameliorating ALS). For example, a therapeutically effective amount can be an amount sufficient to achieve a desired therapeutic and/or prophylactic effect, such as an amount sufficient to treat ALS or the symptoms thereof. Generally, the amount of a therapeutic agent (e.g., an NMD agent) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays can optionally be employed to identify optimal dosage ranges. A therapeutically effective amount can be administered in a dosing regimen that can include multiple unit doses.

In some embodiments, a therapeutically effective dose ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, a therapeutically effective dose is greater than about 0.1 mg/kg brain weight, greater than about 0.5 mg/kg brain weight, greater than about 1.0 mg/kg brain weight, greater than about 3 mg/kg brain weight, greater than about 5 mg/kg brain weight, greater than about 10 mg/kg brain weight, greater than about 15 mg/kg brain weight, greater than about 20 mg/kg brain weight, greater than about 30 mg/kg brain weight, greater than about 40 mg/kg brain weight, greater than about 50 mg/kg brain weight, greater than about 60 mg/kg brain weight, greater than about 70 mg/kg brain weight, greater than about 80 mg/kg brain weight, greater than about 90 mg/kg brain weight, greater than about 100 mg/kg brain weight, greater than about 150 mg/kg brain weight, greater than about 200 mg/kg brain weight, greater than about 250 mg/kg brain weight, greater than about 300 mg/kg brain weight, greater than about 350 mg/kg brain weight, greater than about 400 mg/kg brain weight, greater than about 450 mg/kg brain weight, greater than about 500 mg/kg brain weight.

In some embodiments, a therapeutically effective dose can be expressed as mg/kg body weight. As one skilled in the art would appreciate, brain weights and body weights can be correlated (see, e.g., Dekaban, Ann. Neurol. 4:345-56 (1978)).

In some embodiments, a therapeutically effective dose can be expressed as mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson et al., Cerebrospinal Fluid Res. 14:5:10 (2008)). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens can be adjusted over time according to the individual need and the professional judgment of the person administering or supervising the administration of an NMD agent and that dosage ranges set forth herein are exemplary only and are not intended to limit the scope or practice of the claimed invention.

In some instances, a pharmaceutical composition described herein is in unit dosage form, e.g., as a tablet, capsule, powder, solution, suspension, emulsion, granule, or suppository. In such form, the pharmaceutical composition can be sub-divided into unit doses containing appropriate quantities of an NMD agent described herein. The unit dosage form can be a packaged pharmaceutical composition, for example, packeted powders, vials, ampoules, pre-filled syringes or sachets containing liquids. The unit dosage form can be, for example, a capsule or tablet itself, or it can be the appropriate number of any such compositions in package form. Such unit dosage form can contain from about 1 mg/kg to about 250 mg/kg, and can be given in a single dose or in two or more divided doses.

Gene Therapy

In embodiments in which an NMD agent consists of or comprises a nucleic acid encoding an NMD polypeptide, the present disclosure includes methods of administering such nucleic acid to a subject to treat ALS.

In some embodiments, a nucleic acid encoding an NMD polypeptide is inserted into a viral vector for delivery to a subject. For example, retrovirus vectors can be used as a recombinant delivery system for transferring nucleic acids encoding NMD polypeptides vivo (see, e.g., Dropulic, Hum. Gene Ther. 22:649-57 (2011); and Kumar et al., Curr. Gene Ther. 11:144-53 (2011)). Retroviruses useful in methods of the present disclosure include, but are not limited to, murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), FBR murine osteosarcoma virus (FBR MSV), Moloney murine sarcoma virus (Mo-MSV), Abelson murine leukemia virus (A-MLV), Avian myelocytomatosis virus-29 (MC29), Avian erythroblastosis virus (AEV) and all other retroviridiae including lentiviruses (see, e.g., Coffin et al., "Retroviruses", 1997 Cold Spring Harbor Laboratory Press Eds: J M Coffin, S M Hughes, H E Varmus, pp 758-763)). A replication defective retrovirus can be packaged into virions that can be used to infect a target cell through the use of a helper virus by standard techniques (see, e.g., Current Protocols in Molecular Biology, Ausubel, F. M. et al. (eds.) Greene Publishing Associates, (1989), Sections 9.10-9.14).

In other embodiments, adenovirus-derived vectors are used to deliver nucleic acids encoding NMD polypeptides. The genome of an adenovirus can be manipulated such that it encodes and expresses an NMD polypeptide, but is inactivated in terms of its ability to replicate in a normal lytic viral life cycle (see, e.g., Berkner et al. (1988) BioTechniques 6:616; Rosenfeld et al. (1991) Science 252:431-434; and Rosenfeld et al. (1992) Cell 68:143-155). Suitable adenoviral vectors useful in the methods of the present disclosure include those derived from the adenovirus strain Ad type 5 d1324 or other strains of adenovirus (e.g., Ad2, Ad3, Ad7 etc.).

In some embodiments, an adeno-associated virus (AAV) is used to deliver a nucleic acid encoding an NMD polypeptide (see, e.g., Muzyczka et al. (1992) Curr. Topics in Micro. and Immunol. 158:97-129). A variety of nucleic acids have been introduced into different cell types using AAV vectors (see, e.g., Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. \Tirol. 51:611-619; and Flotte et al. (1993) J. Biol. Chem. 268:3781-3790). Particularly useful AAVs include those that normally infect humans (e.g., serotypes 1, 2, 3A, 3B, 4, 5, and 6) or primates (e.g., serotypes 1 and 4).

In other embodiments, non-viral methods are useful to deliver a nucleic acid encoding an NMD polypeptide to a subject. Such nonviral methods of gene transfer can exploit mechanisms normally used by mammalian cells for uptake and intracellular transport of macromolecules. For example, liposomal delivery systems, poly-lysine conjugates, and artificial viral envelopes can be used. In some embodiments, a nucleic acid encoding au NMD polypeptide is entrapped in liposomes bearing positive charges on their surface (e.g., lipofectins), In some embodiments, a liposome can be conjugated to a targeting agent described herein (see, e.g., Mizuno et al. (1992) No Shinkei Geka 20:547-551).

Certain cationic polymers ("complexation agents") known to spontaneously bind to and condense nucleic acids into nanoparticles can also be used including, e.g., naturally occurring proteins, peptides, or derivatives, as well as synthetic cationic polymers such as polyethylenimine (PEI), polylysine (PLL), etc. Many useful polymers contain both chargeable amino groups, to allow for ionic interaction with negatively charged DNA phosphate, and a degradable region, such as a hydrolyzable ester linkage. Examples of these include, without limitation, poly(alpha-(4-aminobutyl)-L-glycolic acid), network poly(amino ester), and poly(beta-amino esters). Such complexation agents can protect DNA against degradation, e.g., by nucleases, serum components, etc., and create a less negative surface charge, which may facilitate passage through hydrophobic membranes (e.g., cytoplasmic, lysosomal, endosomal, nuclear) of the cell. Certain complexation agents facilitate intracellular trafficking events such as endosomal escape, cytoplasmic transport, and nuclear entry, and can dissociate from the nucleic acid.

Cell-Based Therapy

An NMD polynucleotide can also be advantageously provided to a cell ex vivo, followed by administration of the living cell to the subject. In some embodiments, primary or secondary cells are genetically engineered to express an NMD polypeptide. Such cells can be obtained from a variety of tissues and include cell types which can be maintained propagated in culture. For example, primary and secondary cells include fibroblasts, endothelial cells, glial cells, and neural cells. In some embodiments, primary cells are obtained from an individual to whom a genetically engineered primary or secondary cells is to be administered. Primary cells can also be obtained from a donor (other than the recipient) of the same species or another species (e.g., mouse, rat, rabbit, cat, dog, pig, cow, bird, sheep, goat, horse).

Primary or secondary cells (e.g., of vertebrate or mammalian origin) can be transfected with a nucleic acid encoding an NMD polypeptide. In some embodiments, a cell is transfected with an exogenous nucleic acid sequence that includes a nucleic acid encoding an NMD polypeptide and an additional nucleic acid sequence (e.g., a regulatory sequence, e.g., a promoter, which causes expression, e.g., inducible expression or upregulation, of an endogenous NMD sequence). Transfected primary or secondary cells may also include DNA encoding a selectable marker which confers a selectable phenotype upon them, facilitating their identification and isolation.

Methods for treating disease by implanting a cell that has been modified to express a recombinant protein are also well known. See, for example, U.S. Pat. No. 5,399,346, disclosing methods for introducing a nucleic acid into a primary human cell for introduction into a human. Although use of human cells for ex vivo therapy is preferred in some embodiments, other cells such as bacterial cells may be implanted in a subject's vasculature, continuously releasing a therapeutic agent. See, for example, U.S. Pat. Nos. 4,309, 776 and 5,704,910.

Kits

An NMD agent described herein (e.g., a pharmaceutical composition comprising an NMD agent) can be provided in a kit. In some instances, the kit includes (a) a container that contains an NMD agent described herein (e.g., a pharmaceutical composition comprising an NMD agent) and, optionally (b) informational material. The informational material can be descriptive, instructional, marketing or other material that relates to the methods described herein and/or the use of an NMD agent, e.g., for therapeutic benefit.

The informational material of the kits is not limited in its form. In some instances, the informational material can include information about production of an NMD agent, molecular weight of an NMD agent, concentration, date of expiration, batch or production site information, and so forth. In other situations, the informational material relates to methods of administering an NMD agent, e.g., in a suitable amount, manner, or mode of administration (e.g., a dose, dosage form, or mode of administration described herein). The method can be a method of treating a subject having ALS.

In some cases, the informational material, e.g., instructions, is provided in printed matter, e.g., a printed text, drawing, and/or photograph, e.g., a label or printed sheet. The informational material can also be provided in other formats, such as Braille, computer readable material, video recording, or audio recording. In other instances, the informational material of the kit is contact information, e.g., a physical address, email address, website, or telephone number, where a user of the kit can obtain substantive information about an NMD agent therein and/or their use in the methods described herein. The informational material can also be provided in any combination of for mats.

In addition to an NMD agent, the kit can include other ingredients, such as a solvent or buffer, a stabilizer, or a preservative. The kit can also include other agents, e.g., a second or third agent, e.g., other therapeutic agents. The components can be provided in any form, e.g., liquid, dried or lyophilized form. The components can be substantially pure (although they can be combined together or delivered separate from one another) and/or sterile. When the components are provided in a liquid solution, the liquid solution can be an aqueous solution, such as a sterile aqueous solution. When the components are provided as a dried form, reconstitution generally is by the addition of a suitable solvent. The solvent, e.g., sterile water or buffer, can optionally be provided in the kit.

The kit can include one or more containers for an NMD agent or other agents. In some cases, the kit contains separate containers, dividers or compartments for an NMD agent and informational material. For example, an NMD agent can be contained in a bottle, vial, or syringe, and the informational material can be contained in a plastic sleeve or packet. In other situations, the separate elements of the kit are contained within a single, undivided container. For example, an NMD agent can be contained in a bottle, vial or syringe that has attached thereto the informational material in the form of a label. In some cases, the kit can include a plurality (e.g., a pack) of individual containers, each containing one or more unit dosage forms (e.g., a dosage form described herein) of an NMD agent. The containers can include a unit dosage, e.g., a unit that includes an NMD agent. For example, the kit can include a plurality of syringes, ampules, foil packets, blister packs, or medical devices, e.g., each containing a unit dose. The containers of the kits can be air tight, waterproof (e.g., impermeable to changes in moisture or evaporation), and/or light-tight.

The kit can optionally include a device suitable for administration of an NMD agent, e.g., a syringe or other suitable delivery device. The device can be provided preloaded with an NMD agent, e.g., in a unit dose, or can be empty, but suitable for loading.

Treatment of ALS

The present invention encompasses the surprising finding that NMD agents are useful, among other things, in the treatment or prevention (i.e., delay of onset) of ALS. UPF1 was initially identified as one of many genes able to rescue toxicity mediated by FUS/TLS in a yeast model (Ju et al., PLoS Biol. 9:e1001052 (2011)). However, the present finding that expressing UPF1 in neuronal cells expressing FUS/TLS or TDP-43 reduces cellular toxicity is surprising, especially given the finding that expression of UPF1 had no effect on the cytoplasmic levels of FUS/TLS or TDP-43 in the neuronal cells. Accordingly, in some embodiments, an NMD agent is provided to the central nervous system of a subject, e.g., a subject suffering from or susceptible to ALS. In some embodiments, an NMD agent is provided to one or more of target cells or tissues of brain, spinal cord, and/or peripheral organs. In some embodiments, target cells or tissues include those cells or tissues that display a disease-associated pathology, symptom, or feature. In some embodiments, target cells or tissues include those cells or tissues in which TDP-43 or FUS/TLS is expressed at an elevated level, e.g., cells in which TDP-43 or FUS/TLS is expressed at an elevated level in the cytoplasm of the cells. As used herein, a target tissue may be a brain target tissue, a spinal cord target tissue and/or a peripheral target tissue.

Compositions described herein can be provided directly into the CNS of a subject suffering from or at risk of developing ALS, thereby achieving a therapeutic concentration within the affected cells and tissues of the CNS (e.g., the brain). For example, one or more NMD agents can be provided to target cells or tissues of the brain, spinal cord and/or peripheral organs to treat ALS. As used herein, the term "treat" or "treatment" refers to amelioration of one or more symptoms associated with the disease, prevention or delay of the onset of one or more symptoms of the disease, and/or lessening of the severity or frequency of one or more symptoms of the disease.

In some embodiments, treatment refers to partially or complete alleviation, amelioration, relief, inhibition, delaying onset, reducing severity and/or incidence of neurological impairment in a patient suffering from or susceptible to ALS. As used herein, the term "neurological impairment" includes various symptoms associated with impairment of the central nervous system (e.g., the brain and spinal cord). Symptoms of neurological impairment may include, for example, developmental delay, progressive cognitive impairment, hearing loss, impaired speech development, deficits in motor skills, hyperactivity, aggressiveness and/or sleep disturbances, among others.

In some embodiments, treatment refers to decreased toxicity of various cells or tissues. In some embodiments, treatment refers to decreased neuronal toxicity due to FUS or TDP-43 in brain target tissues, spinal cord neurons, and/or peripheral target tissues. In certain embodiments, toxicity is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, toxicity is decreased by at least 1-fold, 2-fold, 3-fold, 4-fold, 5-fold, 6-fold, 7-fold, 8-fold, 9-fold or 10-fold as compared to a control. In some embodiments, toxicity is measured by tests known to those of ordinary skill in the art including, but not limited to, neuroimaging methods (e.g., CT scans, MRI, functional MRI, etc.).

In certain embodiments, treatment according to the present disclosure results in a reduction (e.g., about a 5%, 10%, 15%, 20%, 25%, 30%, 40%, 50%, 55%, 60%, 65%, 70%, 75%, 80%, 90%, 95%, 97.5%, 99% or more reduction) or a complete elimination of the presence, or alternatively the accumulation, of one or more pathological, clinical, or biological markers that are associated with ALS. For example, in some embodiments, upon administration to a subject, a pharmaceutical composition described herein demonstrates or achieves a reduction in muscle loss, muscle twitching, muscle weakness, spasticity, abnormal tendon reflexes, Babinski sign, breathing problems, facial weakness, slurred speech, loss of perception, loss of reasoning, loss of judgment, and/or loss of imagination.

In some embodiments, treatment refers to increased survival (e.g., survival time). For example, treatment can result in an increased life expectancy of a patient. In some embodiments, treatment results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with ALS without treatment. In some embodiments, treatment results in an increased life expectancy of a patient by more than about 6 months, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with ALS without treatment. In some embodiments, treatment results in long term survival of a patient. As used herein, the term "long term survival" refers to a survival time or life expectancy longer than about 40 years, 45 years, 50 years, 55 years, 60 years, or longer.

The term "improve," "increase" or "reduce," as used herein, indicates values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with ALS, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having ALS or having the potential to develop ALS. In some instances, a subject to be treated is genetically predisposed to developing ALS. For example, a subject to be treated has a mutation in a SOD1 gene, ALS2 gene, VAPB gene, SETX gene, TDP-43 gene, FUS/TLS gene, and/or OPTN gene.

Combination Therapy

In some embodiments, an NMD agent described herein is administered to a subject in combination with one or more additional therapies to treat ALS or one or more symptoms of ALS. For example, an NMD agent can be administered in combination with riluzole (Rilutek®, Sanofi-Aventis, Bridgewater, N.J.), baclofen, diazepam, trihexyphenidyl or amitriptyline.

In some embodiments, combined administration of an NMD agent and a second agent results in an improvement in ALS or a symptom thereof to an extent that is greater than one produced by either the NMD agent or the second agent alone. The difference between the combined effect and the effect of each agent alone can be a statistically significant difference.

In some embodiments, combined administration of an NMD agent and a second agent allows administration of the second agent at a reduced dose, at a reduced number of doses, and/or at a reduced frequency of dosage compared to a standard dosing regimen approved for the second agent. For example, approved standard regimen for Rilutek® is 50 mg every 12 hours. Accordingly, for administration in combination with an NMD agent, a therapeutically effective amount of Rilutek® can be a dosage of less than about 50 mg and/or a frequency of greater than about every 12 hours.

In some embodiments, an immunosuppressant agent known to the skilled artisan can be administered to a subject in combination with an NMD polypeptide described herein. Exemplary immunosuppressant agents include, without limitation, cyclosporine, FK506, rapamycin, CTLA4-Ig, anti-TNF agents (such as etanercept), daclizumab (e.g., Zenapax™), anti-CD2 agents, anti-CD4 agents, and anti-CD40 agents.

Methods of Identifying Modulators of NMD Polypeptide Expression or Activity

NMD polypeptides described herein (e.g., UPF1, UPF2, UPF3, SMG1, SMG5, SMG6, or SMG7 polypeptides) are useful for identifying agents that can be potentially used to treat ALS. For example, an agent that increases expression or activity of an NMD polypeptide can be identified as an agent that can be used to treat ALS. Numerous methods exist for evaluating whether an agent alters NMD polypeptide expression or NMD polypeptide activity or level. In one embodiment, the ability of a test agent to modulate (e.g., increase or decrease) (e.g., permanently or temporarily) expression from an NMD polynucleotide promoter is evaluated by e.g., routine reporter (e.g., LacZ, luciferase, or GFP) transcription assay. For example, a cell or transgenic animal whose genome comprises a reporter gene operably linked to an NMD polynucleotide promoter, can be contacted with a test agent, and the ability of the test agent to increase or decrease reporter activity is indicative of the ability of the agent to modulate an NMD polypeptide.

In some embodiments, effects of a test agent on NMD polypeptide expression or NMD polypeptide activity or level can be evaluated in a cell, cell lysate, or subject, preferably a non-human experimental mammal, and more preferably a rodent (e.g., a rat, mouse, rabbit), or explant thereof. Methods of assessing NMD polypeptide expression are well know in the art, e.g., Northern analysis, ribonuclease protection assay, reverse transcription-polymerase chain reaction (RT-PCR) or RNA in situ hybridization (see, e.g., Sambrook et al. Molecular Cloning: A Laboratory Manual ($3^{rd}$ ed. 2001)). The level of NMD polypeptide can be monitored by, e.g., Western analysis, immunoassay, or in situ hybridization. In some embodiments, a DNA construct encoding an NMD polypeptide/GFP fusion protein is transfected into cells, and level of GFP fluorescence in the presence or absence of a test agent is determined. An increase in fluorescence in the presence of the test agent is indicative of the ability of the test agent to increase NMD polypeptide level.

In some embodiments, the effect of a test agent on NMD polypeptide expression or NMD polypeptide activity or level is confirmed in a second assay, e.g., is observed as a change, in the presence of the test agent, in the ability of the NMD polypeptide to reduce toxicity of a cell, e.g., a neuronal cell, expressing TDP-43 and/or FUS.

Agents and test agents to be used in the methods described herein include crude or partially or substantially purified extracts of organic sources, e.g., botanical (e.g., herbal) and algal extracts, inorganic elements or compounds, as well as partially or substantially purified or synthetic agents, e.g., small molecules, polypeptides, antibodies, and polynucleotides, and libraries of these.

In one example, combinatorial chemical libraries can be produced or obtained that sample chemical compounds that are structurally or chemically related or unrelated. Preparation and screening of combinatorial chemical libraries is well known to those of skill in the art. Such combinatorial chemical libraries include, but are not limited to, peptide libraries (see, e.g., U.S. Pat. No. 5,010,175; Furka, Int. J. Pept. Prot. Res. 37:487-493 (1991); and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries, peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), and small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

The invention is further illustrated by the following examples. The examples are provided for illustrative purposes only. They are not to be construed as limiting the scope or content of the invention in any way.

EXAMPLES

Example 1

Expression of UPF1 In Neurons Eliminates Toxicity of FUS or TDP-43

The present Example describes reduction of TDP-43 or FUS-mediated neuronal toxicity by UPF1.

A yeast model of ALS was used to identify a human gene, UPF1, which suppressed toxicity of FUS/TLS in yeast (Ju et al., PLoS Biol. 9:e1001052 (2011)). Further, UPF1 was able to suppress the cytotoxicity of ALS-associated TDP-43 mutations in yeast as welt.

To test the efficacy of UPF1 in reducing TDP-43 or FUS-mediated cytotoxicity in neurons, UPF1 was expressed in motor neurons expressing disease-associated FUS or TDP-43. Motor neurons were either isolated from mice or created from fibroblasts taken from human ALS patients using iPS cell techniques (described in Yamanaka et al., Cell 126:663-676 (2006)). FUS or TDP-43 were tagged with EGFP (Enhanced Green Fluorescent Protein) and expressed in motor neurons, which were visualized by fluorescent microscopy using mApple.

Figure 1B:
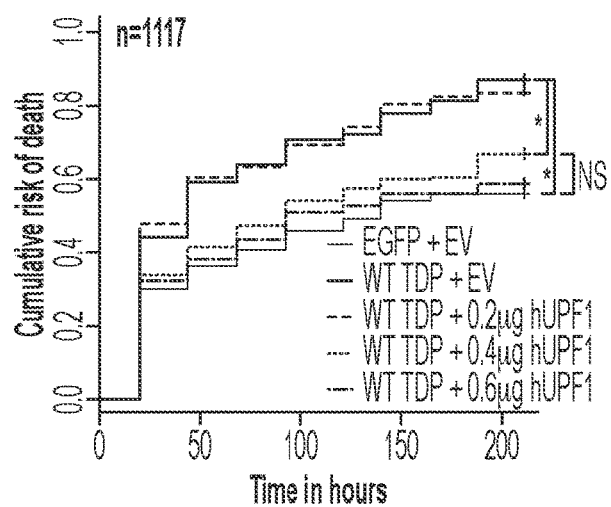
FIG. 1B is a graphical representation of cell death of neurons following expression of TDP-43 and UPF1.

The motor neurons died within a few days of FUS or TDP-43 expression due to toxicity of these ALS-related proteins. UPF1 was expressed in the motor neurons and Kaplan-Meyer survival curves were determined. As shown in FIG. 1A, UPF1 expression had no effect on survival of wild type neurons, indicating that UPF1 was not a generic survival factor. However, as shown in FIG. 1B, UPF1 was able to completely eliminate the toxicity of TDP-43 in a dose-dependent manner. UPF1 had a similar effect on cells expressing FUS (data not shown). Moreover, UPF1 expression was unable to rescue the toxicity of ALS-associated mutants of SOD1, demonstrating for the first time that SOD1-dependent fALS is a distinct disease mechanistically.

Example 2

Yeast Screening Assay for Compounds that Rescue FUS Toxicity

A drug screen based on the yeast model described in Example 1 was developed to identify compounds that rescue toxicity that resulted from FUS expression. Because the phenotype was rescue from cell death, the screen demonstrated exceptionally good signal-to noise, with a Z' score of around 0.8.

Briefly, two yeast strains were engineered: "1XFUS", in which a FUS gene was stably integrated at the HIS locus; and "1XVcc", in which an empty vector was integrated at the same locus. The media used were YPRaffinose and 2XYPGalactose (2× concentrated). Yeast cells were grown by inoculating a single colony of 1XFUS strain or 1XVec strain into 2 ml YPRaffinose medium and were grown overnight at 30° C. The overnight cultures were then used to inoculate 50 ml YPRaffinose medium at OD600=0.2 and were grown for 24 hrs at 30° C.

The cultures were then diluted in 500 ml 2X YPGalactose medium at OD600=0.2. 384 well plates were pre-filled with 25 µl of each test compound at a concentration of 30 µM. A Multidrop was used to add 25 µl of the suspension of 1XFUS to each well on columns 1-23 of the plate; 1XVec was added to each well on column 24 as control. The yeast and compounds were mixed thoroughly. The plates were kept in a humidified incubator at 30° C. The OD600 of each plate was monitored at 24 hr and 48 hrs.

The compound(s) that rescued the growth of 1XFUS were selected and retested. The compounds that passed the retest were further checked in a 10-dose response experiment. The compounds that demonstrated good dose responses were re-ordered, and retested.

Equivalents

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Sequences

UPF1 nucleotide sequence (GenBank Accession No. U59323.1, nt 176-3532)(SEQ ID NO: 1)

```
 176                                                                atgag
 181 cgtggaggcg tacgggccca gctcgcagac tctcactttc ctggacacgg aggaggccga
 241 gctgcttggc gccgacacac agggctccga gttcgagttc accgacttta ctcttcctag
 301 ccagacgcag acgcccccg gcggccccgg cggcccgggc ggtggcggcg cgggaagccc
 361 gggcggcgcg ggcgccggcg ctgcggcggg acagctcgac gcgcaggttg ggcccgaagg
 421 catcctgcag aacgggctg tggacgacag tgtagccaag accagccagt tgttggctga
 481 gttgaacttc gaggaagatg aagaagacac ctattacacg aaggacctcc ccatacacgc
 541 ctgcagttac tgtggaatac acgatcctgc ctgcgtggtt tactgtaata ccagcaagaa
 601 gtggttctgc aacggacgtg gaaatacttc tggcagccac attgtaaatc accttgtgag
 661 ggcaaaatgc aaagaggtga ccctgcacaa ggacgggccc ctggggggaga cagtcctgga
 721 gtgctacaac tgcggctgtc gcaacgtctt cctcctcggc ttcatcccgg ccaaagctga
 781 ctcagtggtg gtgctgctgt gcaggcagcc ctgtgccagc cagagcagcc tcaaggacat
 841 caactgggac agctcgcagt ggcagccgct gatccaggac cgctgcttcc tgtcctggct
 901 ggtcaagatc ccctccgagc aggagcagct gcgggcacgc cagatcacgg cacagcagat
 961 caacaagctg gaggagctgt ggaaggaaaa cccttctgcc acgctggagg acctggagaa
1021 gccgggggtg gacgaggagc cgcagcatgt cctcctgccg tacgaggacg cctaccagta
1081 ccagaacata ttcgggcccc tggtcaagct ggaggccgac tacgacaaga agctgaagga
1141 gtcccagact caagataaca tcactgtcag gtgggacctg ggccttaaca agaagagaat
1201 cgcctacttc actttgccca agactgactc tgacatgcgg ctcatgcagg gggatgagat
1261 atgcctgcgg tacaaagggg accttgcgcc cctgtggaaa gggatcgacc acgtcatcaa
1321 ggtccctgat aattatggcg atgagatcgc cattgagctg cggagcagcg tgggtgcacc
1381 tatggaggtg actcacaact tccaggtgga ttttgtgtgg aagtcgacct cctttgacag
1441 gatgcagagc gcattgaaaa cgtttgccgt ggatgagacc tcggtgtctg gctacatcta
1501 ccacaagctg ttgggccacg aggtggagga cgtaatcacc aagtgccagc tgcccaagcg
1561 cttcacggcg cagggcctcc ccgacctcaa ccactcccag gtttatgccg tgaagactgt
1621 gctgcaaaga ccactgagcc tgatccaggg cccgccaggc acggggaaga cggtgacgtc
1681 ggccaccatc gtctaccacc tggcccggca aggcaacggg ccggtgctgg tgtgtgctcc
1741 gagcaacatc gccgtgaacc agctaacgga gaagatccac cagacggggc taaaggtcgt
1801 gcgcctctgc gccaagagcc gtgaggccat cgactccccg gtgtcttttc tggccctgca
1861 caaccagatc aggaacatgg acagcatgcc tgagctgcag aagctgcagc agctgaaaga
1921 cgagactggg gagctgtcgt ctgccgacga gaagcggtac cgggccttga agcgcaccgc
1981 agagagagag ctgctgatga acgcagatgt catctgctgc acatgtgtgg gcgccggtga
2041 cccgaggctg gccaagatgc agttccgctc cattttaatc gacgaaagca cccaggccac
2101 cgagccggag tgcatggttc ccgtggtcct cggggccaag cagctgatcc ttgtaggcga
2161 ccactgccag ctgggcccag tggtgatgtg caagaaggcg gccaaggccg ggctgtcaca
2221 gtcgctcttc gagcgcctgg tggtgctggg catccggccc atccgcctgc aggtccagta
2281 ccggatgcac cctgcactca gcgccttccc atccaacatc ttctacgagg gctccctcca
2341 gaatggtgtc actgcagcgg atcgtgtgaa gaagggatttt gacttccagt ggccccaacc
2401 cgataaaccg atgttcttct acgtgaccca gggccaagag gagattgcca gctcgggcac
2461 ctcctacctg aacaggaccg aggctgcgaa cgtggagaag atcaccacga agttgctgaa
2521 ggcaggcgcc aagccggacc agattggcat catcacgccc tacgagggcc agcgctccta
2581 cctggtgcag tacatgcagt tcagcgctc cctgcacacc aagctctacc aggaagtgga
2641 gatcgccagt gtggacgcct ttcagggacg cgagaaggac ttcatcatcc tgtcctgtgt
2701 gcgggccaac gagcaccaag gcattggctt tttaaatgac cccaggcgtc tgaacgtggc
2761 cctgaccaga gcaaggtatg gcgtcatcat tgtgggcaac ccgaaggcac tatcaaagca
2821 gccgctctgg aaccacctgc tgaactacta taggagcag aaggtgctgg tggaggggcc
2881 gctcaacaac ctgcgtgaga gcctcatgca gttcagcaag ccacggaagc tggtcaacac
```

-continued

| Sequences |
|---|

```
     2941 tatcaacccg ggagcccgct tcatgaccac agccatgtat gatgcccggg aggccatcat
     3001 cccaggctcc gtctatgatc ggagcagcca gggccggcct tccagcatgt acttccagac
     3061 ccatgaccag attggcatga tcagtgccgg ccctagccac gtggctgcca tgaacattcc
     3121 catcccttc aacctggtca tgccaccat gccaccgcct ggctattttg acaagccaa
     3181 cgggcctgct gcagggcgag gcaccccgaa aggcaagact ggtcgtgggg gacgccagaa
     3241 gaaccgcttt gggcttcctg gacccagcca gactaacctc ccaacagcc aagccagcca
     3301 gaatgtggcg tcacagccct tctctcaggg cgccctgacg cagggctaca tctccatgag
     3361 ccagccttcc cagatgagcc agcccggcct ctcccagccg gagctgtccc aggacagtta
     3421 ccttggtgac gagtttaaat cacaaatcga cgtggcgctc tcacaggact ccacgtacca
     3481 gggagagcgg gcttaccagc atggcggggt gacggggctg tcccagtatt aa
```

UPF1 amino acid sequence (GenBank Accession No. AAC51140.)(SEQ ID NO: 2)

```
        1 msveaygpss qtltfldtee aellgadtqg sefeftdftl psqtqtppgg pggpggggag
       61 spggagagaa agqldaqvgp egilqngavd dsvaktsqll aelnfeedee dtyytkdlpi
      121 hacsycgihd pacvvycnts kkwfcngrgn tsgshivnhl vrakckevtl hkdgplgetv
      181 lecyncgcrn vfllgfipak adsvvvllcr qpcasqsslk dinwdssqwq pliqdrcfls
      211 wlvkipseqe qlrarqitaq qinkleelwk enpsatledl ekpgvdeepq hvllryeday
      301 qyqnifgplv kleadydkkl kesqtqdnit vrwdlglnkk riayftlpkt dsdmrlmqqd
      361 eiclrykgdl aplwkgighv ikvpdnygde iaielrssvg apvevthnfq vdfvwkstsf
      421 drmqsalktf avdetsysgy iyhkllghev edvitkcqlp krftaqglpd lnhsqvyavk
      481 tvlqrplsli qgppgtgktv tsativyhla rqgngpvlvc apsniavdql tekihqtglk
      541 vvrlcaksre aidspvsfla lhnqirnmds mpelqklqql kdetgelssa dekryralkr
      601 taerellmna dviccctcvga gdprlakmqf rsilidestq atepecmvpv vlgakqlilv
      661 gdhcqlgpvv mckkaakagl sqslferlvv lgirpirlqv qyrmhpalsa fpsnifyegs
      721 lqngvtaadr vkkgfdfqwp qpdkpmffyv tqgqeeiass gtsylnrtea anvekittkl
      781 lkagakpdqi giitpyeqgqr sylvqymqfs gslhtklyqe veiasvdafq grekdfiils
      841 cvranehqgi gflndprrln valtrarygv iivgnpkals kqplwnhlln yykeqkvlve
      901 gplnnlresl mqfskprklv ntinpgarfm ttamydarea iipgsvydrs sqgrpssmyf
      961 qthdqigmis agpshvaamn ipipfnlvmp pmpppgyfgq angpaagrgt pkgktgrggr
     1021 qknrfglpgp sqtnlpnsqa sqdvasqpfs qgaltqgyis msqpsqmsqp glsqpelsqd
     1081 sylgdefksq idvalsqdst yqgerayqhg gvtglsqy
```

UPF2 nucleotide sequence (GenBank Accession No. AF318574.1)(nt 76-3894)(SEQ ID NO: 3)

```
       76            atgcc agctgagcgt aaaaagccag caagtatgga agaaaaagac
      121 tctttaccaa acaacaagga aaaagactgc agtgaaaggc ggacagtgag cagcaaggag
      181 aggccaaaag acgatatcaa gctcactgcc aagaaggagg tcagcaaggc ccctgaagac
      211 aagaagaaga gactggaaga tgataagaga aaaaagaacg acaaggaacg caagaaaaaa
      301 gacgaagaaa aggtgaaggc agaggaagaa tcaaagaaaa aagaagagga agaaaaaaag
      361 aaacatcaag aggaagagag aaagaagcaa gaagagcagg ccaaacgtca gcaagaagaa
      421 gaagcagctg ctcagatgaa agaaaaagaa gaatccattc agcttcatca ggaagcttgg
      481 gaacgacatc atttaaggaa ggaacttcgt agcaaaaaac aaaatgcctc gacagccga
      541 ccagaggaaa acttcttcag ccgcctcgac tcaagtttga agaaaaatac tgcttttgtc
      601 aagaaactaa aaactattac agaacaacag agagactcct gtcccatga ttttaatggc
      661 ctaaatttaa gcaaatacat tgcagaagct gtagcttcca tcgtggaagc aaaactaaaa
      721 atctctgatg tgaactgtgc tgtgcacctc tgctctctgt ttcaccacg ttatgctgac
      781 tttgccccat cacttcttca ggtctggaaa aacattttg aagcaaggaa agaggagaaa
      841 acacctaaca tcaccaagtt aagaactgat ttgcgttta ttgcagaatt gacaatagtt
      901 gggatttca ctgacaagga aggtcttttcc ttaatctatg aacagctaaa aatatattatt
      961 aatgctgatc gggagtccca cactcatgtc tctgtagtga ttagtttctg tgacattgt
     1021 ggagatgata ttgctggact tgtaccaagg aaagtaaaga gtgctgcaga aagtttaat
     1081 ttgagttttc ctcctagtga gataattagt ccagagaaac aacagccctt ccagaatctt
     1141 ttaaaagagt actttacgtt tttgaccaaa cacctgaaaa gggaccacag ggagctccag
     1201 aatactgaga gacaaaacag gcgcattcta cattctaagg gggagctcag tgaagataga
     1261 cataaacagt atgaggaatt tgctatgtct taccagaagc tgctggcaaa ttctcaatcc
     1321 ttagcagacc ttttggatga aatatgcca gatcttcctc aagacaaacc cacaccagaa
     1381 gaacatgggc ctggaattga tatattcaca cctggtaaac ctggagaata tgacttggaa
     1441 ggtggtatat gggaagatga agatgctcgg aattttttag agaacctcat tgatttggag
     1501 gcttttgtcc cagccatctt gtttaaagac aatgaaaaaa gttgtcagaa taaagagtcc
     1561 aacaaagatg ataccaaaga ggcaaaagaa tctaaggaga ataaggaggt atcaagtccc
     1621 gatgatttgg aacttgagtt ggagaatcta gaaattaatg atgcaccctt agaattagag
     1681 ggtggagatg aagctgaaga tcttacaaag aaacttcttg atgaacaaga acaagaagat
     1741 gaggaagcca cgcactggatc tcatcctcaag ctcatagtag atgcttttcct acagcagtta
     1801 cccaactgtg tcaaccgaga tctgatagac aaggcagcaa tggattttg catgaacatg
     1861 aacacaaaag caaacaggaa gaagttggta cggcactct tcatagttcc tagacaaagg
     1921 ttggatttgc taccatttta tgcaagattg gttgctacat gcatccctg catgtctgat
     1981 gtagcagagg atctttgttc catgctgagg ggggatttca gatttcatgt acggaaaggga
     2041 gaccagatca atattgaaac aaagaataaa actgttcgtt ttataggaga actaactaag
     2101 tttaagatgt tcaccaaaaa tgcacactg cattgttaa agatgcttct atcagacttc
     2161 tctcatcacc atattgaaat ggcatgcacc ctgctggaga catgtggacg gtttcttttc
     2221 aaatctccag aatctcacct gaggaccagt gtactttgg agcaaatgat gagaaagaag
     2281 caagcaatgc atcttgatgc gagatacgtc acaatggtag agaatgcata ttactactgc
     2341 aacccacctc cagctgaaaa aaccgtgaaa aagaaacatc ctcctctcca agaatatgtc
     2101 cagaaacttt tgtacaaaga tctctctaag gttaccaccg agaaggtttt gagacagatg
     2461 caaaagctgc cctggcagga ccaagaagtg aaagactatg ttatttgttg tatgataaac
     2521 atctggaatg tgaaatataa tagtattcat tgtgtagcca acctcttagc aggactagtg
     2581 ctctaccaag aggatgttgg gatccacgtt gtggatggag tgttagaaga tattcgatta
     2641 gaaatggagg ttaatcaacc taaatttaat cagaggcgca tcagcagtgc caagttctta
```

```
                              Sequences
2701  gaagaacttt acaattaccg aatggtggaa tcagctgtta ttttcagaac tctgtattct
2761  tttacctcat ttggtgttaa tcctgatggc tctccaagtt ccctggaccc acctgagcat
2821  cttttcagaa ttagactcgt atgcactatt ctggacacat gtggccagta cttttgacaga
2881  ggttccagta aacgaaaact tgattgtttc cttgtatatt ttccacgtta tgtttggtgg
2941  aagaaaagtt tggaggtttg gacaaaagac catccatttc ctattgatat agattacatg
3001  atcagtgata cactagaact gctaagacca aagatcaaac tctgtaattc tctggaagaa
3061  tccatcaggc aggtacaaga cttggaacga gaattcttaa taaaactagg cctagtaaat
3121  gacaaagact caaaagattc tatgcagaa ggagaaaatc ttgaagagga tgaagaagaa
3181  gaagaaggtg gggctgaaac agaagaacaa tctgaaatg aaagtgaagt aaatgagcca
3241  gaagaagagg agggttctga taatgatgat gatgagggag aagaagagga ggaagagaat
3301  acagattacc ttacagattc caataaggaa aatgaaaccg atgaagagaa tactgaggta
3361  atgattaaag gcggtggact taagcatgta cctttgtgtg aagatgagga cttcattcaa
3421  gctctggata aaatgatgct agaaaatcta cagcaacgaa gtggtgaatc tgttaaagtg
3481  caccaactag atgtggccat tcctttgcat ctcaaaagcc agctgaggaa agggccccca
3541  ctgggaggtg gggaaggaga ggctgagtct gcagacacaa tgccgtttgt catgttaaca
3601  agaaaaggca ataaacagca gtttaagatc cttaatgtac ccatgtcctc tcaacttgct
3661  gcaaatcact ggaaccagca acaggcagaa caagaagaga ggatgagaat gaagaagctc
3721  acactagata tcaatgaacg gcaagaacaa gaagattatc aagaaatgtt gcagtctctt
3781  gcacagcgcc cagctccagc aaacaccaat cgtgagaggc ggcctcgcta ccaacatccg
3841  aagggagcac ctaatgcaga tctaatcttt aagactggtg ggaggagacg ttga UPF2 amino acid sequence (GenBank Accession No. AAG60689.1)(SEQ ID NO: 4)
   1  mpaerkkpas meekdslpnn kekdcserrt vsskerpkdd iklttakkevs kapedkkkrl
  61  eddkrkkedk erkkkdeekv kaeeeskkke eeekkkhqee erkkqeeqak rqqeeeaaaq
 121  mkekeesiql hqeawerhhl rkelrsknqn apdsrpeenf fsrldsslkk ntafvkklkt
 181  iteqqrdsls hdfnglnlsk yiaeavasiv eaklkisdvn cavhlcslfh qryadfapsl
 241  lqvwkkhfea rkeektpnit klrtdlrfia eltivgiftd keglsliyeq lkniinadre
 301  shthvsvvis fcrhcgddia glvprkvksa aekfnlsfpp seiispekqq pfqnllkeyf
 361  tsltkhlkrd hrelqnterq nrrilhskge lsedrhkqye efamsyqkll ansqsladll
 421  denmpdlpqd kptpeehgpg idiftpgkpg eydleggiwe dedarnfyen lidlkafvpa
 481  ilfkdneksc qnkesnkddt keakeskenk evsspddlel elenleindd tleleggdea
 541  edltkkllde qeqedeeast gshlklivda flqqlpncvn rdlidkaamd fcmnmntkan
 601  rkklvralfi vprqrldllp fyarlvatlh pcmsdvaedl csmlrgdfrf hvrkkdqini
 661  etknktvrfi geltkfkmft kndtlhclkm llsdfshhhi emactlletc grflfrspes
 721  hlrtsvlleq mmrkkqamhl daryvtmven ayyycnpppa ektvkkkrpp lqeyvrklly
 781  kdlskvttek vlrqmrklpw qdqevkdyvi ccminiwnvk ynsihcvanl laglvlyqed
 841  vgihvvdgvl edirlgmevn qpkfnqrris sakflgelyn yrmvesavif rtlysftsfg
 901  vnpdgspssl dppehlfrir lvctildtcg qyfdrgsskr kldcflvyfq ryvwwkksle
 961  vwtkdhpfpi didymisdtl ellrpkiklc nsleesirqv qdlereflik lglvndkdsk
1021  dsmtegenle edeeeeegga eteeqsgnes evnepeeeeg sdndddegee eeeentdylt
1081  dsnkenetde entevmikgg glkhvpcved edfiqaldkm mlenlqqrsg esvkvhqldv
1141  aiplhlksql rkgpplggge geaesadtmp fvmltrkgnk qqfkilnvpm ssqlaanhwn
1201  qqqaeqeerm rmkkltldin erqeqedyqe mlqslaqrpa pantnrerrp ryqhpkgapn
1261  adlifktggr rr UPF3 nucleotide sequence (GenBank Accession No. AF318575_1)(nt 22-1380)(SEQ ID NO: 5)
  22                       atgctgtcg gcccctagaag tgcagttcca ccgcgactcg
  61  cagcagcagg aggctgagac gccgccaact tcgtcctccg gttgcggggg cggtgcgggc
 121  aaacctcgcg aggagaagag gacggccctg agcaaggtgg tcatccgccg cctgcctccg
 181  ggcctcacca aggagcagct ggaggagcag ctgcgcccgc tgccagcaca cgactacttc
 241  gagttcttcg ccgccgacct gagtctttat cctcatctct actcaagagc atacattaat
 301  tttaggaatc ctgatgacat ccttcttttt agagatcgtt ttgatggata tatcttcctt
 361  gacagcaaag gcctagaata tcctgcagtg gtagagtttg ctccattcca gaagatagcc
 421  aaaaagaagc tgagaaaaaa agatgccaag actgcaagaaca tcgaagatga tccagaatat
 481  aagaagtttt tagaaaccta ctgtgtggag gaagagaaga ccagtgccaa ccctgagact
 541  ctgctggggg agatggaggc gaagacaaga gagctcattg ctagaagaac cacacctctt
 601  ttggaatata ttaaaaatag aaaattagaa aagcagaaa ttcgagaaga aagcgaagaa
 661  gaacggagga ggagagagtt agaaaagaaa cgtttgcggg aagaggaaaa aagaagaaga
 721  agagaagaag aaagatgcaa aaaaaagag acagataaac agaagaaaat tgcagagaaa
 781  gaagtaagga ttaagcttct taagaaacca gaaaaggggag gaaccaac cacagagaaa
 841  ccaaaagaaa gaggagagga gattgatact ggaggtggca agcaggaatc ctgtgccccc
 901  ggtgcagtcg taaaagccag gcccatggaa ggctcgctgg aggagcccca ggagacgtca
 961  cacagcggca gtgataaaga gcacagggat gtggagagat ctcaagacaa agaatctgaa
1021  gcacaaagat accatgtgga tgacgcagg aggcacagag ctcaccacga gcctgaacgg
1081  cttttccgaa gggagtgagga tgagcagaga tggggaaag gacctggcca agacagaggg
1141  aagaagggga gccaggacag cggggctccg ggggaggcca tggagagact gggaagagcg
1201  caaaggtgtg acgacagtcg agcacccaga aaagagcgac tggcaaacaa gaccggcca
1261  gccttgcagc tgtatgatcc aggagctcgc ttccgagcgc gagagtgtgg cggaaacagg
1321  aagatctgca aggcagaagg ttcggggact ggtcctgaga gagggaaga ggcagagtga UPF3 amino acid sequence (GenBank Accession No. AAG60690.1)(SEQ ID NO: 6)
   1  mlsalevqfh rdsqqqeaet pptsssgcgg gagkpreekr talskvvirr lppgltkeql
  61  eeqlrplpah dyfeffaadl slyphlysra yinfrnpddi llfrdrfdgy ifldskgley
 121  pavvefapfq kiakkklrkk daktgsiedd peykkflety cveeektsan petllgemea
 181  ktreliarrt tplleyiknr klekqriree kreerrrrel ekkrlreeek rrrreeerck
 241  kketdkqkki aekevrikll kkpekgeept tekpkergee idtgggkqes capgavvkar
 301  pmegsleepq etshsgsdke hrdversqeq eseaqryhvd dgrrhrahhe perlsrrsed
```

| Sequences |
|---|
| 361 eqrwgkgpgq drgkkgsqds gapgeamerl graqrcddsp aprkerlank drpalqlydp
421 garfrarecg gnrrickaeg sgtgpekree ae |

SMG1 nucleotide sequence (GenBank Accession No. NM_015092.4, nt 364-11349)(SEQ ID NO: 7)

```
 364     atgagcc gcagagcccc ggggtctcgg ctgagcagcg gcggcggcgg cggcggcacc
 421 aagtatccgc ggagctggaa tgactggcaa cccagaactg atagtgcatc agccgaccca
 481 gataatttaa aatattcttc atccagagat agaggtggtt cttcctctta tggactgcaa
 541 ccttcaaatt cagctgtggt gtctcggcaa aggcacgatg ataccagagt ccacgctgac
 601 atacagaatg acgaaaaggg tggctacagt gtcaatggag gatctgggga aaatacttat
 661 ggtcggaagt cgttggggca agagctgagg gttaacaatg tgaccagccc tgagttcacc
 721 agtgttcagc atggcagtcg tgctttagcc accaaagaca tgaggaaatc acaggagaga
 781 tcgatgtctt attctgatga gtctcgactg tcaatcttc ttcggaggat cacccgggaa
 841 gacgacagag accgaagatt ggctactgta aagcagttga agaatttat tcagcaacca
 901 gaaaataagc tggtactagt taaacaattg gataatatct tggctgctgt acatgacgtg
 961 cttaatgaaa gtagcaaatt gcttcaggag ttgagacagg agggagcttg ctgtcttggc
1021 cttctttgtg cttctctgag ctatgaggct gagaagatct tcaagtggat ttttagcaaa
1081 tttagctcat ctgcaaaaga tgaagttaaa ctcctctact tatgtgccac ctacaaagca
1141 ctagagactg taggagaaaa gaaagccttt tcatctgtaa tgcagcttgt aatgaccagc
1201 ctgcagtcta ttcttgaaaa tgtggataca ccagaattgc tttgtaaatg tgttaagtgc
1261 attctttttgg tggctcgatg ttaccctcat attttcagca ctaattttag ggatacagtt
1321 gatatattag ttggatggca tatagatcat actcagaaac cttcgctcac gcagcaggta
1381 tctggtggt tgcagagttt ggagccattt tgggtagctg atcttgcatt ttctactact
1441 cttcttggtc agtttctgga agacatggaa gatatgctg aggacctcag ccatgtggcc
1501 tctggggaat cagtggatga agatgtccct cctccatcag tgtcattacc aaagctggcc
1561 gcacttctcc gggtatttag tactgtggtg aggagcattg gggaacgctt cagcccaatt
1621 cggggtcctc caattactga ggcatatgta acagatgttc tgtacagagt aatgagatgt
1681 gtgacggctg caaaccaggt gttttttct gaggctgtgt tgacagctgc taatgagtgt
1741 gttggtgttt tgctcggcag cttggatcct agcatgacta tacattgtga catggtcatt
1801 acatatggat tagaccaact ggagaattgc cagacttgtg gtaccgatta tatcatctca
1861 gtcttgaatt tactcacgct gattgttgaa cagataaata cgaaactgcc atcatcattt
1921 gtagaaaaac tgtttatacc atcatctaaa ctactattct tgcgttatca taagaaaaa
1981 gaggttgttg ctgtagccca tgctgtttat caagcagtgc tcagcttgaa gaatattcct
2041 gtttttggaga ctgcctataa gttaatattg ggagaaatga cttgtgccct aaacaacctc
2101 ctacacagtc tacaacttcc tgaggcctgt tctgaaataa aacatgaggc ttttaagaat
2161 catgtgttca atgtagacaa tgcaaaattt gtagttatat ttgacctcag tgccctgact
2221 acaattggaa atgccaaaaa ctcactaata gggatgtggg cgctatctcc aactgtcttt
2281 gcacttctga gtaagaatct gatgattgtg cacagtgacc tggctgttca cttccctgcc
2341 attcagtatg ctgtgctcta cacattgtat tctcattgta ccaggcatga tcactttatc
2401 tctagtagcc tcagttcttc ctctccttct ttgtttgatg gagctgtgat tagcactgta
2461 actacggcta caaagaaaca tttctcaatt atattaagt ttctgggaat attacttaag
2521 aaagataacc ttaaccagga cacgaggaaa ctgttaatga cttgggcttt ggaagcagct
2581 gttttaatga agaagtctga aacatacgca cctttattct ctcttccgtc tttccataaa
2641 ttttgcaaag gccttttagc caacactctc gttgaagatg tgaatatctg tctgcaggca
2701 tgcagcagtc tacatgctct gtcctcttcc ttgccagatg atcttttaca gagatgtgtc
2761 gatgtttgcc gtgttcaact agtgcacagt ggaactcgta ttcgacaagc atttggaaaa
2821 ctgttgaaat caattccttt agatgttgtc taagcaata acaatcacac agaaattcaa
2881 gaaatttctt tagcattaag aagtcacatg agtaaagcac caagtaaatac attccacccc
2941 caagatttct ctgatgttat tagttttatt ttgtatggga actctcatag aacagggaag
3001 gacaattggt tggaaagact gttctatagc tgccagagac tggataagcg tgaccagtca
3061 acaattccac gcaatctcct gaagacagat gctgtccttt ggcagtgggc catatgggaa
3121 gctgcacaat tcactgttct ttctaagctg agaacccac tgggcagagc tcaagacacc
3181 ttccagacaa ttgaaggtat cattcgaagt ctcgcagctc acacattaaa ccctgatcag
3241 gatgttagtc agtggacaac tgcagacaat gatgaaggcc atggtaacaa ccaacttaga
3301 cttgttcttc ttctgcagta tctggaaaat ctggagaaat taatgtataa tgcatacgag
3361 ggatgtgcta atgcattaac ttcacctccc aaggtcatta gaactttttt ctataccaat
3421 cgccaaactt gtcaggactg gctaacgcgg attcgactct ccatcatgag ggtaggattg
3481 ttggcaggcc agcctgcagt gacagtgaga catggctttg acttgcttac agagatgaaa
3541 acaaccagcc tatctcaggg gaatgaattg gaagtaacca ttatgatggt ggtagaagca
3601 ttatgtgaac ttcattgtcc tgaagctata cagggaattg ctgtctggtc atcatctatt
3661 gttggaaaaa atcttctgtg gattaactca gtggctcaac aggctgaagg gaggtttgaa
3721 aaggcctctg tggagtacca ggaacacctg tgtgccatga caggtgttga ttgctgcatca
3781 tccagcttg acaaatcggt gctcacctta gccaatgctg ggcgtaacag tgccagcccg
3841 aaacattctc tgaatggtga atccagaaaa actgtgctgt ccaaaccgac tgactcttcc
3901 cctgaggtta taattattt aggaaataaa gcatgtgagt gctacatctc aattgccgat
3961 tgggctgctg tgcaggaatg gcagaacgct atccatgact tgaaaaagag taccagtagc
4021 acttccctca acctgaaagc tgacttcaac tatataaaat cattaagcag ctttgagtct
4081 ggaaaatttg ttgaatgtac cgagcagtta gaattgttac caggagaaaa tatcaatcta
4141 cttgctggag gatcaaaaga aaaaatagac atgaaaaaac tgcttcctaa catgttaagt
4201 ccggatccga gggaacttca gaaatccatt gaagttcaat tgttaagaag ttctgtttgt
4261 ttggcaactg ctttaaaccc gatagaacaa gatcagaagt ggcagtctat aactgaaaat
4321 gtggtaaagt acttgaatga aacatcccgc gtgctattg gacctctgag acttttctact
4381 ttaacagttt cacagtcttt gccagttcta agtaccttgc agctgtattg ctcatctgct
4441 ttggagaaca cagtttctaa cagactttca acagaggact gtcttattcc actcttcagt
4501 gaagcttac gttcatgtaa acagcatgac gtgaggccat ggatgcaggc attaaggtat
4561 actatgtacc agaatcagtt gttggagaaa attaagaac aaacagtccc aattagaagc
4621 catctcatgg aattaggtct aacagcagca aaatttgcta gaaaacgagg gaatgtgtcc
```

| | |
|---|---|
| | -continued |
| | Sequences |

```
4681 cttgcaacaa gactgctggc acagtgcagt gaagttcagc tgggaaagac caccactgca
4741 caggatttag tccaacattt taaaaaacta tcaacccaag gtcaagtgga tgaaaaatgg
4801 gggcccgaac ttgatattga aaaaaccaaa ttgctttata cagcaggcca gtcaacacat
4861 gcaatggaaa tgttgagttc ttgtgccata tctttctgca agtctgtgaa agctgaatat
4921 gcagttgcta aatcaattct gacactggct aaatggatcc aggcagaatg gaaagagatt
4981 tcaggacagc tgaaacaggt ttacagagct cagcaccaac agaacttcac aggtctttct
5041 actttgtcta aaaacatact cactctaata gaactgccat ctgttaatac gatggaagaa
5101 gagtatcctc ggatcgagag tgaatctaca gtgcatattg gagttggaga acctgacttc
5161 attttgggac agttgtatca cctgtcttca gtacaggcac ctgaagtagc caaatcttgg
5221 gcagcgttgg ccagctgggc ttataggtgg ggcagaaagg tggttgacaa tgccagtcag
5281 ggagaaggtg ttcgtctgct gcctagagaa aaatctgaag ttcagaatct acttccagac
5341 actataactg aggaagagaa agagagaata tatggtattc ttggacaggc tgtgtgtcgg
5401 ccggcgggga ttcaggatga agatataaca cttcagataa ctgagagtga agacaacgaa
5461 gaagatgaca tggttgatgt tatctagcgt cagttgatat caagctgccc atggctttca
5521 gaacttgatg aaagtgcaac tgaaggagtt attaaagtgt ggaggaaagt tgtagataga
5581 atattcagcc tgtacaaact ctcttacagt gcatacttta ctttccttaa actcaacgct
5641 ggtcaaattc ctttagatga ggatgaccct aggctgcatt taagtcacag agtggaacag
5701 agcactgatg acatgattgt gatggccaca ttgcgcctgc tgcggttgct cgtgaagcat
5761 gctggtgagc ttcggcagta tctggagcac ggcttggaga caacacccac tgcaccatgg
5821 agaggaatta ttccgcaact tttctcacgc ttaaaccacc ctgaagtgta tgtgcgccaa
5881 agtatttgta accttctctg ccgtgtggct caagattccc cacatctcat attgtatcct
5941 gcaatagtgg gtaccatatc gcttagtagt gaatcccagg cttcaggaaa taaattttcc
6001 actgcaattc caactttact tggcaatatt caaggagaag aattgctggt ttctgaatgt
6061 gagggaggaa gtcctcctgc atctcaggat gcaataagg atgaacctaa aagtggatta
6121 aatgaagacc aagccgatga gcaggattgt tacagcaaaa ttgtagataa gctgtcctct
6181 gcaaaccca ccatggtatt acaggttcag atgctcgtgg ctgaactgcg cagggtcact
6241 gtgctctggg atgagctctg gctggaagtt ttgctgcaac aacacatga tgtcctgaga
6301 cgaattcagc agcttgaaga tgaggtgaag agagtccaga acaacaacac cttacgcaaa
6361 gaagagaaaa ttgcaatcat gagggagaag cacacagctt tgatgaagcc catcgtattt
6421 gctttggagc atgtgaggag tatcacagcg gctcctgcag aaacacctca tgaaaaatgg
6481 tttcaggata actatggtga tgccattgaa aatgccctag aaaaactgaa gactccattg
6541 aaccctgcaa agcctgggag cagctggatt ccatttaaag agataatgct aagtttgcaa
6601 cagagagcac agaaacgtgc aagttacatc ttgcgtcttg aagaaatcag tccatggttg
6661 gctgccatga ctaacactga aattgctctt cctggggaag tctcagccag agacactgtc
6721 acaatccata gtgtgggcgg aaccatcaca atcttaccga ctaaaaccaa gccaaagaaa
6781 cttctctttc ttggatcaga taggaagagc tatccttatc ttttcaaagg actggaggat
6841 ttacatctgg atgagagaat aatgcagttc ctatctattg tgaataccat gtttgctaca
6901 attaatcgcc aagaaacacc ccggttccat gctcgacact attctgtaac accactagga
6961 acaagatcag gactaatcca gtgggtagat ggagccacac ccttatttgg tctttacaaa
7021 cgatggcaac aacgggaagc tgccttacaa gcacaaaagg cccaagattc ctaccaaact
7081 cctcagaatc ctggaattgt accccgtcct gttgaacttt attacagtaa aattggccct
7141 gctttgaaaa cagttgggct tagcctggat gtgtcccgtc gggattggcc tcttcatgta
7201 atgaaggcag tattggaaga gttaatggag ccacaccccc gaatctcct tgccaaagag
7261 ctctggtcat cttgcacaac acctgatgaa tggtggagag ttacgcagtc ttatgcaaga
7321 tctactgcag tcatgtctat ggttggatac ataattggcc ttggagacag acatctggat
7381 aatgttctta tagatatgac gactgaagaa gttgttcaca tagattacaa tgtttgcttt
7441 gaaaaaggta aaagccttag agttcctgag aaagtacctt ttcgaatgac acaaaacatt
7501 gaaacagcac tgggtgtaac tggagtagaa ggtgtattta ggctttcatg tgagcaggtt
7561 ttacacatta tgcggcgtgg cagagagacc ctgctgacgc tgctggagtc tgcttggtac
7621 gaccctctgg tggactggac agcaggaggc gaggctgggt ttgctggtgc tgtctatgac
7681 ggaggtgcc agcaggccga gagcaagcag agcaagagag atgagcg agagatcacc
7741 cgcagcctgt tttcttctag agtagctgag attaaggtga actggtttaa gaatagagat
7801 gagatgctgg ttgtgcttcc caagttggac ggtagcttag atgaatacct aagcttgcaa
7861 gagcaactga cagatgtgga aaaactgcag ggcaaactac tggaggaaat agagtttcta
7921 gaaggagctg aaggggtgga tcatccttct catactctgc aacacaggta ttctgagcac
7981 acccaactac agactcagca aagagctgtt caggaagcaa tccaggtgaa gctgaatgaa
8041 tttgaacaat ggataacaca ttatcaggct gcattcaata atttagaagc aacacagctt
8101 gcaagcttgc ttcaagagat aagcacacaa atggaccttg gtcctccaag ttacgtgcca
8161 gcaacagcct ttctgcagaa tgctggtcag gcccacttga ttagccagtg cgagcagctg
8221 gaggggagg ttggtgctct cctgcagcag aggcgctccg tgctccgtgg ctgtctggag
8281 caactgcatc actatgcaac cgtggccctg cagtatccga aggccatatt tcagaaacat
8341 cgaattgaac agtgaagac ctggatggaa agctcatct gtaaccacac agtagagcgt
8401 tgtcaagagc tctataggaa atatgaaatg caatatgctc cccagccacc cccaacagtg
8461 tgtcagttca tcactgccac tgaaatgacc ctgcagcgat acgcagcaga catcaacagc
8521 agacttatta dacaagtgga acgcttgaaa caggaagctg tcactgtgcc agtttgtgaa
8581 gatcagttga aagaaattga acgttacatt aaagttttcc ttcatgagaa tggagaagaa
8641 ggatctttga gtctagcaag tgttattatt tctgcccttt gtacccttac aaggcgtaac
8701 ctgatgatgg aaggtgcagc gtcaaatgct ggagaacagc tggttgatct gacttctcgg
8761 gatggagcct ggttcttgga ggaactctgc agtatgagcg gaaacgtcac ctgcttggtt
8821 cagttactga agcagtgcca cctggtgcca caggacttag atatcccgaa ccccatggaa
8881 gcgtctgaga cagttcactt agccaatgga gtgtatacct cacttcagga attgaattcg
8941 aatttccggc aaatcatatt tccagaaagca cttcagtggt taatgaaagg ggaatacacg
9001 ttagaaagta tgctgcatga actggacggt cttattgagc agaccaccga tggcgttccc
9061 ctgcagactc tagtggaatc tcttcaggcc tacttaagaa acgcagctat gggactggaa
9121 gaagaaacac atgctcatta catcgatgtt gccagactac tacatgctca gtacggtgaa
9181 ttaatccaac cgagaaatgg ttcagttgat gaaacaccca aaatgtcagc tggccagatg
9241 cttttggtag cattcgatgg catgtttgct caagttgaaa ctgctttcag cttattagtt
```

-continued

| | Sequences |
|---|---|
| 9301 | gaaaagttga acaagatgga aattcccata gcttggcgaa agattgacat cataaggdaa |
| 9361 | gccaggagta ctcaagttaa ttttttttgat gatgataatc accggcaggt gctagaagag |
| 9421 | attttctttc taaaaagact acagactatt aaggagttct tcaggctctg tggtaccttt |
| 9481 | tctaaaacat tgtcaggatc aagttcactt gaagatcaga atactgtgaa tgggcctgta |
| 9541 | cagattgtca atgtgaaaac ccttttttaga aactcttgtt tcagtgaaga ccaaatggcc |
| 9601 | aaacctatca aggcattcac agctgacttt gtgaggcagc tcttgatagg gctacccaac |
| 9661 | caagccctcg gactcacact gtgcagtttt atcagtgctc tgggtgtaga catcattgct |
| 9721 | caagtagagg caaaggactt tggtgccgaa agcaaagttt ctgttgatga tctctgtaag |
| 9781 | aaagcggtgg aacataacat ccagataggg aagttctctc agctcggttat gaacagggca |
| 9841 | actgtgttag caagttctta cgacactgcc tggaagaagc atgacttggt gcgaaggcta |
| 9901 | gaaaccagta tttcttcttg taagacaagc ctgcagcggg ttcagctgca tattgccatg |
| 9961 | tttcagtggc aacatgaaga tctacttatc aatagaccac aagccatgtc agtcacacct |
| 10021 | cccccacggt ctgctatcct aaccaacatg aaaaagaagc tgcatacct gagccagatt |
| 10081 | gaaacttcta ttgcaacagt tcaggagaag ctagctgcac ttgaatcaag tattgaacag |
| 10141 | cgactcaagt gggcaggtgg tgccaaccct gcattggccc ctgtactaca agattttgaa |
| 10201 | gcaacgatag ctgaaagaag aaatccttgtc cttaaagaga gccaaagagc aagtcaggtc |
| 10261 | acatttctct gcagcaatat cattcatttt gaaagtttac gaacaagaac tgcagaagcc |
| 10321 | ttaaacctgg atgcggcgtt atttgaacta atcaagcgat gtcagcagat gtgttcgttt |
| 10381 | gcatcacagt ttaacagttc agtgtctgag ttagagcttc gtttattaca gagagtggac |
| 10441 | actggtcttg aacatcctat tggcagctct caactgcattt tgtcagccca caaacagttg |
| 10501 | acccaggata tgtctactca gagggcaatt cagacagaga aagagcagca gatagaaacg |
| 10561 | gtctgtgaaa caattcagaa tctggttgat aatataaaga ctgtgctcac tggtcataac |
| 10621 | cgacagcttg agatgtcaa acatctcttg aaagctatgg ctaaggatga agaagctgct |
| 10681 | ctggcagatg gtgaagatgt tccctatgag aacagtgtta ggcagttttt gggtgaatat |
| 10741 | aaatcatggc aagacaacat tcaaacagtt ctatttcact tagtccaggc tatgggtcag |
| 10801 | gttcgaagtc aagaacacgt tgaaatgctc caggaaatca ctcccaccct gaaagaactg |
| 10861 | aaaacacaaa gtcagagtat ctataataat ttagtgagtt ttgcatcacc cttagtcacc |
| 10921 | gatgcaacaa atgaatgttc gagtccaacg tcatctgcta cttatcagcc atccttcgct |
| 10981 | gcagcagtcc ggagtaacac tggccagaag actcagcctg atgtcatgtc acagaatgct |
| 11041 | agaaagctga tccagaaaaaa tcttgctaca tcagctgata ctccaccaag caccgttcca |
| 11101 | ggaactggca agagtgttgc ttgtagtcct aaaaaggcag tcagagaccc taaaactggg |
| 11161 | aaagcggtgc aagagagaaa ctcctatgca gtgagtgtgt ggaagagagt gaaagccaag |
| 11221 | ttagagggcc gagatgttga tccgaataag aggatgtcag ttgctgaaca ggttgactat |
| 11281 | gtcattaagg aagcaactaa tctagataac ttggctcagc tgtatgaagg ttggacagcc |
| 11341 | tgggtgtga | |

SMG1 amino acid sequence (GenBank Accession No. NP_055907.3)(SEQ ID NO: 8)
```
   1 msrrapgsrl ssggggggtk yprswndwqp rtdsasadpd nlkyssssrdr ggsssyglqp
  61 snsavvsrqr hddtrvhadi qndekggysv nggsgentyg rkslgqelry nnvtspefts
 121 vqhgsralat kdmrksqers msysdesrls nllrritred drdrrlatvk qlkefiqqpe
 181 nklvlvkqld nilaavhdvl nesskllqel rqegacclgl lcaslsyeae kifkwifskf
 241 sssakdevkl lylcatykal etvgekkafs svmqlvmtsl qsilenvdtp ellckcvkci
 301 llvarcyphi fstnfrdtvd ilvgwhidht qkpsltqqvs gwlqslepfw vadlafsttl
 361 lgqfledmea yaedlshvas gesvdedvpp psyslpklaa llrvfstvvr sigerfspir
 421 gppiteayvt dvlyrvmrcv taanqvffse avltaanecv gvllgsldps mtihcdmvit
 481 ygldqlencq tcgtdyiisv lnlltliveq intklpssfv eklfipsskl lflryhkeke
 541 vvavahavyq avlslknipv letayklilg emtcalnnll hslqlpeacs eikheafknh
 601 vfnvdnakfv vifdlsaltt ignaknslig mwalsptvfa llsknlmivh sdlavhfpai
 661 qyavlytlys hctrhdhfis sslsssspsl fdgavistvt tatkkhfsii lnllgillkk
 721 dnlnqdtrkl lmtwaleaav lmkksetyap lfslpsfhkf ckgllantlv edvniclqac
 781 sslhalsssl pddllqrcvd vcrvqlvhsg trirqafgkl lksipldvvl snnnhteiqe
 841 islalrshms kapsntfhpq dfsdvisfil ygnshrtgkd nwlerlfysc qrldkrdqst
 901 iprnllktda vlwqwaiwea aqftvlsklr tplgraqdtf qtiegiirsl aahtlnpdqd
 961 vsqwttadnd eghgnnqlrl vllgylenl eklmynayeg canaltsppk virtffytnr
1021 qtcqdwltri rlsimrvgll aqgpavtvrh gfdlltemkt tslsqgnele vtimmvveal
1081 celhcpeaiq giavwsssiv gknllwinsv aqqaegrfek asveyqehlc amtgvdccis
1141 sfdksvltla nagrnsaspk hslngesrkt vlskptdssp evinylgnka cecyisiadw
1201 aavqewqnai hdlkkststst slnlkadfny ikslssfesg kfvecteqle llpgeninll
1261 aggskekidm kkllpnmlsp dprelqksie vqllrssvcl atalnpiegd qkwqsitenv
1321 vkylkqtsri aigplrlstl tvsqslpvls tlqlycssal entvsnrlst edclipfse
1381 alrsckqhdv rpwmqalryt myqnqlleki keqtvpirsh lmelgltaah farkrgnvsl
1441 atrllaqcse vqlgktttaq dlvqhfkkls tqgqvdekwg peldiektkl lytagqstha
1501 memlsscais fcksvkaeya vaksiltlak wiqaewkeis gqlkqvyraq hqqnftglst
1561 lskniltlie lpsvntmeee ypriesestv higvgepdfi lgqlyhlssv qapevakswa
1621 alaswayrwg rkvvdnasqg egvrllprek sevqnlllpdt iteeekeriy gilgqavcrp
1681 agiqdeditl qitesednee ddmvdviwrq lisscpwlse ldesategvi kvwrkvvdri
1741 fslyklscsa yftflklnag qipldeddpr lhlshrveqs tddmivmatl rllrllvkha
1801 gelrqylehg lettptapwr giipqlfsrl nhpevyvrqs icnllcrvaq dsphlilypa
1861 ivgtislsse sqasgnkfst aiptllgniq geellvsece ggsppasqds nkdepksgln
1921 edqammqdcy skivdklssa npmvlqvqm lvaelrrvtv lwdelwlgvl lqqhmyvlrr
1981 iqqledevkr vqnnntlrke ekiaimrekh talmkpivfa lehvrsitaa paetphekwf
2041 qdnygdaien aleklktpln pakpgsswip fkeimlslqq raqkrasyil rleeispwla
2101 amtnteialp gevsardtvt ihsvggtiti lptktkpkkl lflgsdgksy pylfkgledl
2161 hlderimqfl sivntmfati nrqetprfha rhysvtplgt rsgliqvdg atplfglykr
2221 wqqreaalqa qkaqdsyqtp qnpgivprps elyyskigpa lktvglsldv srrdwplhvm
2281 kavleelmea tppnllakel wsscttpdew wrvtqsyars tavmsmvgyi iglgdrhldn
2341 vlidmttgev vhidynvcfe kgkslrvpek vpfrmtqnie talgvtgveg vfrlsceqvl
```

```
                                  Sequences 2401  himrrgretl ltlleafvyd plvdwtagge agfagavygg ggqqaeskqs kremereitr
2461  slfssrvaei kvnwfknrde mlvvlpkldg sldeylslqe qltdveklqg klleeiefle
2521  gaegvdhpsh tlqhryseht qlqtqqravq eaiqvklnef eqwithyqaa fnnleatqla
2581  sllqeistqm dlgppsyvpa taflqnagqa hlisqceqle gevgallqqr rsvlrgcleq
2641  lhhyatvalq ypkaifqkhr ieqwktwmee licnttverc qelyrkyemq yapqpppptvc
2701  qfitatemtl gryaadinsr lirqverlkq eavtvpvced qlkeiercik vflhengeeg
2761  slslasviis alctltrrnl mmegaassag eqlvdltsrd gawfleelcs msgnvtclvq
2821  llkqchlvpq dldipnpmea setvhlangv ytslqelnsn frqiifpeal rclmkgeytl
2881  esmlheldgl ieqttdgvpl qtlveslqay lrnaamglee ethahyidva rllhaqygel
2941  iqprngsvde tpkmsagqml lvafdgmfaq vetafsllve klnkmeipia wrkidiirea
3001  rstqvnffdd dnhrqvleei fflkrlqtik effrlcgtfs ktlsgsssle dqntvngpvq
3061  ivnvktlfrn scfsedqmak pikaftadfv rqlliglpnq algltlcsfi salgvdiiaq
3121  veakdfgaes kvsvddlckk avehniqigk fsqlvmnrat vlassydtaw kkhdlvrrle
3181  tsissckts1 qrvqlhiamf qwqhedllin rpqamsvtpp prsailtsmk kklhtlsqie
3241  tsiatvqekl aalessieqr lkwagganpa lapvlqdfea tiaerrnlvl kesqrasqvt
3301  flcsniihfe slrtrtaeal nldaalfeli krcqqmcsfa sqfnssysel elrllqrvdt
3361  glehpigsse wllsahkqlt qdmstqraiq tekeqqietv cetiqnlvdn iktvltghnr
3421  qlgdykhllk amakdeeaal adgedvpyen svrqflgeyk swqdniqtvl ftivqamgqv
3481  rsqehvemlq eitptlkelk tqsgsiynnl vsfasplvtd atnecsspts satyqpsfaa
3541  avrsntgqkt qpdvmsqnar kliqknlats adtppstvpg tgksvacspk kavrdpktgk
3601  avqernsyav svwkrvkakl egrdvdpnrr msvaeqvdyv ikeatnldnl aqlyegwtaw
3661  v SMG5 nucleotide sequence (GenBank Accession No. NM_015327.2, nt 150-3200)(SEQ ID
NO: 9)
 150                    a tgagccaagg ccccccaca ggggagagca
 181  gcgagcccga agcaaaagtc ctccacacta agcggcttta ccgggctgtg gtggaggctg
 241  tgcatcgact tgacctcatc ctttgcaaca aaactgctta tcaagaagta ttcaaaccag
 301  aaaacattag cctgaggaac aagctgcgtg agctctgcgt caagcttatg ttcctgcacc
 361  cagtggacta tgggagaaag gctgaggagc tgctgtggag aaaggtatac tatgaagtta
 421  tccagcttat caagactaac aaaaagcaca tccacagccg gagcactttg gaatgtgcct
 481  acaggacgca cctggttgct ggtattggct tctaccagca tctccttctc tatatccagt
 541  cccactacca gctgaactg cagtgctgca tcgactggac ccatgtcact gacccctca
 601  taggatgcaa gaagccagtg tctgcctcag ggaaggagat ggattgggca cagatggcat
 661  gtcaccgatg tctggtgtat ctgggggatt tgtcccgata tcagaatgaa ttagctggcg
 721  tagataccga gctgctagcc gagagatttt actaccaagc cctgtcagta gctcctcaga
 781  ttggaatgcc cttcaatcag ctgggcaccc tggcaggcag caagtactat aatgtggaga
 841  ccatgtattg ctacctgcgc tgcatccagt cagaagtgtc ctttgaggga gcctatggga
 901  acctcaagcg gctgtatgac aaggcagcca aaatgtacca ccaactgaag aagtgtgaga
 961  ctcggaaact gtctcctggc aaaaagcgat gtaaagacat taaaaggttg ctagtgaact
1021  ttatgtatct gcaaagcctc ctacagccca aaagcgactc cgtggactca gagtcgacct
1081  cactttgcca gtcagtcctg gaggacttca acctctgcct cttctacctg ccctcctcac
1141  ccaacctcag cctgccagt gaggatgagg aggagtatga gagtggatat gctttcctcc
1201  cggaccttct catctttcaa atggtcatca tctgcctat gtgtgtgcac agcttggaga
1261  gagcaggatc caagcagtac agtgcagcca ttgccttcac cctggccctc ttttcccacc
1321  tcgtcaatca tgtcaacata cggctgcagg ctgagctgga gagggcgag aatcccgtcc
1381  cagcattcca gagtgatggc acagatgaac cagagtccaa ggaacctgtg gagaaagagg
1441  aagagccaga tcctgagcct cctcctgtaa cacccccaagt gggtgagggc agaaagagcc
1501  gtaagttctc tcgcctctcc tgtctccgcc gtcgccgcca cccacccaaa gttggtgatg
1561  acagtgacct gagtgaaggc tttgaatcgg actcaagcca tgactcagcc cgggccagtg
1621  agggctcaga cagtggctct gacaagagtc ttgaaggtgg gggaacggcc tttgatgctg
1681  aaacagactc ggaaatgaat agccaggagt cccgatcaga cttggaagat atggaggaag
1741  aagagggac acggtcacca accctggagc cccctcgggg cagatcagag gctcccgatt
1801  ccctcaatgg cccactgggc cccagtgagg ctagccattgc cagcaatcta caagccatgt
1861  ccacccagat gttccagact aagcgctgct tccgactggc cccaccctt agcaacctgc
1921  tcctccagcc caccaccaac cctcatacct cggccagcca caggccttgc gtcaatgggg
1981  atgtagacaa gccttcagag ccagcctctg aggagggctc tgagtcggag gggagtgagt
2041  ccagtggacg ctcctgtcgg aatgagcgca gcatccagga gaagcttcag gtcctgatgg
2101  ccgaaggtct gcttcctgct gtgaaagtct tcctggactg gcttcggacc aaccccgacc
2161  tcatcatcgt gtgtgcgcag agctctcaaa gtctgtggaa ccgcctgtct gtgttgctga
2221  atctgttgcc tgctgctggt gaactccagg agtctggcct ggccttgtgt cctgaggtcc
2281  aagatcttct tgaaggttgt gaactgcctg acctccccctc tagccttctg ctcccagagg
2341  acatggctct tcgtaacctg ccccccgctcc gagctgccca cagacgcttt aactttgaca
2101  cagatcggcc cctgctcagc accttagagg agtcagtggt gcgcatctgc tgcatccgca
2461  gctttggtca tttcatcgcc cgcctgcaag gcagcatcct gcagttcaac ccagaggttg
2521  gcatcttcgt cagcattcgt cagtctgagc aggagagcct gctgcagcag gcccaggcac
2581  aattccgaat ggcacaggag gaagctcgtc ggaacaggct catgagagac atggctcagc
2641  tacgacttca gctcgaagtg tctcagctgg agggcagcct gcagcagccc aaggcccagt
2701  cagccatgtc tccctacctc gtccctgaca ccaggccct ctgccaccat ctccctgtca
2761  tccgccaact ggccaccagt ggccgcttca ttgtcatcat cccaaggaca gtgatcgatg
2821  gcctggattt gctgaagaag gaacaccag gggcccggga tgggattcgg tacctggagg
2881  cagatttaa aaaaggaaac agtacattc gctgccaaga agaggtggga aagagctttg
2941  aacggcataa gctgaagagg caggatgcag atgcctggac tctctataag atcctagaca
3001  gctgcaaaca gctgactctg gcccaggggg caggtgagga ggatccgagt ggcatggtga
3061  ccatcatcac aggccttcca ctgacaacc ccagcgtgct tcaggccc atgcaggcag
3121  ccctgcaggc cgctgcccac gccagtgtgg acatcaagaa tgttctggac ttcacaagc
3181  agtggaagga aattggttga
```

| Sequences |
|---|

SMG5 amino acid sequence (GenBank Accession No. NP_056142.2)(SEQ ID NO: 10)
```
  1 msqgpptges sepeakvlht krlyravvea vhrldlilcn ktayqevfkp enislrnklr
 61 elcvklmflh pvdygrkaee llwrkvyyev iqliktnkkh ihsrstleca yrthlvagig
121 fyqhlllyiq shyqlelqcc idwthvtdpl igckkpvsas gkemdwaqma chrclvylgd
181 lsryqnelag vdtellaerf yyqalsvapq igmpfnqlgt lagskyynve amycylrciq
211 sevsfegayg nlkrlydkaa kmyhqlkkce trklspgkkr ckdikrllvn fmylqsllqp
301 ksssvdselt slcqsvledf nlclfylpss pnlslasede eeyesgyafl pdllifqmvi
361 iclmcvhsle ragskqysaa iaftlalfsh lvnhvnirlq aeleegenpv pafqsdgtde
421 peskepveke eepdpepppv tpqvgegrks rkfsrlsclr rrrhppkvgd dsdlsegfes
481 dsshdsaras egsdsgsdks legggtafda etdsemnsqe srsdledmee eegtrsptle
541 pprgrseapd slngplgpse asiasnlqam stqmfqtkrc frlaptfsnl llqpttnpht
601 sashrpcvng dvdkpsepas eegsesegse ssgrscrner siqeklqvlm aegllpavkv
661 fldwlrtnpd liivcaqssq slwnrlsvll nllpaagelq esglalcpev qdllegcelp
721 dlpsslllpe dmalrnlppl raahrrfnfd tdrpllstle esvvriccir sfghfiarlq
781 gsilqfnpev gifvsiaqse qesllqqaqa qfrmaqeear rnrlmrdmaq lrlqlevsql
841 egslqqpkaq samspylvpd tqalchhlpv irqlatsgrf iviiprtvid gldllkkehp
901 gardgiryle aefkkgnryi rcqkevgksf erhklkrqda dawtlykild sckqltlaqg
961 ageedpsgmv tiitglpldn psvlsgpmqa alqaaahasv diknvldfyk qwkeig
```

SMG6 nucleotide sequence (GenBank Accession No. BC064916.1, nt 296-1831)(SEQ ID NO: 11)
```
 296                                                             atgga
 301 gacattccct gcagtggctg agaaggtcct caaggagttc caggtgttac tgcagcacag
 361 cccctctccc attggaagta cccgcatgct gcagcttatg accatcaata tgtttgcagt
 421 acacaactcc cagctgaaag actgcttctc ggaggagtgc cgctctgtga tccaggaaca
 481 aaccgcagct ctgggcttgg ccatgttttc tctactggtc cgccgctgca cctgcttact
 541 taaggagtcc gccaaagctc agctgtcctc tcctgaggac caggatgacc aagacgacat
 601 caaggtgtct tcctttgtcc cggacctgaa ggagctgctc cccagtgtca aagtctggtc
 661 agattggatg ctcggctacc cggacacctg aatcctcct cccacatccc tggatctgcc
 721 ctcgcatgtt gctgtggatg tatggtcgac gctggctgat ttctgtaaca tactgactgc
 781 aatgaatcag tctgaggtgc cactgtacaa ggaccggatg atgacctca cccttcttat
 841 cctggaagag gatcggcttc tctcgggctt tgtcccccttg ctggctgccc ctcaggaccc
 901 ctgctacgtg gagaaaacct cggataaggt tattgcagct gactgcaaaa gggtcacagt
 961 gctgaagtat tttctggaag cctttgtgg acaagaagag cctctgctgg cattcaaggg
1021 tggaaagtat gtgtcagtgg caccccgtccc agacaccatg ggaaaggaaa tgggaagcca
1081 agagggaaca cgactggaga atgaggagga ggatgtggtg attgaagact ttgaggaaga
1141 ttcagaggct gaaggcagcg gaggcgagga tgacatcagg gagcttcggg ccaagaagct
1201 ggctctgccc aggaagatag ctgagcagca gcgtcgccag gaaaagatcc aggctgtcct
1261 ggaggaccac agtcagatga ggcagatgga gctcgaaatc agacctttgt tcctcgtacc
1321 agacaccaac ggcttcattg accacctggc cagtctggcg cggctgctgg agagcaggaa
1381 gtacatcctg gtggtgcccc tcatcgtgat caatgagctc gacggcctgg ccaaggggca
1441 ggagacagac caccgggctg ggggctacgc ccgtgtggta caagagaagg cccgcaagtc
1501 catcgagttc ctcgagcagc gattcgagag tcgggactct tgcctgcgag ccctgaccag
1561 ccgtggcaat gaactcgaat ccatcgcctt ccgcagtgag gacatccactg gccagctggg
1621 taacaacgat gatctcatcc tgtcctgctg cctccactac tgcaaagaca aggctaagga
1681 cttcatgccc gccagcaaag aggagccaat ccggctactg cgggaggtgg tgctgttgac
1741 ggatgaccgg aacctgcgtg tgaaggcgct cacaaggaat gttcctgtac gggacatccc
1801 agccttcctc acgtgggccc aggtgggctg a
```

SMG6 amino acid sequence (GenBank Accession No. AAH64916.1)(SEQ ID NO: 12)
```
  1 metfpavaek vlkefqvllq hspspigstr mlqlmtinmf avhnsqlkdc fseecrsviq
 61 eqaaalglam fsllvrrctc llkesakaql sspedqddqd dikvssfvpd lkellpsvkv
121 wsdwmlgypd twnppptsld lpshvavdvw stladfcnil tavnqsevpl ykdpdddltl
181 lileedrlls gfvpllaapq dpcyvektsd kviaadckrv tvlkyfleal cgqeepllaf
241 kggkyvsvap vpdtmgkemg sqegtrlede eedvviedfe edseaegsgg eddirelrak
301 klalarkiae qqrrqekiqa vledhsqmrq meleirplfl vpdtngfidh laslarlles
361 rkyilvvpli vineldglak gqetdhragg yarvvqekar ksieflegqrf esrdsclral
421 tsrgnelesi afrseditgq lgnnddlils cclhyckdka kdfmpaskee pirllrevvl
481 ltddrnlrvk altrnvpvrd ipafltwaqv g
```

SMG7 nucleotide sequence (GenBank Accession No. BC036381.1, nt 119-3655)(SEQ ID NO: 13)
```
 119                                                                at
 121 gagcctgcag agcgcgcagt acctccggca ggcagaagtc ctgaaggctg acatgacaga
 181 ttctaagctg ggtccagctg aagtctggac atccaggcag gctctgcagg acctgtacca
 241 gaaaatgcta gttaccgatt tggaatacgc tttagacaag aaagtagaac aggatctctg
 301 gaatcacgcc tttaagaatc agatcacaac actacaaggc caggcaaaga atcgagcaaa
 361 tccgaatcgg agtgaagttc aggcaaacct ttctctgttc ctagaggcag ctagtggctt
 421 ctatactcag ttattacaag aactgtgtac agtatttaat gtagatttac catgccgtgt
 481 gaagtcttcc caattgggaa ttatcagcaa taaacagacg cataccagcg ccatagtgaa
 541 gccacagtct agctcctgtt cctatatctg ctcgtccacc ttggagacat
 601 tgctcgatac agaaaccaga ccagccaggc agagtcctac tataggcatg cagctcagct
 661 tgtcccctcc aatggtcagc cttataatca gttggctatc ttagcttctt ccaaaggaga
 721 ccatctgacc acaattttct actactgcag aagcattgct gtgaagttcc cttttcccagc
 781 tgcctccact aatctgcaaa aagcactttc taaagcactg aaagccgag atgaggtgaa
 841 aaccaagtgg ggtgtttctg acttcatcaa ggccttttatt aaattccacg gtcatgtgta
```

```
                           Sequences 901  cctgagtaag agcttggaaa agttgagccc tcttcgagag aaattggaag aacagtttaa
 961  gaggctgcta ttccaaaaag cttccaactc tcagcagtta gttcatgtca ctgtcattaa
1021  cctgtttcaa cttcatcacc ttcgtgactt tagcaatgaa accgagcagc acacttatag
1081  ccaagatgag cagctatgtt ggacacagtt gctggccctc tttatgtctt ttctcggcat
1141  cctgtgcaag tgtcctctac agaatgagtc tcaggaggag tcctacaatg cctatcctct
1201  tccagcagtc aaggtctcca tggactggct aagactcaga cccagggtct ttcaggaggc
1261  agtggtggat gaaagacagt acatttggcc ctggttgatt tctcttctga atagttttcca
1321  tccccatgaa gaggacctct caagtattag tgcgacacca cttccagagg agtttgaatt
1381  acaaggattt ttggcattga gaccttcttt caggaacttg gattttttcca aaggtcacca
1441  gggtattaca ggggacaaag aaggccagca acgacgaata cgacagcaac gcttgatctc
1501  tataggcaaa tggattgctg ataatcagcc aaggctgatt cagtgtgaaa atgaggtagg
1561  gaaattgttg tttatcacag aaatcccaga attaatactg aagaccccca gtgaagccaa
1621  agagaacctc attctgcaag aaacatctgt gatagagtcg ctggctgcag atgggagccc
1681  agggctaaaa tcagtgctat ctacaagccg aaatttaagc aacaactgtg acacaggaga
1741  gaagccagtg gttaccttca agaaaacat taagacacga gaagtgaaca gagaccaagg
1801  aagaagtttt cctcccaaag aggtaaaatc ccagacagaa ctaagaaaga ctccagtgtc
1861  tgaagccaga aaaacacctg taactcaaac cccaactcaa gcaagtaact cccagttcat
1921  ccccattcat caccctggag ccttccctcc tcttcccagc aggccagggt ttccgccccc
1981  aacatatgtt atccccccgc ctgtggcatt ttctatgggc tcaggttaca ccttcccagc
2041  tggtgtttct gtcccaggaa cctttcttca gcctacagct cactctccag caggaaacca
2101  ggtgcaagct gggaaacagt cccacattcc ttacagccaa caacggccct ctggaccagg
2161  gccaatgaac cagggacctc aacaatcaca gccaccttcc cagcaacccc ttacatcttt
2221  accagctcag ccaacagcac agtctacaag ccagctgcag gttcaagctc taactcagca
2281  acaacaatcc cctacaaaag ctgtgccggc tttggggaaa agcccgcctc accactctgg
2341  attccagcag tatcaacagg cagatgcctc caaacagctg tggaatcccc ctcaggttca
2401  aggcccatta gggaaaatta tgcctgtgaa acagccctac taccttcaga cccaagaccc
2461  cataaaactg tttgagccgt cattgcaacc tcctgtaatg cagcagcagc ctctagaaaa
2521  aaaaatgaag ccttttccca tggagccata taaccataat ccctcagaag tcaaggtccc
2581  aaaattctac tgggattctt cctacagcat ggctgataac agatctgtaa tggcacagca
2641  agcaaacata gaccgcaggg gcaaacggtc accaggaatc ttccgtccag agcaggatcc
2701  tgtacccaga atgccgtttg aggaccccaa gagctcccct ctgcttcctc cggacctgtt
2761  aaagagtctg gctgccttgg aggaagagga agagctgatt ttttctaaca ctcctgatct
2821  ttacccggct ctgctggggc ctctcgcctc tcttcctgga cgaagccttt ttaaatcctt
2881  attggagaag ccctcagagc tcatgtcaca ttcatctctct ttcctgtccc tcaccggatt
2941  ctctctcaat caggaaagat acccaaataa tagtatgttc aatgaggtat atgggaaaaa
3001  cctgacatcc agctccaaag cagaactcag tccctcaatg gcccccccagg aaacatctct
3061  gtattccctt tttgaaggga ctccgtggtc tccatcactt ctgccagtt cagatcattc
3121  aacaccagcc agccagtctc ctcattcctc taacccaagc agcctaccca gctctcctcc
3181  aacacacaac cataattctg ttccattctc caattttgga cccattggga ctccagataa
3241  cagggataga aggactgcag atcggtggaa aactgataag ccagccatgg gtgggtttgg
3301  cattgattat ctctcagcaa cgtcatcctc tgagagcagt tggcatcagg ccagcactcc
3361  gagtggcacc tggacaggcc atgggccttc catggagaat tcctctgctg tcctcatgga
3421  aagcctaaag aagcaacagc atggggtcca gcagttgggg cccaaaagac agtctgaaga
3481  ggaaggaagc agcagtatct gcgtagccca cagagggccc aggcccctgc ccagctgcag
3541  tctcccagcc tccactttca gagtgaaatt caaggcagca cggacatgtg cccatcaggc
3601  acagaagaaa acacgacgtc gtccatttg gaagagacga agaaaggaa aataa
```

SMG7 amino acid sequence (GenBank Accession No. AAH36381.1)(SEQ ID NO: 14)

```
   1  mslqsaqylr qaevlkadmt dsklgpaevw tsrqalqdly qkmlvtdley aldkkveqdl
  61  wnhafknqit tlqggqaknra npnrsevqan lslfleaasg fytqllqelc tvfnvdlpcr
 121  vkssqlgiis nkqthtsaiv kpqssscsyi cqhclvhlgd iaryrnqtsq aesyyrhaaq
 181  lvpsngqpyn qlailasskg dhlttifyyc rsiavkfpfp aastnlqkal skalesrdev
 241  ktkwgvsdfi kafikfhghv ylskslekls plrekleeqf krllfqkafn sqqlvhvtvi
 301  nlfqlhhlrd fsneteqhty sqdeqlcwtq llalfmsflg ilckcplqne sqeesynayp
 361  lpavkvsmdw lrlrprvfqe avvderqyiw pwlisllnsf hpheedlssi satplpeefe
 421  lqgflalrps frnldfskgh qgitgdkegq qrrirqqrli sigkwiadnq prliqcenev
 481  gkllfiteip eliledpsea kenlilqets vieslaadgs pglksvlsts rnlsnncdtg
 541  ekpvvtfken iktrevnrdq grsfppkevk sqtelrktpv searktpvtq tptqasnsqf
 601  ipihhpgafp plpsrpgfpp ptyvipppva fsmgsgytfp agvsvpgtfl qptahspagn
 661  qvqagkqshi pysqqrpsgp gpmnqgpqqs qppsqqplts lpaqptaqst sqlqvqaltq
 721  qqqsptkavp algksppphs gfqqyqqada skqlwnppqv qgplgkimpv kqpyylqtqd
 781  piklfepslq ppvmqqqple kkmkpfpmep ynhnpsevkv pefywdssys madnrsvmaq
 841  qanidrrgkr spgifrpeqd pvprmpfedp ksspllppdl lkslaaleee eelifsntpd
 901  lypallgpla slpgrslfks llekpselms hsssflsltg fslnqerypn nsmfnevygk
 961  nltssskael spsmapqets lyslfegtpw spslpassdh stpasqsphs snpsslpssp
1021  pthnhnsvpf snfgpigtpd nrdrrtadrw ktdkpamggf gidylsatss sesswhqast
1081  psgtwtghgp smedssavlm eslkkqqhgv qqlgpkrqse eegsssicva hrgprplpsc
1141  slpastfrvk fkaartcahq aqkktrrrpf wkrrkkgk
```

We claim:

1. A method of reducing fused in sarcoma/translocated in sarcoma (FUS/TLS)- or TAR-DNA-binding protein 43 (TDP-43)-mediated neuronal cytotoxicity, the method comprising:
   providing to a neuronal cell a composition comprising a UPF1 polypeptide or a nucleic acid encoding a UPF1 polypeptide, thereby reducing the FUS/TLS- or TDP-43-mediated neuronal cytotoxicity in the neuronal cell;
   wherein the UPF1 polypeptide comprises the amino acid sequence of SEQ ID NO:2.

2. The method of claim 1, wherein the composition comprises the nucleic acid encoding the UPF1 polypeptide.

3. The method of claim 1, wherein the composition comprises a vector comprising the nucleic acid encoding the UPF1 polypeptide.

4. The method of claim 3, wherein the vector is a viral vector.

5. The method of claim 4, wherein the viral vector is a retroviral vector, a lentiviral vector, an adenoviral vector, or an adeno-associated viral vector.

6. The method of claim 2, wherein the neuronal cytotoxicity is an FUS/TLS-mediated neuronal cytotoxicity.

7. The method of claim 2, wherein the neuronal cytotoxicity is a TDP-43-mediated neuronal cytotoxicity.

* * * * *

SEQUENCE LISTING

<160> NUMBER OF SEQ ID NOS: 14

<210> SEQ ID NO 1
<211> LENGTH: 3357
<212> TYPE: DNA
<213> ORGANISM: Homo sapiens

<400> SEQUENCE: 1

| | | | | | | |
|---|---|---|---|---|---|---|
| atgagcgtgg | aggcgtacgg | gcccagctcg | cagactctca | ctttcctgga | cacggaggag | 60 |
| gccgagctgc | ttggcgccga | cacacagggc | tccgagttcg | agttcaccga | ctttactctt | 120 |
| cctagccaga | cgcagacgcc | ccccggcggc | cccggcggcc | cgggcggtgg | cggcgcggga | 180 |
| agcccgggcg | gcgcgggcgc | cggcgctgcg | gcgggacagc | tcgacgcgca | ggttgggccc | 240 |
| gaaggcatcc | tgcagaacgg | ggctgtggac | gacagtgtag | ccaagaccag | ccagttgttg | 300 |
| gctgagttga | acttcgagga | agatgaagaa | gacacctatt | acacgaagga | cctcccccata | 360 |
| cacgcctgca | gttactgtgg | aatacacgat | cctgcctgcg | tggtttactg | taataccagc | 420 |
| aagaagtggt | tctgcaacgg | acgtggaaat | acttctggca | ccacattgt | aaatcacctt | 480 |
| gtgagggcaa | aatgcaaaga | ggtgaccctg | cacaaggacg | ggcccctggg | ggagacagtc | 540 |
| ctggagtgct | acaactgcgg | ctgtcgcaac | gtcttcctcc | tcggcttcat | cccggccaaa | 600 |
| gctgactcag | tggtggtgct | gctgtgcagg | cagcccgtg | ccagcagag | cagcctcaag | 660 |
| gacatcaact | gggacagctc | gcagtggcag | ccgctgatcc | aggaccgctg | cttcctgtcc | 720 |
| tggctggtca | agatcccctc | cgagcaggag | cagctgcggg | cacgccagat | cacggcacag | 780 |
| cagatcaaca | agctggagga | gctgtggaag | gaaaacccctt | ctgccacgct | ggaggacctg | 840 |
| gagaagccgg | ggtggacga | ggagccgcag | catgtcctcc | tgcggtacga | ggacgcctac | 900 |
| cagtaccaga | acatattcgg | gccctggtc | aagctggagg | ccgactacga | caagaagctg | 960 |
| aaggagtccc | agactcaaga | taacatcact | gtcaggtggg | acctgggcct | taacaagaag | 1020 |
| agaatcgcct | acttcacttt | gcccaagact | gactctgaca | tgcggctcat | gcaggggat | 1080 |
| gagatatgcc | tgcggtacaa | aggggacctt | gcgcccctgt | ggaaagggat | cggccacgtc | 1140 |
| atcaaggtcc | ctgataatta | tggcgatgag | atcgccattg | agctgcggag | cagcgtgggt | 1200 |
| gcacctgtgg | aggtgactca | caacttccag | gtggattttg | tgtggaagtc | gacctccttt | 1260 |
| gacaggatgc | agagcgcatt | gaaaacgttt | gccgtggatg | agacctcggt | gtctggctac | 1320 |
| atctaccaca | agctgttggg | ccacgaggtg | gaggacgtaa | tcaccaagtg | ccagctgccc | 1380 |
| aagcgcttca | cggcgcaggg | cctccccgac | ctcaaccact | cccaggttta | tgccgtgaag | 1440 |
| actgtgctgc | aaagaccact | gagcctgatc | cagggcccgc | caggcacggg | gaagacggtg | 1500 |
| acgtcggcca | ccatcgtcta | ccacctggcc | cggcaaggca | acggccggt | gctggtgtgt | 1560 |
| gctccgagca | acatcgccgt | ggaccagcta | acggagaaga | tccaccagac | ggggctaaag | 1620 |
| gtcgtgcgcc | tctgcgccaa | gagccgtgag | gccatcgact | ccccggtgtc | ttttctggcc | 1680 |
| ctgcacaacc | agatcaggaa | catggacagc | atgcctgagc | tgcagaagct | gcagcagctg | 1740 |
| aaagacgaga | ctggggagct | gtcgtctgcc | gacgagaagc | ggtaccgggc | cttgaagcgc | 1800 |
| accgcagaga | gagctgct | gatgaacgca | gatgtcatct | gctgcacatg | tgtgggcgcc | 1860 |
| ggtgacccga | ggctggccaa | gatgcagttc | cgctccattt | taatcgacga | aagcacccag | 1920 |
| gccaccgagc | cggagtgcat | ggttcccgtg | gtcctcgggg | ccaagcagct | gatccttgta | 1980 |
| ggcgaccact | gccagctggg | cccagtggtg | atgtgcaaga | aggcggccaa | ggccgggctg | 2040 |
| tcacagtcgc | tcttcgagcg | cctggtggtg | ctgggcatcc | ggcccatccg | cctgcaggtc | 2100 |

-continued

```
cagtaccgga tgcaccctgc actcagcgcc ttcccatcca acatcttcta cgagggctcc    2160
ctccagaatg gtgtcactgc agcggatcgt gtgaagaagg gatttgactt ccagtggccc    2220
caacccgata aaccgatgtt cttctacgtg acccagggcc aagaggagat tgccagctcg    2280
ggcacctcct acctgaacag gaccgaggct gcgaacgtgg agaagatcac cacgaagttg    2340
ctgaaggcag gcgccaagcc ggaccagatt ggcatcatca cgccctacga gggccagcgc    2400
tcctacctgg tgcagtacat gcagttcagc ggctccctgc acaccaagct ctaccaggaa    2460
gtggagatcg ccagtgtgga cgcctttcag ggacgcgaga aggacttcat catcctgtcc    2520
tgtgtgcggg ccaacgagca ccaaggcatt ggcttttta atgaccccag gcgtctgaac    2580
gtggccctga ccagagcaag gtatggcgtc atcattgtgg caacccgaa ggcactatca    2640
aagcagccgc tctggaacca cctgctgaac tactataagg agcagaaggt gctggtggag    2700
gggccgctca acaacctgcg tgagagcctc atgcagttca gcaagccacg gaagctggtc    2760
aacactatca acccgggagc ccgcttcatg accacagcca tgtatgatgc ccgggaggcc    2820
atcatcccag gctccgtcta tgatcggagc agccagggcc ggccttccag catgtacttc    2880
cagacccatg accagattgg catgatcagt gccggcccta gccacgtggc tgccatgaac    2940
attcccatcc ccttcaacct ggtcatgcca cccatgccac cgcctggcta ttttggacaa    3000
gccaacgggc ctgctgcagg gcgaggcacc ccgaaaggca agactggtcg tggggggacgc    3060
cagaagaacc gctttgggct tcctggaccc agccagacta acctccccaa cagccaagcc    3120
agccaggatg tggcgtcaca gcccttctct cagggcgccc tgacgcaggg ctacatctcc    3180
atgagccagc cttcccagat gagccagccc ggcctctccc agccggagct gtcccaggac    3240
agttaccttg gtgacgagtt taaatcacaa atcgacgtgg cgctctcaca ggactccacg    3300
taccaggag agcgggctta ccagcatggc ggggtgacgg ggctgtccca gtattaa       3357
```

<210> SEQ ID NO 2
<211> LENGTH: 1118
<212> TYPE: PRT
<213> ORGANISM: Homo sapiens

<400> SEQUENCE: 2

```
Met Ser Val Glu Ala Tyr Gly Pro Ser Ser Gln Thr Leu Thr Phe Leu
1               5                   10                  15

Asp Thr Glu Glu Ala Glu Leu Leu Gly Ala Asp Thr Gln Gly Ser Glu
            20                  25                  30

Phe Glu Phe Thr Asp Phe Thr Leu Pro Ser Gln Thr Gln Thr Pro Pro
        35                  40                  45

Gly Gly Pro Gly Gly Pro Gly Gly Gly Ala Gly Ser Pro Gly Gly
    50                  55                  60

Ala Gly Ala Gly Ala Ala Gly Gln Leu Asp Ala Gln Val Gly Pro
65                  70                  75                  80

Glu Gly Ile Leu Gln Asn Gly Ala Val Asp Asp Ser Val Ala Lys Thr
                85                  90                  95

Ser Gln Leu Leu Ala Glu Leu Asn Phe Glu Glu Asp Glu Glu Asp Thr
            100                 105                 110

Tyr Tyr Thr Lys Asp Leu Pro Ile His Ala Cys Ser Tyr Cys Gly Ile
        115                 120                 125

His Asp Pro Ala Cys Val Val Tyr Cys Asn Thr Ser Lys Lys Trp Phe
    130                 135                 140

Cys Asn Gly Arg Gly Asn Thr Ser Gly Ser His Ile Val Asn His Leu
```

-continued

```
            145                 150                 155                 160
        Val Arg Ala Lys Cys Lys Glu Val Thr Leu His Lys Asp Gly Pro Leu
                        165                 170                 175
        Gly Glu Thr Val Leu Glu Cys Tyr Asn Cys Gly Cys Arg Asn Val Phe
                        180                 185                 190
        Leu Leu Gly Phe Ile Pro Ala Lys Ala Asp Ser Val Val Leu Leu
                    195                 200                 205
        Cys Arg Gln Pro Cys Ala Ser Gln Ser Ser Leu Lys Asp Ile Asn Trp
                210                 215                 220
        Asp Ser Ser Gln Trp Gln Pro Leu Ile Gln Asp Arg Cys Phe Leu Ser
        225                 230                 235                 240
        Trp Leu Val Lys Ile Pro Ser Glu Gln Glu Gln Leu Arg Ala Arg Gln
                        245                 250                 255
        Ile Thr Ala Gln Gln Ile Asn Lys Leu Glu Glu Leu Trp Lys Glu Asn
                        260                 265                 270
        Pro Ser Ala Thr Leu Glu Asp Leu Glu Lys Pro Gly Val Asp Glu Glu
                    275                 280                 285
        Pro Gln His Val Leu Leu Arg Tyr Glu Asp Ala Tyr Gln Tyr Gln Asn
                290                 295                 300
        Ile Phe Gly Pro Leu Val Lys Leu Glu Ala Asp Tyr Asp Lys Lys Leu
        305                 310                 315                 320
        Lys Glu Ser Gln Thr Gln Asp Asn Ile Thr Val Arg Trp Asp Leu Gly
                        325                 330                 335
        Leu Asn Lys Lys Arg Ile Ala Tyr Phe Thr Leu Pro Lys Thr Asp Ser
                        340                 345                 350
        Asp Met Arg Leu Met Gln Gly Asp Glu Ile Cys Leu Arg Tyr Lys Gly
                    355                 360                 365
        Asp Leu Ala Pro Leu Trp Lys Gly Ile Gly His Val Ile Lys Val Pro
                370                 375                 380
        Asp Asn Tyr Gly Asp Glu Ile Ala Ile Glu Leu Arg Ser Ser Val Gly
        385                 390                 395                 400
        Ala Pro Val Glu Val Thr His Asn Phe Gln Val Asp Phe Val Trp Lys
                        405                 410                 415
        Ser Thr Ser Phe Asp Arg Met Gln Ser Ala Leu Lys Thr Phe Ala Val
                        420                 425                 430
        Asp Glu Thr Ser Val Ser Gly Tyr Ile Tyr His Lys Leu Leu Gly His
                    435                 440                 445
        Glu Val Glu Asp Val Ile Thr Lys Cys Gln Leu Pro Lys Arg Phe Thr
                450                 455                 460
        Ala Gln Gly Leu Pro Asp Leu Asn His Ser Gln Val Tyr Ala Val Lys
        465                 470                 475                 480
        Thr Val Leu Gln Arg Pro Leu Ser Leu Ile Gln Gly Pro Pro Gly Thr
                        485                 490                 495
        Gly Lys Thr Val Thr Ser Ala Thr Ile Val Tyr His Leu Ala Arg Gln
                        500                 505                 510
        Gly Asn Gly Pro Val Leu Val Cys Ala Pro Ser Asn Ile Ala Val Asp
                    515                 520                 525
        Gln Leu Thr Glu Lys Ile His Gln Thr Gly Leu Lys Val Val Arg Leu
                530                 535                 540
        Cys Ala Lys Ser Arg Glu Ala Ile Asp Ser Pro Val Ser Phe Leu Ala
        545                 550                 555                 560
        Leu His Asn Gln Ile Arg Asn Met Asp Ser Met Pro Glu Leu Gln Lys
                        565                 570                 575
```

-continued

Leu Gln Gln Leu Lys Asp Glu Thr Gly Glu Leu Ser Ser Ala Asp Glu
            580                 585                 590

Lys Arg Tyr Arg Ala Leu Lys Arg Thr Ala Glu Arg Glu Leu Leu Met
            595                 600                 605

Asn Ala Asp Val Ile Cys Cys Thr Cys Val Gly Ala Gly Asp Pro Arg
            610                 615                 620

Leu Ala Lys Met Gln Phe Arg Ser Ile Leu Ile Asp Glu Ser Thr Gln
625                 630                 635                 640

Ala Thr Glu Pro Glu Cys Met Val Pro Val Leu Gly Ala Lys Gln
            645                 650                 655

Leu Ile Leu Val Gly Asp His Cys Gln Leu Gly Pro Val Val Met Cys
            660                 665                 670

Lys Lys Ala Ala Lys Ala Gly Leu Ser Gln Ser Leu Phe Glu Arg Leu
            675                 680                 685

Val Val Leu Gly Ile Arg Pro Ile Arg Leu Gln Val Gln Tyr Arg Met
            690                 695                 700

His Pro Ala Leu Ser Ala Phe Pro Ser Asn Ile Phe Tyr Glu Gly Ser
705                 710                 715                 720

Leu Gln Asn Gly Val Thr Ala Ala Asp Arg Val Lys Lys Gly Phe Asp
            725                 730                 735

Phe Gln Trp Pro Gln Pro Asp Lys Pro Met Phe Phe Tyr Val Thr Gln
            740                 745                 750

Gly Gln Glu Glu Ile Ala Ser Ser Gly Thr Ser Tyr Leu Asn Arg Thr
            755                 760                 765

Glu Ala Ala Asn Val Glu Lys Ile Thr Thr Lys Leu Leu Lys Ala Gly
            770                 775                 780

Ala Lys Pro Asp Gln Ile Gly Ile Ile Thr Pro Tyr Glu Gly Gln Arg
785                 790                 795                 800

Ser Tyr Leu Val Gln Tyr Met Gln Phe Ser Gly Ser Leu His Thr Lys
            805                 810                 815

Leu Tyr Gln Glu Val Glu Ile Ala Ser Val Asp Ala Phe Gln Gly Arg
            820                 825                 830

Glu Lys Asp Phe Ile Ile Leu Ser Cys Val Arg Ala Asn Glu His Gln
            835                 840                 845

Gly Ile Gly Phe Leu Asn Asp Pro Arg Arg Leu Asn Val Ala Leu Thr
            850                 855                 860

Arg Ala Arg Tyr Gly Val Ile Val Gly Asn Pro Lys Ala Leu Ser
865                 870                 875                 880

Lys Gln Pro Leu Trp Asn His Leu Leu Asn Tyr Tyr Lys Glu Gln Lys
            885                 890                 895

Val Leu Val Glu Gly Pro Leu Asn Asn Leu Arg Glu Ser Leu Met Gln
            900                 905                 910

Phe Ser Lys Pro Arg Lys Leu Val Asn Thr Ile Asn Pro Gly Ala Arg
            915                 920                 925

Phe Met Thr Thr Ala Met Tyr Asp Ala Arg Glu Ala Ile Ile Pro Gly
            930                 935                 940

Ser Val Tyr Asp Arg Ser Ser Gln Gly Arg Pro Ser Ser Met Tyr Phe
945                 950                 955                 960

Gln Thr His Asp Gln Ile Gly Met Ile Ser Ala Gly Pro Ser His Val
            965                 970                 975

Ala Ala Met Asn Ile Pro Ile Pro Phe Asn Leu Val Met Pro Pro Met
            980                 985                 990

-continued

| | | | | | | | | | | |
|---|---|---|---|---|---|---|---|---|---|---|
|Pro|Pro|Pro|Gly|Tyr|Phe|Gly|Gln|Ala|Asn|Gly|Pro|Ala|Ala|Gly|Arg|
| | |995| | | |1000| | | |1005| |

Gly Thr Pro Lys Gly Lys Thr Gly Arg Gly Gly Arg Gln Lys Asn
        1010            1015              1020

Arg Phe Gly Leu Pro Gly Pro Ser Gln Thr Asn Leu Pro Asn Ser
        1025            1030              1035

Gln Ala Ser Gln Asp Val Ala Ser Gln Pro Phe Ser Gln Gly Ala
        1040            1045              1050

Leu Thr Gln Gly Tyr Ile Ser Met Ser Gln Pro Ser Gln Met Ser
        1055            1060              1065

Gln Pro Gly Leu Ser Gln Pro Glu Leu Ser Gln Asp Ser Tyr Leu
        1070            1075              1080

Gly Asp Glu Phe Lys Ser Gln Ile Asp Val Ala Leu Ser Gln Asp
        1085            1090              1095

Ser Thr Tyr Gln Gly Glu Arg Ala Tyr Gln His Gly Gly Val Thr
        1100            1105              1110

Gly Leu Ser Gln Tyr
        1115

<210> SEQ ID NO 3
<211> LENGTH: 3819
<212> TYPE: DNA
<213> ORGANISM: Homo sapiens

<400> SEQUENCE: 3

```
atgccagctg agcgtaaaaa gccagcaagt atggaagaaa aagactcttt accaaacaac      60
aaggaaaaag actgcagtga aaggcggaca gtgagcagca aggagaggcc aaaagacgat     120
atcaagctca ctgccaagaa ggaggtcagc aaggcccctg aagacaagaa gaagagactg     180
gaagatgata gagaaaaaa ggaagacaag gaacgcaaga aaaagacga agaaaggtg       240
aaggcagagg aagaatcaaa gaaaaagaa gaggaagaaa aaagaaaca tcaagaggaa      300
gagagaaaga agcaagaaga gcaggccaaa cgtcagcaag aagaagaagc agctgctcag     360
atgaaagaaa aagaagaatc cattcagctt catcaggaag cttgggaacg acatcattta     420
agaaaggaac ttcgtagcaa aaaccaaaat gctccggaca gccgaccaga ggaaaacttc     480
ttcagccgcc tcgactcaag tttgaagaaa aatactgctt ttgtcaagaa actaaaaact     540
attacagaac aacagagaga ctccttgtcc catgatttta atggcctaaa tttaagcaaa     600
tacattgcag aagctgtagc ttccatcgtg aagcaaaac taaaaatctc tgatgtgaac     660
tgtgctgtgc acctctgctc tctctttcac cagcgttatg ctgactttgc cccatcactt     720
cttcaggtct ggaaaaaaca ttttgaagca aggaaagagg agaaaacacc taacatcacc     780
aagttaagaa ctgatttgcg tttttattgca gaattgacaa tagttgggat ttcactgac      840
aaggaaggtc tttccttaat ctatgaacag ctaaaaaata ttattaatgc tgatcgggag     900
tcccacactc atgtctctgt agtgattagt ttctgtcgac attgtggaga tgatattgct     960
ggacttgtac aaggaaagt aaagagtgct gcagagaagt ttaatttgag ttttcctcct    1020
agtgagataa ttagtccaga gaacaacag cccttccaga tcttttaaa agagtacttt     1080
acgtctttga ccaaacacct gaaagggac acagggagc tccagaatac tgagagacaa     1140
aacaggcgca ttctacattc taaaggggag ctcagtgaag atagacataa acagtatgag    1200
gaatttgcta tgtcttacca gaagctgctg gcaaattctc aatccttagc agaccttttg     1260
gatgaaaata tgccagatct tcctcaagac aaacccacac cagaagaaca tgggcctgga    1320
```

```
attgatatat tcacacctgg taaacctgga gaatatgact tggaaggtgg tatatgggaa    1380
gatgaagatg ctcggaattt ttatgagaac ctcattgatt tgaaggcttt tgtcccagcc    1440
atcttgttta aagacaatga aaaaagttgt cagaataaag agtccaacaa agatgatacc    1500
aaagaggcaa aagaatctaa ggagaataag gaggtatcaa gtcccgatga tttggaactt    1560
gagttggaga atctagaaat taatgatgac accttagaat tagagggtgg agatgaagct    1620
gaagatctta caaagaaact tcttgatgaa caagaacaag aagatgagga agccagcact    1680
ggatctcatc tcaagctcat agtagatgct ttcctacagc agttacccaa ctgtgtcaac    1740
cgagatctga tagacaaggc agcaatggat ttttgcatga acatgaacac aaaagcaaac    1800
aggaagaagt tggtacgggc actcttcata gttcctagac aaaggttgga tttgctacca    1860
ttttatgcaa gattggttgc tacattgcat ccctgcatgt ctgatgtagc agaggatctt    1920
tgttccatgc tgaggggggga tttcagattt catgtacgga aaaaggacca gatcaatatt    1980
gaaacaaaga ataaaactgt tcgttttata ggagaactaa ctaagtttaa gatgttcacc    2040
aaaaatgaca cactgcattg tttaaagatg cttctgtcag acttctctca tcaccatatt    2100
gaaatggcat gcaccctgct ggagacatgt ggacggtttc ttttcagatc tccagaatct    2160
cacctgagga ccagtgtact tttggagcaa atgatgagaa agaagcaagc aatgcatctt    2220
gatgcgagat acgtcacaat ggtagagaat gcatattact actgcaaccc acctccagct    2280
gaaaaaaccg tgaaaagaa acgtcctcct ctccaggaat atgtccggaa acttttgtac    2340
aaagatctct ctaaggttac caccgagaag gttttgagac agatgcgaaa gctgccctgg    2400
caggaccaag aagtgaaaga ctatgttatt tgttgtatga taaacatctg gaatgtgaaa    2460
tataatagta ttcattgtgt agccaacctc ttagcaggac tagtgctcta ccaagaggat    2520
gttgggatcc acgttgtgga tggagtgtta aagatattc gattaggaat ggaggttaat    2580
caacctaaat ttaatcagag gcgcatcagc agtgccaagt tcttaggaga actttacaat    2640
taccgaatgg tggaatcagc tgttattttc agaactctgt attctttac ctcatttggt    2700 gttaatcctg atggctctcc aagttccctg acccacctg agcatctttt cagaattaga    2760
ctcgtatgca ctattctgga cacatgtggc cagtactttg acagaggttc cagtaaacga    2820
aaacttgatt gtttccttgt atattttcag cgttatgttt ggtggaagaa aagtttggag    2880
gtttggacaa aagaccatcc atttcctatt gatatagatt acatgatcag tgatacacta    2940
gaactgctaa gaccaaagat caaactctgt aattctctgg aagaatccat caggcaggta    3000
caagacttgg aacgagaatt cttaataaaa ctaggcctag taaatgacaa agactcaaaa    3060
gattctatga cagaaggaga aaatcttgaa gaggatgaag aagaagaaga aggtggggct    3120
gaaacagaag aacaatctgg aaatgaaagt gaagtaaatg agccagaaga agaggagggt    3180
tctgataatg atgatgatga gggagaagaa gaggaggaag agaatacaga ttaccttaca    3240
gattccaata aggaaaatga aaccgatgaa gagaatactg aggtaatgat taaaggcggt    3300
ggacttaagc atgtaccttg tgtagaagat gaggacttca ttcaagctct ggataaaatg    3360
atgctagaaa atctacagca acgaagtggt gaatctgtta aagtgcacca actagatgtg    3420
gccattcctt tgcatctcaa aagccagctg aggaaagggc ccccactggg aggtggggaa    3480
ggagaggctg agtctgcaga cacaatgccg tttgtcatgt aacaagaaa aggcaataaa    3540 cagcagttta agatccttaa tgtacccatg tcctctcaac ttgctgcaaa tcactggaac    3600
cagcaacagg cagaacaaga agagaggatg agaatgaaga agctcacact agatatcaat    3660
gaacggcaag aacaagaaga ttatcaagaa atgttgcagt ctcttgcaca gcgcccagct    3720
```

-continued

```
ccagcaaaca ccaatcgtga gaggcggcct cgctaccaac atccgaaggg agcacctaat    3780
gcagatctaa tctttaagac tggtgggagg agacgttga                           3819
```

<210> SEQ ID NO 4
<211> LENGTH: 1272
<212> TYPE: PRT
<213> ORGANISM: Homo sapiens

<400> SEQUENCE: 4

```
Met Pro Ala Glu Arg Lys Lys Pro Ala Ser Met Glu Glu Lys Asp Ser
1               5                   10                  15

Leu Pro Asn Asn Lys Glu Lys Asp Cys Ser Glu Arg Arg Thr Val Ser
            20                  25                  30

Ser Lys Glu Arg Pro Lys Asp Asp Ile Lys Leu Thr Ala Lys Lys Glu
        35                  40                  45

Val Ser Lys Ala Pro Glu Asp Lys Lys Arg Leu Glu Asp Asp Lys
    50                  55                  60

Arg Lys Lys Glu Asp Lys Glu Arg Lys Lys Lys Asp Glu Glu Lys Val
65                  70                  75                  80

Lys Ala Glu Glu Glu Ser Lys Lys Glu Glu Glu Lys Lys Lys
                85                  90                  95

His Gln Glu Glu Glu Arg Lys Lys Gln Glu Glu Gln Ala Lys Arg Gln
            100                 105                 110

Gln Glu Glu Glu Ala Ala Ala Gln Met Lys Glu Lys Glu Glu Ser Ile
        115                 120                 125

Gln Leu His Gln Glu Ala Trp Glu Arg His His Leu Arg Lys Glu Leu
    130                 135                 140

Arg Ser Lys Asn Gln Asn Ala Pro Asp Ser Arg Pro Glu Glu Asn Phe
145                 150                 155                 160

Phe Ser Arg Leu Asp Ser Ser Leu Lys Lys Asn Thr Ala Phe Val Lys
                165                 170                 175

Lys Leu Lys Thr Ile Thr Glu Gln Gln Arg Asp Ser Leu Ser His Asp
            180                 185                 190

Phe Asn Gly Leu Asn Leu Ser Lys Tyr Ile Ala Glu Ala Val Ala Ser
        195                 200                 205

Ile Val Glu Ala Lys Leu Lys Ile Ser Asp Val Asn Cys Ala Val His
    210                 215                 220

Leu Cys Ser Leu Phe His Gln Arg Tyr Ala Asp Phe Ala Pro Ser Leu
225                 230                 235                 240

Leu Gln Val Trp Lys Lys His Phe Glu Ala Arg Lys Glu Glu Lys Thr
                245                 250                 255

Pro Asn Ile Thr Lys Leu Arg Thr Asp Leu Arg Phe Ile Ala Glu Leu
            260                 265                 270

Thr Ile Val Gly Ile Phe Thr Asp Lys Glu Gly Leu Ser Leu Ile Tyr
        275                 280                 285

Glu Gln Leu Lys Asn Ile Ile Asn Ala Asp Arg Glu Ser His Thr His
    290                 295                 300

Val Ser Val Val Ile Ser Phe Cys Arg His Cys Gly Asp Asp Ile Ala
305                 310                 315                 320

Gly Leu Val Pro Arg Lys Val Lys Ser Ala Ala Glu Lys Phe Asn Leu
                325                 330                 335

Ser Phe Pro Pro Ser Glu Ile Ile Ser Pro Glu Lys Gln Gln Pro Phe
            340                 345                 350
```

-continued

```
Gln Asn Leu Leu Lys Glu Tyr Phe Thr Ser Leu Thr Lys His Leu Lys
            355                 360                 365
Arg Asp His Arg Glu Leu Gln Asn Thr Glu Arg Gln Asn Arg Arg Ile
370                 375                 380
Leu His Ser Lys Gly Glu Leu Ser Glu Asp Arg His Lys Gln Tyr Glu
385                 390                 395                 400
Glu Phe Ala Met Ser Tyr Gln Lys Leu Leu Ala Asn Ser Gln Ser Leu
            405                 410                 415
Ala Asp Leu Leu Asp Glu Asn Met Pro Asp Leu Pro Gln Asp Lys Pro
            420                 425                 430
Thr Pro Glu Glu His Gly Pro Gly Ile Asp Ile Phe Thr Pro Gly Lys
            435                 440                 445
Pro Gly Glu Tyr Asp Leu Glu Gly Gly Ile Trp Glu Asp Glu Asp Ala
            450                 455                 460
Arg Asn Phe Tyr Glu Asn Leu Ile Asp Leu Lys Ala Phe Val Pro Ala
465                 470                 475                 480
Ile Leu Phe Lys Asp Asn Glu Lys Ser Cys Gln Asn Lys Glu Ser Asn
            485                 490                 495
Lys Asp Asp Thr Lys Glu Ala Lys Glu Ser Lys Glu Asn Lys Glu Val
            500                 505                 510
Ser Ser Pro Asp Asp Leu Glu Leu Glu Leu Glu Asn Leu Glu Ile Asn
            515                 520                 525
Asp Asp Thr Leu Glu Leu Glu Gly Gly Asp Glu Ala Glu Asp Leu Thr
            530                 535                 540
Lys Lys Leu Leu Asp Glu Gln Glu Gln Glu Asp Glu Glu Ala Ser Thr
545                 550                 555                 560
Gly Ser His Leu Lys Leu Ile Val Asp Ala Phe Leu Gln Gln Leu Pro
            565                 570                 575
Asn Cys Val Asn Arg Asp Leu Ile Asp Lys Ala Ala Met Asp Phe Cys
            580                 585                 590
Met Asn Met Asn Thr Lys Ala Asn Arg Lys Lys Leu Val Arg Ala Leu
            595                 600                 605
Phe Ile Val Pro Arg Gln Arg Leu Asp Leu Leu Pro Phe Tyr Ala Arg
610                 615                 620
Leu Val Ala Thr Leu His Pro Cys Met Ser Asp Val Ala Glu Asp Leu
625                 630                 635                 640
Cys Ser Met Leu Arg Gly Asp Phe Arg Phe His Val Arg Lys Lys Asp
            645                 650                 655
Gln Ile Asn Ile Glu Thr Lys Asn Lys Thr Val Arg Phe Ile Gly Glu
            660                 665                 670
Leu Thr Lys Phe Lys Met Phe Thr Lys Asn Asp Thr Leu His Cys Leu
            675                 680                 685
Lys Met Leu Leu Ser Asp Phe Ser His His Ile Glu Met Ala Cys
            690                 695                 700
Thr Leu Leu Glu Thr Cys Gly Arg Phe Leu Phe Arg Ser Pro Glu Ser
705                 710                 715                 720
His Leu Arg Thr Ser Val Leu Leu Glu Gln Met Met Arg Lys Lys Gln
            725                 730                 735
Ala Met His Leu Asp Ala Arg Tyr Val Thr Met Val Glu Asn Ala Tyr
            740                 745                 750
Tyr Tyr Cys Asn Pro Pro Ala Glu Lys Thr Val Lys Lys Arg
            755                 760                 765
Pro Pro Leu Gln Glu Tyr Val Arg Lys Leu Leu Tyr Lys Asp Leu Ser
```

```
                770             775             780
Lys Val Thr Thr Glu Lys Val Leu Arg Gln Met Arg Lys Leu Pro Trp
785             790             795             800

Gln Asp Gln Glu Val Lys Asp Tyr Val Ile Cys Cys Met Ile Asn Ile
                805             810             815

Trp Asn Val Lys Tyr Asn Ser Ile His Cys Val Ala Asn Leu Leu Ala
                820             825             830

Gly Leu Val Leu Tyr Gln Glu Asp Val Gly Ile His Val Val Asp Gly
                835             840             845

Val Leu Glu Asp Ile Arg Leu Gly Met Glu Val Asn Gln Pro Lys Phe
850             855             860

Asn Gln Arg Arg Ile Ser Ser Ala Lys Phe Leu Gly Glu Leu Tyr Asn
865             870             875             880

Tyr Arg Met Val Glu Ser Ala Val Ile Phe Arg Thr Leu Tyr Ser Phe
                885             890             895

Thr Ser Phe Gly Val Asn Pro Asp Gly Ser Pro Ser Ser Leu Asp Pro
                900             905             910

Pro Glu His Leu Phe Arg Ile Arg Leu Val Cys Thr Ile Leu Asp Thr
                915             920             925

Cys Gly Gln Tyr Phe Asp Arg Gly Ser Ser Lys Arg Lys Leu Asp Cys
                930             935             940

Phe Leu Val Tyr Phe Gln Arg Tyr Val Trp Trp Lys Lys Ser Leu Glu
945             950             955             960

Val Trp Thr Lys Asp His Pro Phe Pro Ile Asp Ile Asp Tyr Met Ile
                965             970             975

Ser Asp Thr Leu Glu Leu Leu Arg Pro Lys Ile Lys Leu Cys Asn Ser
                980             985             990

Leu Glu Glu Ser Ile Arg Gln Val Gln Asp Leu Glu Arg Glu Phe Leu
                995             1000            1005

Ile Lys Leu Gly Leu Val Asn Asp Lys Asp Ser Lys Asp Ser Met
    1010            1015            1020

Thr Glu Gly Glu Asn Leu Glu Glu Asp Glu Glu Glu Glu Gly
    1025            1030            1035

Gly Ala Glu Thr Glu Glu Gln Ser Gly Asn Glu Ser Glu Val Asn
    1040            1045            1050

Glu Pro Glu Glu Glu Gly Ser Asp Asn Asp Asp Glu Gly
    1055            1060            1065

Glu Glu Glu Glu Glu Glu Asn Thr Asp Tyr Leu Thr Asp Ser Asn
    1070            1075            1080

Lys Glu Asn Glu Thr Asp Glu Glu Asn Thr Glu Val Met Ile Lys
    1085            1090            1095

Gly Gly Gly Leu Lys His Val Pro Cys Val Glu Asp Glu Asp Phe
    1100            1105            1110

Ile Gln Ala Leu Asp Lys Met Met Leu Glu Asn Leu Gln Gln Arg
    1115            1120            1125

Ser Gly Glu Ser Val Lys Val His Gln Leu Asp Val Ala Ile Pro
    1130            1135            1140

Leu His Leu Lys Ser Gln Leu Arg Lys Gly Pro Pro Leu Gly Gly
    1145            1150            1155

Gly Glu Gly Glu Ala Glu Ser Ala Asp Thr Met Pro Phe Val Met
    1160            1165            1170

Leu Thr Arg Lys Gly Asn Lys Gln Gln Phe Lys Ile Leu Asn Val
    1175            1180            1185
```

| Pro | Met | Ser | Ser | Gln | Leu | Ala | Ala | Asn | His | Trp | Asn | Gln | Gln | Gln |
|-----|-----|-----|-----|-----|-----|-----|-----|-----|-----|-----|-----|-----|-----|-----|
| 1190 | | | | 1195 | | | | | 1200 | | | | | |

| Ala | Glu | Gln | Glu | Glu | Arg | Met | Arg | Met | Lys | Lys | Leu | Thr | Leu | Asp |
|-----|-----|-----|-----|-----|-----|-----|-----|-----|-----|-----|-----|-----|-----|-----|
| 1205 | | | | | 1210 | | | | | 1215 | | | | |

| Ile | Asn | Glu | Arg | Gln | Glu | Gln | Glu | Asp | Tyr | Gln | Glu | Met | Leu | Gln |
|-----|-----|-----|-----|-----|-----|-----|-----|-----|-----|-----|-----|-----|-----|-----|
| 1220 | | | | | 1225 | | | | | 1230 | | | | |

| Ser | Leu | Ala | Gln | Arg | Pro | Ala | Pro | Ala | Asn | Thr | Asn | Arg | Glu | Arg |
|-----|-----|-----|-----|-----|-----|-----|-----|-----|-----|-----|-----|-----|-----|-----|
| 1235 | | | | | 1240 | | | | | 1245 | | | | |

| Arg | Pro | Arg | Tyr | Gln | His | Pro | Lys | Gly | Ala | Pro | Asn | Ala | Asp | Leu |
|-----|-----|-----|-----|-----|-----|-----|-----|-----|-----|-----|-----|-----|-----|-----|
| 1250 | | | | | 1255 | | | | | 1260 | | | | |

| Ile | Phe | Lys | Thr | Gly | Gly | Arg | Arg | Arg |
|-----|-----|-----|-----|-----|-----|-----|-----|-----|
| 1265 | | | | | 1270 | | | |

```
<210> SEQ ID NO 5
<211> LENGTH: 1359
<212> TYPE: DNA
<213> ORGANISM: Homo sapiens

<400> SEQUENCE: 5
atgctgtcgg ccctagaagt gcagttccac cgcgactcgc agcagcagga ggctgagacg      60
ccgccaactt cgtcctccgg ttgcgggggc ggtgcgggca aacctcgcga ggagaagagg     120
acggccctga gcaaggtggt catccgccgc ctgcctccgg gctcaccaa ggagcagctg      180 gaggagcagc tgcgcccgct gccagcacac gactacttcg agttcttcgc cgccgacctg    240
agtctttatc ctcatctcta ctcaagagca tacattaatt ttaggaatcc tgatgacatc     300 cttctttta gagatcgttt tgatggatat atcttccttg acagcaaagg cctagaatat     360
cctgcagtgg tagagtttgc tccattccag aagatagcca aaaagaagct gagaaaaaaa     420
gatgccaaga ctggaagcat cgaagatgat ccagaatata gaagtttttt agaaacctac     480
tgtgtggagg aagagaagac cagtgccaac cctgagactc tgctggggga gatggaggcg    540
aagacaagag agctcattgc tagaagaacc acacctcttt tggaatatat taaaaataga     600
aaattagaaa gcagagaat tcgagaagag aagcgagaag aacggaggag agagagtta     660 gaaaagaaac gtttgcggga gaggaaaaa agaagaagaa gaagaagaa agatgcaaa       720 aaaaagaga cagataaaca gaagaaaatt gcagagaaag aagtaaggat taagcttctt     780
aagaaaccag aaaagggaga ggaaccaacc acagagaaac caaagaaag aggagagg       840 attgatactg gaggtggcaa gcaggaatcc tgtgcccccg gtgcagtcgt aaaagccagg    900
cccatggaag gctcgctgga ggagccccag gagacgtcac acagcggcag tgataagag    960 cacagggatg tggagagatc tcaagaacaa gaatctgaag cacaaagata ccatgtggat  1020
gacggcagga ggcacagagc tcaccacgag cctgaacggc tttccagaag gagtgaggat    1080
gagcagagat gggggaaagg acctggccaa gacagaggga gaaggggag ccaggacagc    1140 ggggctccgg ggaggccat ggagagactg gaagagcgc aaaggtgtga cgacagtcca    1200
gcacccagaa aagagcgact ggcaaacaag gaccggccag ccttgcagct gtatgatcca   1260
ggagctcgct tccgagcgcg agagtgtggc ggaaacagga ggatctgcaa ggcagaaggt   1320
tcggggactg gtcctgagaa gagggaagag gcagagtga                          1359

<210> SEQ ID NO 6
<211> LENGTH: 452
<212> TYPE: PRT
<213> ORGANISM: Homo sapiens
```

<400> SEQUENCE: 6

```
Met Leu Ser Ala Leu Glu Val Gln Phe His Arg Asp Ser Gln Gln
1               5                   10                  15

Glu Ala Glu Thr Pro Pro Thr Ser Ser Gly Cys Gly Gly Gly Ala
                20                  25                  30

Gly Lys Pro Arg Glu Lys Arg Thr Ala Leu Ser Lys Val Val Ile
                35                  40                  45

Arg Arg Leu Pro Pro Gly Leu Thr Lys Glu Gln Leu Glu Glu Leu
50                  55                  60

Arg Pro Leu Pro Ala His Asp Tyr Phe Glu Phe Phe Ala Ala Asp Leu
65                  70                  75                  80

Ser Leu Tyr Pro His Leu Tyr Ser Arg Ala Tyr Ile Asn Phe Arg Asn
                85                  90                  95

Pro Asp Asp Ile Leu Leu Phe Arg Asp Arg Phe Asp Gly Tyr Ile Phe
                100                 105                 110

Leu Asp Ser Lys Gly Leu Glu Tyr Pro Ala Val Val Glu Phe Ala Pro
                115                 120                 125

Phe Gln Lys Ile Ala Lys Lys Lys Leu Arg Lys Lys Asp Ala Lys Thr
130                 135                 140

Gly Ser Ile Glu Asp Asp Pro Glu Tyr Lys Lys Phe Leu Glu Thr Tyr
145                 150                 155                 160

Cys Val Glu Glu Glu Lys Thr Ser Ala Asn Pro Glu Thr Leu Leu Gly
                165                 170                 175

Glu Met Glu Ala Lys Thr Arg Glu Leu Ile Ala Arg Arg Thr Thr Pro
                180                 185                 190

Leu Leu Glu Tyr Ile Lys Asn Arg Lys Leu Glu Lys Gln Arg Ile Arg
                195                 200                 205

Glu Glu Lys Arg Glu Glu Arg Arg Arg Glu Leu Gly Lys Lys Arg
                210                 215                 220

Leu Arg Glu Glu Glu Lys Arg Arg Arg Glu Glu Arg Cys Lys
225                 230                 235                 240

Lys Lys Glu Thr Asp Lys Gln Lys Lys Ile Ala Glu Lys Val Arg
                245                 250                 255

Ile Lys Leu Leu Lys Lys Pro Glu Lys Gly Glu Pro Thr Thr Glu
                260                 265                 270

Lys Pro Lys Glu Arg Gly Glu Glu Ile Asp Thr Gly Gly Lys Gln
                275                 280                 285

Glu Ser Cys Ala Pro Gly Ala Val Val Lys Ala Arg Pro Met Glu Gly
290                 295                 300

Ser Leu Glu Glu Pro Gln Glu Thr Ser His Ser Gly Ser Asp Lys Glu
305                 310                 315                 320

His Arg Asp Val Glu Arg Ser Gln Glu Gln Ser Glu Ala Gln Arg
                325                 330                 335

Tyr His Val Asp Asp Gly Arg Arg His Arg Ala His His Glu Pro Glu
                340                 345                 350

Arg Leu Ser Arg Arg Ser Glu Asp Glu Gln Arg Trp Gly Lys Gly Pro
                355                 360                 365

Gly Gln Asp Arg Gly Lys Lys Gly Ser Gln Asp Ser Gly Ala Pro Gly
370                 375                 380

Glu Ala Met Glu Arg Leu Gly Arg Ala Gln Arg Cys Asp Asp Ser Pro
385                 390                 395                 400

Ala Pro Arg Lys Glu Arg Leu Ala Asn Lys Asp Arg Pro Ala Leu Gln
                405                 410                 415
```

Leu Tyr Asp Pro Gly Ala Arg Phe Arg Ala Arg Glu Cys Gly Gly Asn
                420                 425                 430

Arg Arg Ile Cys Lys Ala Glu Gly Ser Gly Thr Gly Pro Glu Lys Arg
        435                 440                 445

Glu Glu Ala Glu
    450

<210> SEQ ID NO 7
<211> LENGTH: 10986
<212> TYPE: DNA
<213> ORGANISM: Homo sapiens

<400> SEQUENCE: 7

| | | | | | |
|---|---|---|---|---|---|
| atgagccgca | gagccccggg | gtctcggctg | agcagcggcg | gcggcggcgg | cggcaccaag | 60 |
| tatccgcgga | gctggaatga | ctggcaaccc | agaactgata | gtgcatcagc | cgacccagat | 120 |
| aatttaaaat | attcttcatc | cagagataga | ggtggttctt | cctcttatgg | actgcaacct | 180 |
| tcaaattcag | ctgtggtgtc | tcggcaaagg | cacgatgata | ccagagtcca | cgctgacata | 240 |
| cagaatgacg | aaaagggtgg | ctacagtgtc | aatggaggat | ctggggaaaa | tacttatggt | 300 |
| cggaagtcgt | tggggcaaga | gctgagggtt | aacaatgtga | ccagccctga | gttcaccagt | 360 |
| gttcagcatg | gcagtcgtgc | tttagccacc | aaagacatga | ggaaatcaca | ggagagatcg | 420 |
| atgtcttatt | ctgatgagtc | tcgactgtcg | aatcttcttc | ggaggatcac | ccgggaagac | 480 |
| gacagagacc | gaagattggc | tactgtaaag | cagttgaaag | aatttattca | gcaaccagaa | 540 |
| aataagctgg | tactagttaa | acaattggat | aatatcttgg | ctgctgtaca | tgacgtgctt | 600 |
| aatgaaagta | gcaaattgct | tcaggagttg | agacaggagg | gagcttgctg | tcttggcctt | 660 |
| ctttgtgctt | ctctgagcta | tgaggctgag | aagatcttca | agtggatttt | tagcaaattt | 720 |
| agctcatctg | caaaagatga | agttaaactc | ctctacttat | gtgccaccta | caaagcacta | 780 |
| gagactgtag | agaaaagaa | agccttttca | tctgtaatgc | agcttgtaat | gaccagcctg | 840 |
| cagtctattc | ttgaaaatgt | ggatacacca | gaattgcttt | gtaaatgtgt | taagtgcatt | 900 |
| cttttggtgg | ctcgatgtta | ccctcatatt | ttcagcacta | attttaggga | tacagttgat | 960 |
| atattagttg | gatggcatat | agatcatact | cagaaaacctt | cgctcacgca | gcaggtatct | 1020 |
| gggtggttgc | agagtttgga | gccattttgg | gtagctgatc | ttgcatttc | tactactctt | 1080 |
| cttggtcagt | ttctggaaga | catggaagca | tatgctgagg | acctcagcca | tgtggcctct | 1140 |
| ggggaatcag | tggatgaaga | gtccctcct | ccatcagtgt | cattaccaaa | gctggctgca | 1200 |
| cttctccggg | tatttagtac | tgtggtgagg | agcattgggg | aacgcttcag | cccaattcgg | 1260 |
| ggtcctccaa | ttactgaggc | atatgtaaca | gatgttctgt | acagagtaat | gagatgtgtg | 1320 |
| acggctgcaa | accaggtgtt | ttttctgag | gctgtgttga | cagctgctaa | tgagtgtgtt | 1380 |
| ggtgttttgc | tcggcagctt | ggatcctagc | atgactatac | attgtgacat | ggtcattaca | 1440 |
| tatggattag | accaactgga | gaattgccag | acttgtggta | ccgattatat | catctcagtc | 1500 |
| ttgaatttac | tcacgctgat | tgttgaacag | ataaatacga | aactgccatc | atcatttgta | 1560 |
| gaaaaactgt | ttataccatc | atctaaacta | ctattcttgc | gttatcataa | agaaaaagag | 1620 |
| gttgttgctg | tagcccatgc | tgtttatcaa | gcagtgctca | gcttgaagaa | tattcctgtt | 1680 |
| ttggagactg | cctataagtt | aatattggga | gaaatgactt | gtgccctaaa | caacctccta | 1740 |
| cacagtctac | aacttcctga | ggcctgttct | gaaataaaac | atgaggcttt | taagaatcat | 1800 |
| gtgttcaatg | tagacaatgc | aaaatttgta | gttatatttg | acctcagtgc | cctgactaca | 1860 |

```
attggaaatg ccaaaaactc actaataggg atgtgggcgc tatctccaac tgtctttgca   1920
cttctgagta agaatctgat gattgtgcac agtgacctgg ctgttcactt ccctgccatt   1980
cagtatgctg tgctctacac attgtattct cattgtacca ggcatgatca ctttatctct   2040
agtagcctca gttcttcctc tccttctttg tttgatggag ctgtgattag cactgtaact   2100
acggctacaa agaaacattt ctcaattata ttaaatcttc tgggaatatt acttaagaaa   2160
gataaccttc accaggacac gaggaaactg ttaatgactt gggctttgga agcagctgtt   2220
ttaatgaaga agtctgaaac atacgcacct ttattctctc ttccgtcttt ccataaattt   2280
tgcaaaggcc tttagccaa cactctcgtt gaagatgtga atatctgtct gcaggcatgc   2340
agcagtctac atgctctgtc ctcttccttg ccagatgatc ttttacagag atgtgtcgat   2400
gtttgccgtg ttcaactagt gcacagtgga actcgtattc gacaagcatt tggaaaactg   2460
ttgaaatcaa ttcctttaga tgttgtccta agcaataaca atcacacaga aattcaagaa   2520
atttctttag cattaagaag tcacatgagt aaagcaccaa gtaatacatt ccaccccaa    2580 gatttctctg atgttattag ttttatttgg tatgggaact ctcatagaac agggaaggac   2640
aattggttgg aaagactgtt ctatagctgc cagagactgg ataagcgtga ccagtcaaca   2700
attccacgca atctcctgaa gacagatgct gtcctttggc agtgggccat atgggaagct   2760
gcacaattca ctgttctttc taagctgaga accccactgg gcagagctca agacaccttc   2820
cagacaattg aaggtatcat tcgaagtctc gcagctcaca cattaaaccc tgatcaggat   2880
gttagtcagt ggacaactgc agacaatgat gaaggccatg gtaacaacca acttagactt   2940
gttcttcttc tgcagtatct ggaaaatctg gagaaattaa tgtataatgc atacgaggga   3000
tgtgctaatg cattaacttc acctcccaag gtcattagaa cttttttcta taccaatcgc   3060
caaacttgtc aggactggct aacgcggatt cgactctcca tcatgagggt aggattgttg   3120
gcaggccagc ctgcagtgac agtgagacat ggctttgact tgcttacaga gatgaaaaca   3180
accagcctat ctcaggggaa tgaattggaa gtaaccatta tgatggtggt agaagcatta   3240
tgtgaacttc attgtcctga agctatacag ggaattgctg tctggtcatc atctattgtt   3300
ggaaaaaatc ttctgtggat taactcagtg gctaacagg ctgaagggag gtttgaaaag   3360
gcctctgtgg agtaccagga acacctgtgt gccatgacag gtgttgattg ctgcatctcc   3420
agctttgaca aatcggtgct cacccttagcc aatgctgggc gtaacagtgc cagcccgaaa   3480
cattctctga atggtgaatc cagaaaaact gtgctgtcca accgactga ctcttcccct    3540 gaggttataa attatttagg aaataaagca tgtgagtgct acatctcaat tgccgattgg   3600
gctgctgtgc aggaatggca gaacgctatc catgacttga aaagagtac cagtagcact   3660 tccctcaacc tgaaagctga cttcaactat ataaaatcat taagcagctt tgagtctgga   3720
aaatttgttg aatgtaccga gcagttagaa ttgttaccag gagaaaatat caatctactt   3780
gctggaggat caaagaaaa aatagacatg aaaaaactgc ttcctaacat gttaagtccg   3840
gatccgaggg aacttcagaa atccattgaa gttcaattgt taagaagttc tgtttgtttg   3900
gcaactgctt taaacccgat agaacaagat cagaagtggc agtctataac tgaaaatgtg   3960
gtaaagtact tgaagcaaac atcccgcatc gctattggac ctctgagact ttctacttta   4020
acagtttcac agtctttgcc agttctaagt accttgcagc tgtattgctc atctgctttg   4080
gagaacacag tttctaacag acttcaaca gaggactgtc ttattccact cttcagtgaa   4140
gctttacgtt catgtaaaca gcatgacgtg aggccatgga tgcaggcatt aagtatact    4200
```

```
atgtaccaga atcagttgtt ggagaaaatt aaagaacaaa cagtcccaat tagaagccat    4260
ctcatggaat taggtctaac agcagcaaaa tttgctagaa aacgagggaa tgtgtccctt    4320
gcaacaagac tgctggcaca gtgcagtgaa gttcagctgg aaagaccac cactgcacag     4380 gatttagtcc aacattttaa aaaactatca acccaaggtc aagtggatga aaaatggggg    4440
cccgaacttg atattgaaaa aaccaaattg ctttatacag caggccagtc aacacatgca    4500
atggaaatgt tgagttcttg tgccatatct ttctgcaagt ctgtgaaagc tgaatatgca    4560
gttgctaaat caattctgac actggctaaa tggatccagg cagaatggaa agagatttca    4620
ggacagctga acaggttta cagagctcag caccaacaga acttcacagg tctttctact     4680
ttgtctaaaa acatactcac tctaatagaa ctgccatctg ttaatacgat ggaagaagag    4740
tatcctcgga tcgagagtga atctacagtg catattggag ttggagaacc tgacttcatt    4800
ttgggacagt tgtatcacct gtcttcagta caggcacctg aagtagccaa atcttgggca    4860
gcgttggcca gctgggctta taggtggggc agaaaggtgg ttgacaatgc cagtcaggga    4920
gaaggtgttc gtctgctgcc tagagaaaaa tctgaagttc agaatctact tccagacact    4980
ataactgagg aagagaaaga gagaatatat ggtattcttg acaggctgt gtgtcggccg      5040 gcggggattc aggatgaaga tataacactt cagataactg agagtgaaga caacgaagaa    5100
gatgacatgg ttgatgttat ctggcgtcag ttgatatcaa gctgcccatg gctttcagaa    5160
cttgatgaaa gtgcaactga aggagttatt aaagtgtgga ggaaagttgt agatagaata    5220
ttcagcctgt acaaactctc ttgcagtgca tactttactt tccttaaact caacgctggt    5280
caaattcctt tagatgagga tgaccctagg ctgcatttaa gtcacagagt ggaacagagc    5340
actgatgaca tgattgtgat ggccacattg cgcctgctgc ggttgctcgt gaagcatgct    5400
ggtgagcttc ggcagtatct ggagcacggc ttggagacaa cacccactgc accatggaga    5460
ggaattattc cgcaactttt ctcacgctta aaccaccctg aagtgtatgt gcgccaaagt    5520
atttgtaacc ttctctgccg tgtggctcaa gattccccac atctcatatt gtatcctgca    5580
atagtgggta ccatatcgct tagtagtgaa tcccaggctt caggaaataa attttccact    5640
gcaattccaa ctttacttgg caatattcaa ggagaagaat tgctggtttc tgaatgtgag    5700
ggaggaagtc ctcctgcatc tcaggatagc aataaggatg aacctaaaag tggattaaat    5760
gaagaccaag ccatgatgca ggattgttac agcaaaattg tagataagct gtcctctgca    5820
aaccccacca tggtattaca ggttcagatg ctcgtggctg aactgcgcag ggtcactgtg    5880
ctctgggatt agctctggct gggagttttg ctgcaacaac acatgtatgt cctgagacga    5940
attcagcagc ttgaagatga ggtgaagaga gtccagaaca caacaccctt acgcaaagaa    6000
gagaaaattg caatcatgag ggagaagcac acagctttga tgaagcccat cgtatttgct    6060
ttggagcatg tgaggagtat cacagcggct cctgcagaaa cacctcatga aaaatggttt    6120
caggataact atggtgatgc cattgaaaat gccctagaaa aactgaagac tccattgaac    6180
cctgcaaagc ctgggagcag ctggattcca tttaaagaga taatgctaag tttgcaacag    6240
agagcacaga aacgtgcaag ttacatcttg cgtcttgaag aaatcagtcc atggttggct    6300
gccatgacta acactgaaat tgctcttcct ggggaagtct cagccagaga cactgtcaca    6360
atccatagtg tgggcggaac catcacaatc ttaccgacta aaaccaagcc aaagaaactt    6420
ctctttcttg gatcagatgg gaagagctat ccttatcttt tcaaaggact ggaggattta    6480
catctggatg agagaataat gcagttccta tctattgtga ataccatgtt tgctacaatt    6540
aatcgccaag aaacaccccg gttccatgct cgacactatt ctgtaacacc actaggaaca    6600
```

```
agatcaggac taatccagtg ggtagatgga gccacaccct tatttggtct ttacaaacga    6660
tggcaacaac gggaagctgc cttacaagca caaaaggccc aagattccta ccaaactcct    6720
cagaatcctg gaattgtacc ccgtcctagt gaactttatt acagtaaaat tggccctgct    6780
ttgaaaacag ttgggcttag cctggatgtg tcccgtcggg attggcctct tcatgtaatg    6840
aaggcagtat tggaagagtt aatggaggcc acaccccga atctccttgc caaagagctc    6900
tggtcatctt gcacaacacc tgatgaatgg tggagagtta cgcagtctta tgcaagatct    6960
actgcagtca tgtctatggt tggatacata attggccttg agacagaca tctggataat    7020 gttcttatag atatgacgac tggagaagtt gttcacatag attacaatgt ttgctttgaa    7080
aaaggtaaaa gccttagagt tcctgagaaa gtacctttc gaatgacaca aaacattgaa    7140
acagcactgg gtgtaactgg agtagaaggt gtatttaggc tttcatgtga gcaggtttta    7200
cacattatgc ggcgtggcag agagaccctg ctgacgctgc tggaggcctt tgtgtacgac    7260
cctctggtgg actggacagc aggaggcgag gctgggtttg ctggtgctgt ctatggtgga    7320
ggtggccagc aggccgagag caagcagagc aagagagaga tggagcgaga gatcacccgc    7380
agcctgtttt cttctagagt agctgagatt aaggtgaact ggtttaagaa tagagatgag    7440
atgctggttg tgcttcccaa gttggacggt agcttagatg aatacctaag cttgcaagag    7500
caactgacag atgtggaaaa actgcagggc aaactactgg aggaaataga gtttctagaa    7560
ggagctgaag gggtggatca tccttctcat actctgcaac acaggtattc tgagcacacc    7620
caactacaga ctcagcaaag agctgttcag gaagcaatcc aggtgaagct gaatgaattt    7680
gaacaatgga taacacatta tcaggctgca ttcaataatt tagaagcaac acagcttgca    7740
agcttgcttc aagagataag cacacaaatg gaccttggtc ctccaagtta cgtgccagca    7800
acagcctttc tgcagaatgc tggtcaggcc cacttgatta gccagtgcga gcagctggag    7860
ggggaggttg gtgctctcct gcagcagagg cgctccgtgc tccgtggctg tctggagcaa    7920
ctgcatcact atgcaaccgt ggccctgcag tatccgaagg ccatatttca gaaacatcga    7980
attgaacagt ggaagacctg gatggaagag ctcatctgta acaccacagt agagcgttgt    8040
caagagctct ataggaaata tgaaatgcaa tatgctcccc agccacccc aacagtgtgt    8100 cagttcatca ctgccactga aatgacccctg cagcgatacg cagcagacat caacagcaga    8160
cttattagac aagtggaacg cttgaaacag gaagctgtca ctgtgccagt ttgtgaagat    8220
cagttgaaag aaattgaacg ttgcattaaa gttttccttc atgagaatgg agaagaagga    8280
tctttgagtc tagcaagtgt tattatttct gcccttttgta cccttacaag gcgtaacctg    8340
atgatggaag gtgcagcgtc aagtgctgga gaacagctgg ttgatctgac ttctcgggat    8400
ggagcctggt tcttgaggga actctgcagt atgagcggaa acgtcacctg cttggttcag    8460
ttactgaagc agtgccacct ggtgccacag gacttagata tcccgaaccc catggaagcg    8520
tctgagacag ttcacttagc caatggagtg tatacctcac ttcaggaatt gaattcgaat    8580
ttccggcaaa tcatatttcc agaagcactt cgatgtttaa tgaaagggga atacacgtta    8640
gaaagtatgc tgcatgaact ggacggtctt attgagcaga ccaccgatgg cgttcccctg    8700
cagactctag tggaatctct tcaggcctac ttaagaaacg cagctatggg actggaagaa    8760
gaaacacatg ctcattacat cgatgttgcc agactactac atgctcagta cggtgaatta    8820
atccaaccga gaaatggttc agttgatgaa cacccaaaa tgtcagctgg ccagatgctt    8880
ttggtagcat tcgatggcat gtttgctcaa gttgaaactg ctttcagctt attagttgaa    8940
```

| | | |
|---|---|---|
| aagttgaaca agatggaaat tcccatagct tggcgaaaga ttgacatcat aagggaagcc | 9000 |
| aggagtactc aagttaattt ttttgatgat gataatcacc ggcaggtgct agaagagatt | 9060 |
| ttctttctaa aaagactaca gactattaag gagttcttca ggctctgtgg tacctttct | 9120 |
| aaaacattgt caggatcaag ttcacttgaa gatcagaata ctgtgaatgg gcctgtacag | 9180 |
| attgtcaatg tgaaacccct ttttagaaac tcttgtttca gtgaagacca aatggccaaa | 9240 |
| cctatcaagg cattcacagc tgactttgtg aggcagctct tgatagggct acccaaccaa | 9300 |
| gccctcggac tcacactgtg cagttttatc agtgctctgg gtgtagacat cattgctcaa | 9360 |
| gtagaggcaa aggactttgg tgccgaaagc aaagtttctg ttgatgatct ctgtaagaaa | 9420 |
| gcggtggaac ataacatcca gatagggaag ttctctcagc tggttatgaa cagggcaact | 9480 |
| gtgttagcaa gttcttacga cactgcctgg aagaagcatg acttggtgcg aaggctagaa | 9540 |
| accagtattt cttcttgtaa gacaagcctg cagcgggttc agctgcatat tgccatgttt | 9600 |
| cagtggcaac atgaagatct acttatcaat agaccacaag ccatgtcagt cacacctccc | 9660 |
| ccacggtctg ctatcctaac cagcatgaaa agaagctgc atacctgag ccagattgaa | 9720 |
| acttctattg caacagttca ggagaagcta gctgcacttg aatcaagtat tgaacagcga | 9780 |
| ctcaagtggg caggtggtgc caaccctgca ttggcccctg tactacaaga ttttgaagca | 9840 |
| acgatagctg aaagaagaaa tcttgtcctt aaagagagcc aaagagcaag tcaggtcaca | 9900 |
| tttctctgca gcaatatcat tcattttgaa agtttacgaa caagaactgc agaagcctta | 9960 |
| aacctggatg cggcgttatt tgaactaatc aagcgatgtc agcagatgtg ttcgtttgca | 10020 |
| tcacagttta acgttcagt gtctgagtta gagcttcgtt tattacagag agtggacact | 10080 |
| ggtcttgaac atcctattgg cagctctgaa tggcttttgt cagcacacaa acagttgacc | 10140 |
| caggatatgt ctactcagag ggcaattcag acagagaaag agcagcagat agaaacggtc | 10200 |
| tgtgaaacaa ttcagaatct ggttgataat ataaagactg tgctcactgg tcataaccga | 10260 |
| cagcttggaa tgtcaaaca tctcttgaaa gctatggcta aggatgaaga agctgctctg | 10320 |
| gcagatggtg aagatgttcc ctatgagaac agtgttaggc agttttgg tgaatataaa | 10380 |
| tcatggcaag acaacattca aacagttcta tttacattag tccaggctat gggtcaggtt | 10440 |
| cgaagtcaag aacacgttga atgctccag gaaatcactc ccaccttgaa agaactgaaa | 10500 |
| acacaaagtc agagtatcta taataattta gtgagttttg catcacccctt agtcaccgat | 10560 |
| gcaacaaatg aatgttcgag tccaacgtca tctgctactt atcagccatc cttcgctgca | 10620 |
| gcagtccgga gtaacactgg ccagaagact cagcctgatg tcatgtcaca gaatgctaga | 10680 |
| aagctgatcc agaaaaatct tgctacatca gctgatactc caccaagcac cgttccagga | 10740 |
| actggcaaga gtgttgcttg tagtcctaaa aaggcagtca gagaccctaa aactgggaaa | 10800 |
| gcggtgcaag agagaaactc ctatgcagtg agtgtgtgga agagagtgaa agccaagtta | 10860 |
| gagggccgag atgttgatcc gaataggagg atgtcagttg ctgaacaggt tgactatgtc | 10920 |
| attaaggaag caactaatct agataacttg gctcagctgt atgaaggttg gacagcctgg | 10980 |
| gtgtga | 10986 |

<210> SEQ ID NO 8
<211> LENGTH: 3661
<212> TYPE: PRT
<213> ORGANISM: Homo sapiens

<400> SEQUENCE: 8

Met Ser Arg Arg Ala Pro Gly Ser Arg Leu Ser Ser Gly Gly Gly Gly

-continued

```
1               5                   10                  15
Gly Gly Thr Lys Tyr Pro Arg Ser Trp Asn Asp Trp Gln Pro Arg Thr
                20                  25                  30

Asp Ser Ala Ser Ala Asp Pro Asp Asn Leu Lys Tyr Ser Ser Ser Arg
                35                  40                  45

Asp Arg Gly Gly Ser Ser Tyr Gly Leu Gln Pro Ser Asn Ser Ala
            50                  55                  60

Val Val Ser Arg Gln Arg His Asp Asp Thr Arg Val His Ala Asp Ile
65                  70                  75                  80

Gln Asn Asp Glu Lys Gly Gly Tyr Ser Val Asn Gly Ser Gly Glu
                85                  90                  95

Asn Thr Tyr Gly Arg Lys Ser Leu Gly Gln Glu Leu Arg Val Asn Asn
                100                 105                 110

Val Thr Ser Pro Glu Phe Thr Ser Val Gln His Gly Ser Arg Ala Leu
                115                 120                 125

Ala Thr Lys Asp Met Arg Lys Ser Gln Glu Arg Ser Met Ser Tyr Ser
            130                 135                 140

Asp Glu Ser Arg Leu Ser Asn Leu Leu Arg Arg Ile Thr Arg Glu Asp
145                 150                 155                 160

Asp Arg Asp Arg Arg Leu Ala Thr Val Lys Gln Leu Lys Glu Phe Ile
                165                 170                 175

Gln Gln Pro Glu Asn Lys Leu Val Leu Val Lys Gln Leu Asp Asn Ile
                180                 185                 190

Leu Ala Ala Val His Asp Val Leu Asn Glu Ser Ser Lys Leu Leu Gln
            195                 200                 205

Glu Leu Arg Gln Glu Gly Ala Cys Cys Leu Gly Leu Leu Cys Ala Ser
            210                 215                 220

Leu Ser Tyr Glu Ala Glu Lys Ile Phe Lys Trp Ile Phe Ser Lys Phe
225                 230                 235                 240

Ser Ser Ser Ala Lys Asp Glu Val Lys Leu Leu Tyr Leu Cys Ala Thr
                245                 250                 255

Tyr Lys Ala Leu Glu Thr Val Gly Glu Lys Lys Ala Phe Ser Ser Val
                260                 265                 270

Met Gln Leu Val Met Thr Ser Leu Gln Ser Ile Leu Glu Asn Val Asp
            275                 280                 285

Thr Pro Glu Leu Leu Cys Lys Cys Val Lys Cys Ile Leu Leu Val Ala
            290                 295                 300

Arg Cys Tyr Pro His Ile Phe Ser Thr Asn Phe Arg Asp Thr Val Asp
305                 310                 315                 320

Ile Leu Val Gly Trp His Ile Asp His Thr Gln Lys Pro Ser Leu Thr
                325                 330                 335

Gln Gln Val Ser Gly Trp Leu Gln Leu Glu Pro Phe Trp Val Ala
            340                 345                 350

Asp Leu Ala Phe Ser Thr Thr Leu Leu Gly Gln Phe Leu Glu Asp Met
            355                 360                 365

Glu Ala Tyr Ala Glu Asp Leu Ser His Val Ala Ser Gly Glu Ser Val
            370                 375                 380

Asp Glu Asp Val Pro Pro Ser Val Ser Leu Pro Lys Leu Ala Ala
385                 390                 395                 400

Leu Leu Arg Val Phe Ser Thr Val Val Arg Ser Ile Gly Glu Arg Phe
                405                 410                 415

Ser Pro Ile Arg Gly Pro Pro Ile Thr Glu Ala Tyr Val Thr Asp Val
                420                 425                 430
```

```
Leu Tyr Arg Val Met Arg Cys Val Thr Ala Ala Asn Gln Val Phe Phe
        435                 440                 445

Ser Glu Ala Val Leu Thr Ala Ala Asn Glu Cys Val Gly Val Leu Leu
    450                 455                 460

Gly Ser Leu Asp Pro Ser Met Thr Ile His Cys Asp Met Val Ile Thr
465                 470                 475                 480

Tyr Gly Leu Asp Gln Leu Glu Asn Cys Gln Thr Cys Gly Thr Asp Tyr
                485                 490                 495

Ile Ile Ser Val Leu Asn Leu Leu Thr Leu Ile Val Glu Gln Ile Asn
                500                 505                 510

Thr Lys Leu Pro Ser Ser Phe Val Glu Lys Leu Phe Ile Pro Ser Ser
        515                 520                 525

Lys Leu Leu Phe Leu Arg Tyr His Lys Glu Lys Glu Val Val Ala Val
        530                 535                 540

Ala His Ala Val Tyr Gln Ala Val Leu Ser Leu Lys Asn Ile Pro Val
545                 550                 555                 560

Leu Glu Thr Ala Tyr Lys Leu Ile Leu Gly Glu Met Thr Cys Ala Leu
                565                 570                 575

Asn Asn Leu Leu His Ser Leu Gln Leu Pro Glu Ala Cys Ser Glu Ile
                580                 585                 590

Lys His Glu Ala Phe Lys Asn His Val Phe Asn Val Asp Asn Ala Lys
        595                 600                 605

Phe Val Val Ile Phe Asp Leu Ser Ala Leu Thr Thr Ile Gly Asn Ala
        610                 615                 620

Lys Asn Ser Leu Ile Gly Met Trp Ala Leu Ser Pro Thr Val Phe Ala
625                 630                 635                 640

Leu Leu Ser Lys Asn Leu Met Ile Val His Ser Asp Leu Ala Val His
                645                 650                 655

Phe Pro Ala Ile Gln Tyr Ala Val Leu Tyr Thr Leu Tyr Ser His Cys
                660                 665                 670

Thr Arg His Asp His Phe Ile Ser Ser Ser Leu Ser Ser Ser Ser Pro
        675                 680                 685

Ser Leu Phe Asp Gly Ala Val Ile Ser Thr Val Thr Thr Ala Thr Lys
        690                 695                 700

Lys His Phe Ser Ile Ile Leu Asn Leu Leu Gly Ile Leu Leu Lys Lys
705                 710                 715                 720

Asp Asn Leu Asn Gln Asp Thr Arg Lys Leu Leu Met Thr Trp Ala Leu
                725                 730                 735

Glu Ala Ala Val Leu Met Lys Lys Ser Glu Thr Tyr Ala Pro Leu Phe
                740                 745                 750

Ser Leu Pro Ser Phe His Lys Phe Cys Lys Gly Leu Leu Ala Asn Thr
        755                 760                 765

Leu Val Glu Asp Val Asn Ile Cys Leu Gln Ala Cys Ser Ser Leu His
        770                 775                 780

Ala Leu Ser Ser Ser Leu Pro Asp Asp Leu Leu Gln Arg Cys Val Asp
785                 790                 795                 800

Val Cys Arg Val Gln Leu Val His Ser Gly Thr Arg Ile Arg Gln Ala
                805                 810                 815

Phe Gly Lys Leu Leu Lys Ser Ile Pro Leu Asp Val Val Leu Ser Asn
                820                 825                 830

Asn Asn His Thr Glu Ile Gln Glu Ile Ser Leu Ala Leu Arg Ser His
        835                 840                 845
```

```
Met Ser Lys Ala Pro Ser Asn Thr Phe His Pro Gln Asp Phe Ser Asp
850                 855                 860

Val Ile Ser Phe Ile Leu Tyr Gly Asn Ser His Arg Thr Gly Lys Asp
865                 870                 875                 880

Asn Trp Leu Glu Arg Leu Phe Tyr Ser Cys Gln Arg Leu Asp Lys Arg
                885                 890                 895

Asp Gln Ser Thr Ile Pro Arg Asn Leu Leu Lys Thr Asp Ala Val Leu
                900                 905                 910

Trp Gln Trp Ala Ile Trp Glu Ala Gln Phe Thr Val Leu Ser Lys
                915                 920                 925

Leu Arg Thr Pro Leu Gly Arg Ala Gln Asp Thr Phe Gln Thr Ile Glu
930                 935                 940

Gly Ile Ile Arg Ser Leu Ala Ala His Thr Leu Asn Pro Asp Gln Asp
945                 950                 955                 960

Val Ser Gln Trp Thr Thr Ala Asp Asn Asp Glu Gly His Gly Asn Asn
                965                 970                 975

Gln Leu Arg Leu Val Leu Leu Gln Tyr Leu Glu Asn Leu Glu Lys
                980                 985                 990

Leu Met Tyr Asn Ala Tyr Glu Gly Cys Ala Asn Ala Leu Thr Ser Pro
                995                 1000                1005

Pro Lys Val Ile Arg Thr Phe Phe Tyr Thr Asn Arg Gln Thr Cys
    1010                1015                1020

Gln Asp Trp Leu Thr Arg Ile Arg Leu Ser Ile Met Arg Val Gly
    1025                1030                1035

Leu Leu Ala Gly Gln Pro Ala Val Thr Val Arg His Gly Phe Asp
    1040                1045                1050

Leu Leu Thr Glu Met Lys Thr Thr Ser Leu Ser Gln Gly Asn Glu
    1055                1060                1065

Leu Glu Val Thr Ile Met Met Val Val Glu Ala Leu Cys Glu Leu
    1070                1075                1080

His Cys Pro Glu Ala Ile Gln Gly Ile Ala Val Trp Ser Ser Ser
    1085                1090                1095

Ile Val Gly Lys Asn Leu Leu Trp Ile Asn Ser Val Ala Gln Gln
    1100                1105                1110

Ala Glu Gly Arg Phe Glu Lys Ala Ser Val Glu Tyr Gln Glu His
    1115                1120                1125

Leu Cys Ala Met Thr Gly Val Asp Cys Cys Ile Ser Ser Phe Asp
    1130                1135                1140

Lys Ser Val Leu Thr Leu Ala Asn Ala Gly Arg Asn Ser Ala Ser
    1145                1150                1155

Pro Lys His Ser Leu Asn Gly Glu Ser Arg Lys Thr Val Leu Ser
    1160                1165                1170

Lys Pro Thr Asp Ser Ser Pro Glu Val Ile Asn Tyr Leu Gly Asn
    1175                1180                1185

Lys Ala Cys Glu Cys Tyr Ile Ser Ile Ala Asp Trp Ala Ala Val
    1190                1195                1200

Gln Glu Trp Gln Asn Ala Ile His Asp Leu Lys Lys Ser Thr Ser
    1205                1210                1215

Ser Thr Ser Leu Asn Leu Lys Ala Asp Phe Asn Tyr Ile Lys Ser
    1220                1225                1230

Leu Ser Ser Phe Glu Ser Gly Lys Phe Val Glu Cys Thr Glu Gln
    1235                1240                1245

Leu Glu Leu Leu Pro Gly Glu Asn Ile Asn Leu Leu Ala Gly Gly
```

-continued

```
            1250                1255                1260
Ser Lys Glu Lys Ile Asp Met Lys Lys Leu Leu Pro Asn Met Leu
    1265                1270                1275
Ser Pro Asp Pro Arg Glu Leu Gln Lys Ser Ile Glu Val Gln Leu
    1280                1285                1290
Leu Arg Ser Ser Val Cys Leu Ala Thr Ala Leu Asn Pro Ile Glu
    1295                1300                1305
Gln Asp Gln Lys Trp Gln Ser Ile Thr Glu Asn Val Val Lys Tyr
    1310                1315                1320
Leu Lys Gln Thr Ser Arg Ile Ala Ile Gly Pro Leu Arg Leu Ser
    1325                1330                1335
Thr Leu Thr Val Ser Gln Ser Leu Pro Val Leu Ser Thr Leu Gln
    1340                1345                1350
Leu Tyr Cys Ser Ser Ala Leu Glu Asn Thr Val Ser Asn Arg Leu
    1355                1360                1365
Ser Thr Glu Asp Cys Leu Ile Pro Leu Phe Ser Glu Ala Leu Arg
    1370                1375                1380
Ser Cys Lys Gln His Asp Val Arg Pro Trp Met Gln Ala Leu Arg
    1385                1390                1395
Tyr Thr Met Tyr Gln Asn Gln Leu Leu Glu Lys Ile Lys Glu Gln
    1400                1405                1410
Thr Val Pro Ile Arg Ser His Leu Met Glu Leu Gly Leu Thr Ala
    1415                1420                1425
Ala Lys Phe Ala Arg Lys Arg Gly Asn Val Ser Leu Ala Thr Arg
    1430                1435                1440
Leu Leu Ala Gln Cys Ser Glu Val Gln Leu Gly Lys Thr Thr Thr
    1445                1450                1455
Ala Gln Asp Leu Val Gln His Phe Lys Lys Leu Ser Thr Gln Gly
    1460                1465                1470
Gln Val Asp Glu Lys Trp Gly Pro Glu Leu Asp Ile Glu Lys Thr
    1475                1480                1485
Lys Leu Leu Tyr Thr Ala Gly Gln Ser Thr His Ala Met Glu Met
    1490                1495                1500
Leu Ser Ser Cys Ala Ile Ser Phe Cys Lys Ser Val Lys Ala Glu
    1505                1510                1515
Tyr Ala Val Ala Lys Ser Ile Leu Thr Leu Ala Lys Trp Ile Gln
    1520                1525                1530
Ala Glu Trp Lys Glu Ile Ser Gly Gln Leu Lys Gln Val Tyr Arg
    1535                1540                1545
Ala Gln His Gln Gln Asn Phe Thr Gly Leu Ser Thr Leu Ser Lys
    1550                1555                1560
Asn Ile Leu Thr Leu Ile Glu Leu Pro Ser Val Asn Thr Met Glu
    1565                1570                1575
Glu Glu Tyr Pro Arg Ile Glu Ser Glu Ser Thr Val His Ile Gly
    1580                1585                1590
Val Gly Glu Pro Asp Phe Ile Leu Gly Gln Leu Tyr His Leu Ser
    1595                1600                1605
Ser Val Gln Ala Pro Glu Val Ala Lys Ser Trp Ala Ala Leu Ala
    1610                1615                1620
Ser Trp Ala Tyr Arg Trp Gly Arg Lys Val Val Asp Asn Ala Ser
    1625                1630                1635
Gln Gly Glu Gly Val Arg Leu Leu Pro Arg Glu Lys Ser Glu Val
    1640                1645                1650
```

```
Gln Asn Leu Leu Pro Asp Thr Ile Thr Glu Glu Lys Glu Arg
    1655                1660                1665

Ile Tyr Gly Ile Leu Gly Gln Ala Val Cys Arg Pro Ala Gly Ile
    1670                1675                1680

Gln Asp Glu Asp Ile Thr Leu Gln Ile Thr Glu Ser Glu Asp Asn
    1685                1690                1695

Glu Glu Asp Asp Met Val Asp Val Ile Trp Arg Gln Leu Ile Ser
    1700                1705                1710

Ser Cys Pro Trp Leu Ser Glu Leu Asp Glu Ser Ala Thr Glu Gly
    1715                1720                1725

Val Ile Lys Val Trp Arg Lys Val Val Asp Arg Ile Phe Ser Leu
    1730                1735                1740

Tyr Lys Leu Ser Cys Ser Ala Tyr Phe Thr Phe Leu Lys Leu Asn
    1745                1750                1755

Ala Gly Gln Ile Pro Leu Asp Glu Asp Pro Arg Leu His Leu
    1760                1765                1770

Ser His Arg Val Glu Gln Ser Thr Asp Asp Met Ile Val Met Ala
    1775                1780                1785

Thr Leu Arg Leu Leu Arg Leu Leu Val Lys His Ala Gly Glu Leu
    1790                1795                1800

Arg Gln Tyr Leu Glu His Gly Leu Glu Thr Thr Pro Thr Ala Pro
    1805                1810                1815

Trp Arg Gly Ile Ile Pro Gln Leu Phe Ser Arg Leu Asn His Pro
    1820                1825                1830

Glu Val Tyr Val Arg Gln Ser Ile Cys Asn Leu Leu Cys Arg Val
    1835                1840                1845

Ala Gln Asp Ser Pro His Leu Ile Leu Tyr Pro Ala Ile Val Gly
    1850                1855                1860

Thr Ile Ser Leu Ser Ser Glu Ser Gln Ala Ser Gly Asn Lys Phe
    1865                1870                1875

Ser Thr Ala Ile Pro Thr Leu Leu Gly Asn Ile Gln Gly Glu Glu
    1880                1885                1890

Leu Leu Val Ser Glu Cys Glu Gly Gly Ser Pro Pro Ala Ser Gln
    1895                1900                1905

Asp Ser Asn Lys Asp Glu Pro Lys Ser Gly Leu Asn Glu Asp Gln
    1910                1915                1920

Ala Met Met Gln Asp Cys Tyr Ser Lys Ile Val Asp Lys Leu Ser
    1925                1930                1935

Ser Ala Asn Pro Thr Met Val Leu Gln Val Gln Met Leu Val Ala
    1940                1945                1950

Glu Leu Arg Arg Val Thr Val Leu Trp Asp Glu Leu Trp Leu Gly
    1955                1960                1965

Val Leu Leu Gln Gln His Met Tyr Val Leu Arg Arg Ile Gln Gln
    1970                1975                1980

Leu Glu Asp Glu Val Lys Arg Val Gln Asn Asn Asn Thr Leu Arg
    1985                1990                1995

Lys Glu Glu Lys Ile Ala Ile Met Arg Glu Lys His Thr Ala Leu
    2000                2005                2010

Met Lys Pro Ile Val Phe Ala Leu Glu His Val Arg Ser Ile Thr
    2015                2020                2025

Ala Ala Pro Ala Glu Thr Pro His Glu Lys Trp Phe Gln Asp Asn
    2030                2035                2040
```

```
Tyr Gly Asp Ala Ile Glu Asn Ala Leu Glu Lys Leu Lys Thr Pro
    2045                2050                2055

Leu Asn Pro Ala Lys Pro Gly Ser Ser Trp Ile Pro Phe Lys Glu
    2060                2065                2070

Ile Met Leu Ser Leu Gln Gln Arg Ala Gln Lys Arg Ala Ser Tyr
    2075                2080                2085

Ile Leu Arg Leu Glu Glu Ile Ser Pro Trp Leu Ala Ala Met Thr
    2090                2095                2100

Asn Thr Glu Ile Ala Leu Pro Gly Glu Val Ser Ala Arg Asp Thr
    2105                2110                2115

Val Thr Ile His Ser Val Gly Gly Thr Ile Thr Ile Leu Pro Thr
    2120                2125                2130

Lys Thr Lys Pro Lys Lys Leu Leu Phe Leu Gly Ser Asp Gly Lys
    2135                2140                2145

Ser Tyr Pro Tyr Leu Phe Lys Gly Leu Glu Asp Leu His Leu Asp
    2150                2155                2160

Glu Arg Ile Met Gln Phe Leu Ser Ile Val Asn Thr Met Phe Ala
    2165                2170                2175

Thr Ile Asn Arg Gln Glu Thr Pro Arg Phe His Ala Arg His Tyr
    2180                2185                2190

Ser Val Thr Pro Leu Gly Thr Arg Ser Gly Leu Ile Gln Trp Val
    2195                2200                2205

Asp Gly Ala Thr Pro Leu Phe Gly Leu Tyr Lys Arg Trp Gln Gln
    2210                2215                2220

Arg Glu Ala Ala Leu Gln Ala Gln Lys Ala Gln Asp Ser Tyr Gln
    2225                2230                2235

Thr Pro Gln Asn Pro Gly Ile Val Pro Arg Pro Ser Glu Leu Tyr
    2240                2245                2250

Tyr Ser Lys Ile Gly Pro Ala Leu Lys Thr Val Gly Leu Ser Leu
    2255                2260                2265

Asp Val Ser Arg Arg Asp Trp Pro Leu His Val Met Lys Ala Val
    2270                2275                2280

Leu Glu Glu Leu Met Glu Ala Thr Pro Pro Asn Leu Leu Ala Lys
    2285                2290                2295

Glu Leu Trp Ser Ser Cys Thr Thr Pro Asp Glu Trp Trp Arg Val
    2300                2305                2310

Thr Gln Ser Tyr Ala Arg Ser Thr Ala Val Met Ser Met Val Gly
    2315                2320                2325

Tyr Ile Ile Gly Leu Gly Asp Arg His Leu Asp Asn Val Leu Ile
    2330                2335                2340

Asp Met Thr Thr Gly Glu Val Val His Ile Asp Tyr Asn Val Cys
    2345                2350                2355

Phe Glu Lys Gly Lys Ser Leu Arg Val Pro Glu Lys Val Pro Phe
    2360                2365                2370

Arg Met Thr Gln Asn Ile Glu Thr Ala Leu Gly Val Thr Gly Val
    2375                2380                2385

Glu Gly Val Phe Arg Leu Ser Cys Glu Gln Val Leu His Ile Met
    2390                2395                2400

Arg Arg Gly Arg Glu Thr Leu Leu Thr Leu Leu Glu Ala Phe Val
    2405                2410                2415

Tyr Asp Pro Leu Val Asp Trp Thr Ala Gly Gly Glu Ala Gly Phe
    2420                2425                2430

Ala Gly Ala Val Tyr Gly Gly Gly Gly Gln Gln Ala Glu Ser Lys
```

```
                2435                2440                2445
Gln Ser Lys Arg Glu Met Glu Arg Glu Ile Thr Arg Ser Leu Phe
    2450                2455                2460
Ser Ser Arg Val Ala Glu Ile Lys Val Asn Trp Phe Lys Asn Arg
    2465                2470                2475
Asp Glu Met Leu Val Val Leu Pro Lys Leu Asp Gly Ser Leu Asp
    2480                2485                2490
Glu Tyr Leu Ser Leu Gln Glu Gln Leu Thr Asp Val Glu Lys Leu
    2495                2500                2505
Gln Gly Lys Leu Leu Glu Glu Ile Glu Phe Leu Glu Gly Ala Glu
    2510                2515                2520
Gly Val Asp His Pro Ser His Thr Leu Gln His Arg Tyr Ser Glu
    2525                2530                2535
His Thr Gln Leu Gln Thr Gln Gln Arg Ala Val Gln Glu Ala Ile
    2540                2545                2550
Gln Val Lys Leu Asn Glu Phe Glu Gln Trp Ile Thr His Tyr Gln
    2555                2560                2565
Ala Ala Phe Asn Asn Leu Glu Ala Thr Gln Leu Ala Ser Leu Leu
    2570                2575                2580
Gln Glu Ile Ser Thr Gln Met Asp Leu Gly Pro Pro Ser Tyr Val
    2585                2590                2595
Pro Ala Thr Ala Phe Leu Gln Asn Ala Gly Gln Ala His Leu Ile
    2600                2605                2610
Ser Gln Cys Glu Gln Leu Glu Gly Glu Val Gly Ala Leu Leu Gln
    2615                2620                2625
Gln Arg Arg Ser Val Leu Arg Gly Cys Leu Glu Gln Leu His His
    2630                2635                2640
Tyr Ala Thr Val Ala Leu Gln Tyr Pro Lys Ala Ile Phe Gln Lys
    2645                2650                2655
His Arg Ile Glu Gln Trp Lys Thr Trp Met Glu Glu Leu Ile Cys
    2660                2665                2670
Asn Thr Thr Val Glu Arg Cys Gln Glu Leu Tyr Arg Lys Tyr Glu
    2675                2680                2685
Met Gln Tyr Ala Pro Gln Pro Pro Thr Val Cys Gln Phe Ile
    2690                2695                2700
Thr Ala Thr Glu Met Thr Leu Gln Arg Tyr Ala Ala Asp Ile Asn
    2705                2710                2715
Ser Arg Leu Ile Arg Gln Val Glu Arg Leu Lys Gln Glu Ala Val
    2720                2725                2730
Thr Val Pro Val Cys Glu Asp Gln Leu Lys Glu Ile Glu Arg Cys
    2735                2740                2745
Ile Lys Val Phe Leu His Glu Asn Gly Glu Glu Gly Ser Leu Ser
    2750                2755                2760
Leu Ala Ser Val Ile Ile Ser Ala Leu Cys Thr Leu Thr Arg Arg
    2765                2770                2775
Asn Leu Met Met Glu Gly Ala Ala Ser Ser Ala Gly Glu Gln Leu
    2780                2785                2790
Val Asp Leu Thr Ser Arg Asp Gly Ala Trp Phe Leu Glu Glu Leu
    2795                2800                2805
Cys Ser Met Ser Gly Asn Val Thr Cys Leu Val Gln Leu Leu Lys
    2810                2815                2820
Gln Cys His Leu Val Pro Gln Asp Leu Asp Ile Pro Asn Pro Met
    2825                2830                2835
```

```
Glu Ala Ser Glu Thr Val His Leu Ala Asn Gly Val Tyr Thr Ser
2840                     2845                2850

Leu Gln Glu Leu Asn Ser Asn Phe Arg Gln Ile Ile Phe Pro Glu
2855                     2860                2865

Ala Leu Arg Cys Leu Met Lys Gly Glu Tyr Thr Leu Glu Ser Met
2870                     2875                2880

Leu His Glu Leu Asp Gly Leu Ile Glu Gln Thr Thr Asp Gly Val
2885                     2890                2895

Pro Leu Gln Thr Leu Val Glu Ser Leu Gln Ala Tyr Leu Arg Asn
2900                     2905                2910

Ala Ala Met Gly Leu Glu Glu Thr His Ala His Tyr Ile Asp
2915                     2920                2925

Val Ala Arg Leu Leu His Ala Gln Tyr Gly Glu Leu Ile Gln Pro
2930                     2935                2940

Arg Asn Gly Ser Val Asp Glu Thr Pro Lys Met Ser Ala Gly Gln
2945                     2950                2955

Met Leu Leu Val Ala Phe Asp Gly Met Phe Ala Gln Val Glu Thr
2960                     2965                2970

Ala Phe Ser Leu Leu Val Glu Lys Leu Asn Lys Met Glu Ile Pro
2975                     2980                2985

Ile Ala Trp Arg Lys Ile Asp Ile Ile Arg Glu Ala Arg Ser Thr
2990                     2995                3000

Gln Val Asn Phe Phe Asp Asp Asn His Arg Gln Val Leu Glu
3005                     3010                3015

Glu Ile Phe Phe Leu Lys Arg Leu Gln Thr Ile Lys Glu Phe Phe
3020                     3025                3030

Arg Leu Cys Gly Thr Phe Ser Lys Thr Leu Ser Gly Ser Ser Ser
3035                     3040                3045

Leu Glu Asp Gln Asn Thr Val Asn Gly Pro Val Gln Ile Val Asn
3050                     3055                3060

Val Lys Thr Leu Phe Arg Asn Ser Cys Phe Ser Glu Asp Gln Met
3065                     3070                3075

Ala Lys Pro Ile Lys Ala Phe Thr Ala Asp Phe Val Arg Gln Leu
3080                     3085                3090

Leu Ile Gly Leu Pro Asn Gln Ala Leu Gly Leu Thr Leu Cys Ser
3095                     3100                3105

Phe Ile Ser Ala Leu Gly Val Asp Ile Ile Ala Gln Val Glu Ala
3110                     3115                3120

Lys Asp Phe Gly Ala Glu Ser Lys Val Ser Val Asp Asp Leu Cys
3125                     3130                3135

Lys Lys Ala Val Glu His Asn Ile Gln Ile Gly Lys Phe Ser Gln
3140                     3145                3150

Leu Val Met Asn Arg Ala Thr Val Leu Ala Ser Ser Tyr Asp Thr
3155                     3160                3165

Ala Trp Lys Lys His Asp Leu Val Arg Arg Leu Glu Thr Ser Ile
3170                     3175                3180

Ser Ser Cys Lys Thr Ser Leu Gln Arg Val Gln Leu His Ile Ala
3185                     3190                3195

Met Phe Gln Trp Gln His Glu Asp Leu Leu Ile Asn Arg Pro Gln
3200                     3205                3210

Ala Met Ser Val Thr Pro Pro Arg Ser Ala Ile Leu Thr Ser
3215                     3220                3225
```

```
Met Lys Lys Lys Leu His Thr Leu Ser Gln Ile Glu Thr Ser Ile
3230                3235                3240
Ala Thr Val Gln Glu Lys Leu Ala Ala Leu Glu Ser Ser Ile Glu
3245                3250                3255
Gln Arg Leu Lys Trp Ala Gly Gly Ala Asn Pro Ala Leu Ala Pro
3260                3265                3270
Val Leu Gln Asp Phe Glu Ala Thr Ile Ala Glu Arg Arg Asn Leu
3275                3280                3285
Val Leu Lys Glu Ser Gln Arg Ala Ser Gln Val Thr Phe Leu Cys
3290                3295                3300
Ser Asn Ile Ile His Phe Glu Ser Leu Arg Thr Arg Thr Ala Glu
3305                3310                3315
Ala Leu Asn Leu Asp Ala Ala Leu Phe Glu Leu Ile Lys Arg Cys
3320                3325                3330
Gln Gln Met Cys Ser Phe Ala Ser Gln Phe Asn Ser Ser Val Ser
3335                3340                3345
Glu Leu Glu Leu Arg Leu Leu Gln Arg Val Asp Thr Gly Leu Glu
3350                3355                3360
His Pro Ile Gly Ser Ser Glu Trp Leu Leu Ser Ala His Lys Gln
3365                3370                3375
Leu Thr Gln Asp Met Ser Thr Gln Arg Ala Ile Gln Thr Glu Lys
3380                3385                3390
Glu Gln Gln Ile Glu Thr Val Cys Glu Thr Ile Gln Asn Leu Val
3395                3400                3405
Asp Asn Ile Lys Thr Val Leu Thr Gly His Asn Arg Gln Leu Gly
3410                3415                3420
Asp Val Lys His Leu Leu Lys Ala Met Ala Lys Asp Glu Glu Ala
3425                3430                3435
Ala Leu Ala Asp Gly Glu Asp Val Pro Tyr Glu Asn Ser Val Arg
3440                3445                3450
Gln Phe Leu Gly Glu Tyr Lys Ser Trp Gln Asp Asn Ile Gln Thr
3455                3460                3465
Val Leu Phe Thr Leu Val Gln Ala Met Gly Gln Val Arg Ser Gln
3470                3475                3480
Glu His Val Glu Met Leu Gln Glu Ile Thr Pro Thr Leu Lys Glu
3485                3490                3495
Leu Lys Thr Gln Ser Gln Ser Ile Tyr Asn Asn Leu Val Ser Phe
3500                3505                3510
Ala Ser Pro Leu Val Thr Asp Ala Thr Asn Glu Cys Ser Ser Pro
3515                3520                3525
Thr Ser Ser Ala Thr Tyr Gln Pro Ser Phe Ala Ala Ala Val Arg
3530                3535                3540
Ser Asn Thr Gly Gln Lys Thr Gln Pro Asp Val Met Ser Gln Asn
3545                3550                3555
Ala Arg Lys Leu Ile Gln Lys Asn Leu Ala Thr Ser Ala Asp Thr
3560                3565                3570
Pro Pro Ser Thr Val Pro Gly Thr Gly Lys Ser Val Ala Cys Ser
3575                3580                3585
Pro Lys Lys Ala Val Arg Asp Pro Lys Thr Gly Lys Ala Val Gln
3590                3595                3600
Glu Arg Asn Ser Tyr Ala Val Ser Val Trp Lys Arg Val Lys Ala
3605                3610                3615
Lys Leu Glu Gly Arg Asp Val Asp Pro Asn Arg Arg Met Ser Val
```

| | | | |
|---|---|---|---|
| Ala Glu | Gln Val Asp Tyr Val | Ile Lys Glu Ala Thr | Asn Leu Asp |
| 3620 | 3625 | 3630 | |
| | 3635 | 3640 | 3645 |

| | | | |
|---|---|---|---|
| Asn Leu | Ala Gln Leu Tyr Glu | Gly Trp Thr Ala Trp | Val |
| 3650 | 3655 | 3660 | |

<210> SEQ ID NO 9
<211> LENGTH: 3051
<212> TYPE: DNA
<213> ORGANISM: Homo sapiens

<400> SEQUENCE: 9

```
atgagccaag gccccccac aggggagagc agcgagcccg aagcaaaagt cctccacact      60
aagcggcttt accgggctgt ggtggaggct gtgcatcgac ttgacctcat cctttgcaac     120
aaaactgctt atcaagaagt attcaaacca gaaaacatta gcctgaggaa caagctgcgt     180
gagctctgcg tcaagcttat gttcctgcac ccagtggact atgggagaaa ggctgaggag     240
ctgctgtgga gaaaggtata ctatgaagtt atccagctta tcaagactaa caaaaagcac     300
atccacagcc ggagcacttt ggaatgtgcc tacaggacgc acctggttgc tggtattggc     360
ttctaccagc atctccttct ctatatccag tcccactacc agctggaact gcagtgctgc     420
atcgactgga cccatgtcac tgacccctc ataggatgca agaagccagt gtctgcctca     480
gggaaggaga tggattgggc acagatggca tgtcaccgat gtctggtgta tctgggggat     540
ttgtcccgat atcagaatga attagctggc gtagataccg agctgctagc cgagagattt     600
tactaccaag ccctgtcagt agctcctcag attggaatgc ccttcaatca gctgggcacc     660
ctggcaggca gcaagtacta taatgtggaa gccatgtatt gctacctgcg ctgcatccag     720
tcagaagtgt cctttgaggg agcctatggg aacctcaagc ggctgtatga caaggcagcc     780
aaaatgtacc accaactgaa gaagtgtgag actcggaaac tgtctcctgg caaaaagcga     840
tgtaaagaca ttaaaaggtt gctagtgaac tttatgtatc tgcaaagcct cctacagccc     900
aaaagcagct ccgtggactc agagctgacc tcactttgcc agtcagtcct ggaggacttc     960
aacctctgcc tcttctacct gcctcctca cccaacctca gctggccag tgaggatgag    1020
gaggagtatg agagtggata tgcttttcctc ccggaccttc tcatctttca aatggtcatc    1080
atctgcctta tgtgtgtgca cagcttggag agagcaggat ccaagcagta cagtgcagcc    1140
attgccttca ccctggccct cttttcccac ctcgtcaatc atgtcaacat acggctgcag    1200
gctgagctgg aagagggcga gaatcccgtc ccggcattcc agagtgatgg cacagatgaa    1260
ccagagtcca aggaacctgt ggagaaagag gaggagccag atcctgagcc tcctcctgta    1320
acaccccaag tgggtgaggg cagaaagagc cgtaagttct ctcgcctctc ctgtctccgc    1380
cgtcgccgcc acccacccaa agttggtgat gacagtgacc tgagtgaagg ctttgaatcg    1440
gactcaagcc atgactcagc ccgggccagt gagggctcag acagtggctc tgacaagagt    1500
cttgaaggtg ggggaacggc ctttgatgct gaaacagact cggaaatgaa tagccaggag    1560
tcccgatcag acttggaaga tatggaggaa gaggagggga cacggtcacc aaccctggag    1620
cccctcgggg gcagatcaga ggctcccgat tccctcaatg cccactggg ccccagtgag    1680
gctagcattg ccagcaatct acaagccatg tccacccaga tgttccagac taagcgctgc    1740
ttccgactgg ccccaccctt tagcaacctg ctcctccagc ccaccaccaa ccctcatacc    1800
tcggccagcc acaggcttg cgtcaatggg gatgtagaca agccttcaga gccagccctct    1860
gaggagggct ctgagtcgga ggggagtgag tccagtggac gctcctgtcg gaatgagcgc    1920
```

```
agcatccagg agaagcttca ggtcctgatg gccgaaggtc tgcttcctgc tgtgaaagtc    1980
ttcctggact ggcttcggac caaccccgac ctcatcatcg tgtgtgcgca gagctctcaa    2040
agtctgtgga accgcctgtc tgtgttgctg aatctgttgc ctgctgctgg tgaactccag    2100
gagtctggcc tggccttgtg tcctgaggtc caagatcttc ttgaaggttg tgaactgcct    2160
gacctcccct ctagccttct gctcccagag gacatggctc ttcgtaacct gccccgctc     2220 cgagctgccc acagacgctt taactttgac acggatcggc ccctgctcag caccttagag    2280
gagtcagtgg tgcgcatctg ctgcatccgc agctttggtc atttcatcgc ccgcctgcaa    2340
ggcagcatcc tgcagttcaa cccagaggtt ggcatcttcg tcagcattgc ccagtctgag    2400
caggagagcc tgctgcagca ggcccaggca cagttccgaa tggcacagga ggaagctcgt    2460
cggaacaggc tcatgagaga catggctcag ctacgacttc agctcgaagt gtctcagctg    2520
gagggcagcc tgcagcagcc caaggcccag tcagccatgt ctccctacct cgtccctgac    2580
acccaggccc tctgccacca tctccctgtc atccgccaac tggccaccag tggccgcttc    2640
attgtcatca tcccaaggac agtgatcgat ggcctggatt tgctgaagaa ggaacaccca    2700
ggggcccggg atgggattcg gtacctggag gcagagttta aaaaggaaa caggtacatt      2760 cgctgccaga agaggtggg aaagagcttt gagcggcata agctgaagag gcaggatgca    2820
gatgcctgga ctctctataa gatcctagac agctgcaaac agctgactct ggcccagggg    2880
gcaggtgagg aggatccgag tggcatggtg accatcatca caggccttcc actggacaac    2940
cccagcgtgc tttcaggccc catgcaggca gccctgcagg ccgctgccca cgccagtgtg    3000
gacatcaaga atgttctgga cttctacaag cagtggaagg aaattggttg a              3051
```

<210> SEQ ID NO 10
<211> LENGTH: 1016
<212> TYPE: PRT
<213> ORGANISM: Homo sapiens

<400> SEQUENCE: 10

```
Met Ser Gln Gly Pro Pro Thr Gly Glu Ser Ser Glu Pro Glu Ala Lys
1               5                   10                  15

Val Leu His Thr Lys Arg Leu Tyr Arg Ala Val Glu Ala Val His
            20                  25                  30

Arg Leu Asp Leu Ile Leu Cys Asn Lys Thr Ala Tyr Gln Glu Val Phe
        35                  40                  45

Lys Pro Glu Asn Ile Ser Leu Arg Asn Lys Leu Arg Glu Leu Cys Val
    50                  55                  60

Lys Leu Met Phe Leu His Pro Val Asp Tyr Gly Arg Lys Ala Glu Glu
65                  70                  75                  80

Leu Leu Trp Arg Lys Val Tyr Tyr Glu Val Ile Gln Leu Ile Lys Thr
                85                  90                  95

Asn Lys Lys His Ile His Ser Arg Ser Thr Leu Glu Cys Ala Tyr Arg
            100                 105                 110

Thr His Leu Val Ala Gly Ile Gly Phe Tyr Gln His Leu Leu Leu Tyr
        115                 120                 125

Ile Gln Ser His Tyr Gln Leu Glu Leu Gln Cys Cys Ile Asp Trp Thr
    130                 135                 140

His Val Thr Asp Pro Leu Ile Gly Cys Lys Lys Pro Val Ser Ala Ser
145                 150                 155                 160

Gly Lys Glu Met Asp Trp Ala Gln Met Ala Cys His Arg Cys Leu Val
                165                 170                 175
```

```
Tyr Leu Gly Asp Leu Ser Arg Tyr Gln Asn Glu Leu Ala Gly Val Asp
            180                 185                 190

Thr Glu Leu Leu Ala Glu Arg Phe Tyr Tyr Gln Ala Leu Ser Val Ala
        195                 200                 205

Pro Gln Ile Gly Met Pro Phe Asn Gln Leu Gly Thr Leu Ala Gly Ser
    210                 215                 220

Lys Tyr Tyr Asn Val Glu Ala Met Tyr Cys Tyr Leu Arg Cys Ile Gln
225                 230                 235                 240

Ser Glu Val Ser Phe Glu Gly Ala Tyr Gly Asn Leu Lys Arg Leu Tyr
                245                 250                 255

Asp Lys Ala Ala Lys Met Tyr His Gln Leu Lys Lys Cys Glu Thr Arg
            260                 265                 270

Lys Leu Ser Pro Gly Lys Lys Arg Cys Lys Asp Ile Lys Arg Leu Leu
        275                 280                 285

Val Asn Phe Met Tyr Leu Gln Ser Leu Leu Gln Pro Lys Ser Ser Ser
    290                 295                 300

Val Asp Ser Glu Leu Thr Ser Leu Cys Gln Ser Val Leu Glu Asp Phe
305                 310                 315                 320

Asn Leu Cys Leu Phe Tyr Leu Pro Ser Ser Pro Asn Leu Ser Leu Ala
                325                 330                 335

Ser Glu Asp Glu Glu Glu Tyr Glu Ser Gly Tyr Ala Phe Leu Pro Asp
            340                 345                 350

Leu Leu Ile Phe Gln Met Val Ile Ile Cys Leu Met Cys Val His Ser
        355                 360                 365

Leu Glu Arg Ala Gly Ser Lys Gln Tyr Ser Ala Ala Ile Ala Phe Thr
    370                 375                 380

Leu Ala Leu Phe Ser His Leu Val Asn His Val Asn Ile Arg Leu Gln
385                 390                 395                 400

Ala Glu Leu Glu Glu Gly Glu Asn Pro Val Pro Ala Phe Gln Ser Asp
                405                 410                 415

Gly Thr Asp Glu Pro Glu Ser Lys Glu Pro Val Glu Lys Glu Glu Glu
            420                 425                 430

Pro Asp Pro Glu Pro Pro Val Thr Pro Gln Val Gly Glu Gly Arg
        435                 440                 445

Lys Ser Arg Lys Phe Ser Arg Leu Ser Cys Leu Arg Arg Arg His
    450                 455                 460

Pro Pro Lys Val Gly Asp Asp Ser Asp Leu Ser Glu Gly Phe Glu Ser
465                 470                 475                 480

Asp Ser Ser His Asp Ser Ala Arg Ala Ser Glu Gly Ser Asp Ser Gly
                485                 490                 495

Ser Asp Lys Ser Leu Glu Gly Gly Thr Ala Phe Asp Ala Glu Thr
            500                 505                 510

Asp Ser Glu Met Asn Ser Gln Glu Ser Arg Ser Asp Leu Glu Asp Met
        515                 520                 525

Glu Glu Glu Glu Gly Thr Arg Ser Pro Thr Leu Glu Pro Pro Arg Gly
    530                 535                 540

Arg Ser Glu Ala Pro Asp Ser Leu Asn Gly Leu Gly Pro Ser Glu
545                 550                 555                 560

Ala Ser Ile Ala Ser Asn Leu Gln Ala Met Ser Thr Gln Met Phe Gln
                565                 570                 575

Thr Lys Arg Cys Phe Arg Leu Ala Pro Thr Phe Ser Asn Leu Leu Leu
            580                 585                 590
```

```
Gln Pro Thr Thr Asn Pro His Thr Ser Ala Ser His Arg Pro Cys Val
            595                 600                 605

Asn Gly Asp Val Asp Lys Pro Ser Glu Pro Ala Ser Glu Glu Gly Ser
        610                 615                 620

Glu Ser Glu Gly Ser Glu Ser Ser Gly Arg Ser Cys Arg Asn Glu Arg
625                 630                 635                 640

Ser Ile Gln Glu Lys Leu Gln Val Leu Met Ala Glu Gly Leu Leu Pro
                645                 650                 655

Ala Val Lys Val Phe Leu Asp Trp Leu Arg Thr Asn Pro Asp Leu Ile
            660                 665                 670

Ile Val Cys Ala Gln Ser Ser Gln Ser Leu Trp Asn Arg Leu Ser Val
        675                 680                 685

Leu Leu Asn Leu Leu Pro Ala Ala Gly Glu Leu Gln Glu Ser Gly Leu
    690                 695                 700

Ala Leu Cys Pro Glu Val Gln Asp Leu Leu Glu Gly Cys Glu Leu Pro
705                 710                 715                 720

Asp Leu Pro Ser Ser Leu Leu Pro Glu Asp Met Ala Leu Arg Asn
                725                 730                 735

Leu Pro Pro Leu Arg Ala Ala His Arg Arg Phe Asn Phe Asp Thr Asp
            740                 745                 750

Arg Pro Leu Leu Ser Thr Leu Glu Glu Ser Val Val Arg Ile Cys Cys
        755                 760                 765

Ile Arg Ser Phe Gly His Phe Ile Ala Arg Leu Gln Gly Ser Ile Leu
    770                 775                 780

Gln Phe Asn Pro Glu Val Gly Ile Phe Val Ser Ile Ala Gln Ser Glu
785                 790                 795                 800

Gln Glu Ser Leu Leu Gln Gln Ala Gln Ala Gln Phe Arg Met Ala Gln
                805                 810                 815

Glu Glu Ala Arg Arg Asn Arg Leu Met Arg Asp Met Ala Gln Leu Arg
            820                 825                 830

Leu Gln Leu Glu Val Ser Gln Leu Glu Gly Ser Leu Gln Gln Pro Lys
        835                 840                 845

Ala Gln Ser Ala Met Ser Pro Tyr Leu Val Pro Asp Thr Gln Ala Leu
    850                 855                 860

Cys His His Leu Pro Val Ile Arg Gln Leu Ala Thr Ser Gly Arg Phe
865                 870                 875                 880

Ile Val Ile Ile Pro Arg Thr Val Ile Asp Gly Leu Asp Leu Leu Lys
                885                 890                 895

Lys Glu His Pro Gly Ala Arg Asp Gly Ile Arg Tyr Leu Glu Ala Glu
            900                 905                 910

Phe Lys Lys Gly Asn Arg Tyr Ile Arg Cys Gln Lys Glu Val Gly Lys
        915                 920                 925

Ser Phe Glu Arg His Lys Leu Lys Arg Gln Asp Ala Asp Ala Trp Thr
    930                 935                 940

Leu Tyr Lys Ile Leu Asp Ser Cys Lys Gln Leu Thr Leu Ala Gln Gly
945                 950                 955                 960

Ala Gly Glu Glu Asp Pro Ser Gly Met Val Thr Ile Ile Thr Gly Leu
                965                 970                 975

Pro Leu Asp Asn Pro Ser Val Leu Ser Gly Pro Met Gln Ala Ala Leu
            980                 985                 990

Gln Ala Ala Ala His Ala Ser Val Asp Ile Lys Asn Val Leu Asp Phe
        995                 1000                1005

Tyr Lys Gln Trp Lys Glu Ile Gly
```

<210> SEQ ID NO 11
<211> LENGTH: 1536
<212> TYPE: DNA
<213> ORGANISM: Homo sapiens

<400> SEQUENCE: 11

| | | | | | |
|---|---|---|---|---|---|
| atggagacat | tccctgcagt | ggctgagaag | gtcctcaagg | agttccaggt | gttactgcag | 60 |
| cacagcccct | ctcccattgg | aagtacccgc | atgctgcagc | ttatgaccat | caatatgttt | 120 |
| gcagtacaca | actcccagct | gaaagactgc | ttctcggagg | agtgccgctc | tgtgatccag | 180 |
| gaacaagccg | cagctctggg | cttggccatg | ttttctctac | tggtccgccg | ctgcacctgc | 240 |
| ttacttaagg | agtccgccaa | agctcagctg | tcctctcctg | aggaccagga | tgaccaagac | 300 |
| gacatcaagg | tgtcttcctt | tgtcccggac | ctgaaggagc | tgctccccag | tgtcaaagtc | 360 |
| tggtcagatt | ggatgctcgg | ctaccccgac | acctggaatc | tcctcccac | atccctggat | 420 |
| ctgccctcgc | atgttgctgt | ggatgtatgg | tcgacgctgg | ctgatttctg | taacatactg | 480 |
| actgcagtga | atcagtctga | ggtgccactg | tacaaggacc | cggatgatga | cctcacccct | 540 |
| cttatcctgg | aagaggatcg | gcttctctcg | ggctttgtcc | ccttgctggc | tgcccctcag | 600 |
| gaccccctgct | acgtggagaa | aacctcggat | aaggttattg | cagctgactg | caaagggtc | 660 |
| acagtgctga | agtattttct | ggaagccctt | tgtggacaag | aagagcctct | gctggcattc | 720 |
| aagggtggaa | agtatgtgtc | agtggcaccc | gtcccagaca | ccatgggaaa | ggaaatggga | 780 |
| agccaagagg | gaacacgact | ggaagatgag | gaggaggatg | tggtgattga | agactttgag | 840 |
| gaagattcag | aggctgaagg | cagcggaggc | gaggatgaca | tcagggagct | tcgggccaag | 900 |
| aagctggctc | tggccaggaa | gatagctgag | cagcagcgtc | gccaggaaaa | gatccaggct | 960 |
| gtcctggagg | accacagtca | gatgaggcag | atggagctcg | aaatcagacc | tttgttcctc | 1020 |
| gtaccagaca | ccaacggctt | cattgaccac | ctggccagtc | tggcgcggct | gctggagagc | 1080 |
| aggaagtaca | tcctggtggt | gcccctcatc | gtgatcaatg | agctggacgg | cctggccaag | 1140 |
| gggcaggaga | cagaccaccg | ggctgggggc | tacgcccgtg | tggtacaaga | gaaggcccgc | 1200 |
| aagtccatcg | agttcctcga | gcagcgattc | gagagtcggg | actcttgcct | gcgagccctg | 1260 |
| accagccgtg | gcaatgaact | cgaatccatc | gccttccgca | gtgaggacat | cactggccag | 1320 |
| ctgggtaaca | acgatgatct | catcctgtcc | tgctgcctcc | actactgcaa | agacaaggct | 1380 |
| aaggacttca | tgcccgccag | caaagaggag | ccaatccggc | tactgcggga | ggtggtgctg | 1440 |
| ttgacggatg | accggaacct | gcgtgtgaag | gcgctcacaa | ggaatgttcc | tgtacgggac | 1500 |
| atcccagcct | tcctcacgtg | ggcccaggtg | ggctga | | | 1536 |

<210> SEQ ID NO 12
<211> LENGTH: 511
<212> TYPE: PRT
<213> ORGANISM: Homo sapiens

<400> SEQUENCE: 12

Met Glu Thr Phe Pro Ala Val Ala Glu Lys Val Leu Lys Glu Phe Gln
1               5                   10                  15

Val Leu Leu Gln His Ser Pro Ser Pro Ile Gly Ser Thr Arg Met Leu
                20                  25                  30

Gln Leu Met Thr Ile Asn Met Phe Ala Val His Asn Ser Gln Leu Lys
            35                  40                  45

```
Asp Cys Phe Ser Glu Glu Cys Arg Ser Val Ile Gln Glu Gln Ala Ala
 50                  55                  60

Ala Leu Gly Leu Ala Met Phe Ser Leu Leu Val Arg Arg Cys Thr Cys
 65                  70                  75                  80

Leu Leu Lys Glu Ser Ala Lys Ala Gln Leu Ser Ser Pro Glu Asp Gln
                 85                  90                  95

Asp Asp Gln Asp Asp Ile Lys Val Ser Ser Phe Val Pro Asp Leu Lys
            100                 105                 110

Glu Leu Leu Pro Ser Val Lys Val Trp Ser Asp Trp Met Leu Gly Tyr
        115                 120                 125

Pro Asp Thr Trp Asn Pro Pro Thr Ser Leu Asp Leu Pro Ser His
130                 135                 140

Val Ala Val Asp Val Trp Ser Thr Leu Ala Asp Phe Cys Asn Ile Leu
145                 150                 155                 160

Thr Ala Val Asn Gln Ser Glu Val Pro Leu Tyr Lys Asp Pro Asp Asp
                165                 170                 175

Asp Leu Thr Leu Leu Ile Leu Glu Glu Asp Arg Leu Leu Ser Gly Phe
            180                 185                 190

Val Pro Leu Leu Ala Ala Pro Gln Asp Pro Cys Tyr Val Glu Lys Thr
        195                 200                 205

Ser Asp Lys Val Ile Ala Ala Asp Cys Lys Arg Val Thr Val Leu Lys
210                 215                 220

Tyr Phe Leu Glu Ala Leu Cys Gly Gln Glu Glu Pro Leu Leu Ala Phe
225                 230                 235                 240

Lys Gly Gly Lys Tyr Val Ser Val Ala Pro Val Pro Asp Thr Met Gly
                245                 250                 255

Lys Glu Met Gly Ser Gln Glu Gly Thr Arg Leu Glu Asp Glu Glu Glu
            260                 265                 270

Asp Val Val Ile Glu Asp Phe Glu Glu Asp Ser Glu Ala Glu Gly Ser
        275                 280                 285

Gly Gly Glu Asp Asp Ile Arg Glu Leu Arg Ala Lys Lys Leu Ala Leu
        290                 295                 300

Ala Arg Lys Ile Ala Glu Gln Gln Arg Arg Gln Glu Lys Ile Gln Ala
305                 310                 315                 320

Val Leu Glu Asp His Ser Gln Met Arg Gln Met Glu Leu Glu Ile Arg
                325                 330                 335

Pro Leu Phe Leu Val Pro Asp Thr Asn Gly Phe Ile Asp His Leu Ala
            340                 345                 350

Ser Leu Ala Arg Leu Leu Glu Ser Arg Lys Tyr Ile Leu Val Val Pro
        355                 360                 365

Leu Ile Val Ile Asn Glu Leu Asp Gly Leu Ala Lys Gly Gln Glu Thr
370                 375                 380

Asp His Arg Ala Gly Gly Tyr Ala Arg Val Val Gln Glu Lys Ala Arg
385                 390                 395                 400

Lys Ser Ile Glu Phe Leu Glu Gln Arg Phe Glu Ser Arg Asp Ser Cys
                405                 410                 415

Leu Arg Ala Leu Thr Ser Arg Gly Asn Glu Leu Glu Ser Ile Ala Phe
            420                 425                 430

Arg Ser Glu Asp Ile Thr Gly Gln Leu Gly Asn Asn Asp Asp Leu Ile
        435                 440                 445

Leu Ser Cys Cys Leu His Tyr Cys Lys Asp Lys Ala Lys Asp Phe Met
450                 455                 460

Pro Ala Ser Lys Glu Glu Pro Ile Arg Leu Leu Arg Glu Val Val Leu
```

```
                465           470            475           480
         Leu Thr Asp Asp Arg Asn Leu Arg Val Lys Ala Leu Thr Arg Asn Val
                      485               490                495

Pro Val Arg Asp Ile Pro Ala Phe Leu Thr Trp Ala Gln Val Gly
                      500               505               510

<210> SEQ ID NO 13
<211> LENGTH: 3537
<212> TYPE: DNA
<213> ORGANISM: Homo sapiens

<400> SEQUENCE: 13
atgagcctgc agagcgcgca gtacctccgg caggcagaag tcctgaaggc tgacatgaca     60
gattctaagc tgggtccagc tgaagtctgg acatccaggc aggctctgca ggacctgtac    120
cagaaaatgc tagttaccga tttggaatac gctttagaca agaaagtaga acaggatctc    180
tggaatcacg cctttaagaa tcagatcaca cactacaag gccaggcaaa gaatcgagca    240
aatccgaatc ggagtgaagt tcaggcaaac ctttctctgt tcctagaggc agctagtggc    300
ttctatactc agttattaca agaactgtgt acagtattta atgtagattt accatgccgt    360
gtgaagtctt cccaattggg aattatcagc aataaacaga cgcataccag cgccatagtg    420
aagccacagt ctagctcctg ttcctatatc tgccagcact gcctcgtcca ccttggagac    480
attgctcgat acagaaacca gaccagccag gcagagtcct actataggca tgcagctcag    540
cttgtcccct ccaatggtca gcttataat cagttggcta tcttagcttc ttccaaagga    600
gaccatctga ccacaatttt ctactactgc agaagcattg ctgtgaagtt ccctttccca    660
gctgcctcca ctaatctgca aaaagcactt tctaaagcac tggaaagccg agatgaggtg    720
aaaaccaagt ggggtgtttc tgacttcatc aaggcctta ttaaattcca cggtcatgtg    780
tacctgagta agagcttgga aaagttgagc cctcttcgag agaaattgga agaacagttt    840
aagaggctgc tattccaaaa agctttcaac tctcagcagt tagttcatgt cactgtcatt    900
aacctgtttc aacttcatca ccttcgtgac tttagcaatg aaaccgagca gcacacttat    960
agccaagatg agcagctatg ttggacacag ttgctggccc tctttatgtc ttttctcggc   1020
atcctgtgca gtgtcctct acagaatgag tctcaggagg agtcctacaa tgcctatcct   1080
cttccagcag tcaaggtctc catggactgg ctaagactca gacccagggt ctttcaggag   1140
gcagtggtgg atgaaagaca gtacatttgg ccctggttga tttctcttct gaatagtttc   1200
catccccatg aagaggacct ctcaagtatt agtgcgacac acttccaga ggagtttgaa   1260 ttacaaggat ttttggcatt gagaccttct ttcaggaact tggattttc caaaggtcac   1320 cagggtatta caggggacaa agaaggccag caacgacgaa tacgacagca acgcttgatc   1380
tctataggca atggattgc tgataatcag ccaaggctga ttcagtgtga aaatgaggta   1440
gggaaattgt tgtttatcac agaaatccca gaattaatac tggaagaccc cagtgaagcc   1500
aaagagaacc tcattctgca agaaacatct gtgatagagt cgctggctgc agatgggagc   1560
ccagggctaa aatcagtgct atctacaagc cgaaatttaa gcaacaactg tgacacagga   1620
gagaagccag tggttacctt caaagaaaac attaagacac gagaagtgaa cagagaccaa   1680
ggaagaagtt ttcctcccaa agaggtaaaa tcccagacag aactaagaaa gactccagtg   1740
tctgaagcca gaaaacacc tgtaactcaa ccccaactc aagcaagtaa ctcccagttc   1800
atccccattc atcaccctgg agccttccct cctcttccca gcaggccagg gtttccgccc   1860
ccaacatatg ttatccccc gcctgtggca ttttctatgg gctcaggtta caccttccca   1920
```

```
gctggtgttt ctgtcccagg aacctttctt cagcctacag ctcactctcc agcaggaaac    1980
caggtgcaag ctgggaaaca gtcccacatt ccttacagcc agcaacggcc ctctggacca    2040
gggccaatga accagggacc tcaacaatca cagccaccct cccagcaacc ccttacatct    2100
ttaccagctc agccaacagc acagtctaca agccagctgc aggttcaagc tctaactcag    2160
caacaacaat ccctacaaa  agctgtgccg gctttgggga aaagcccgcc tcaccactct    2220
ggattccagc agtatcaaca ggcagatgcc tccaaacagc tgtggaatcc ccctcaggtt    2280
caaggcccat tagggaaaat tatgcctgtg aaacagccct actaccttca gacccaagac    2340
cccataaaac tgtttgagcc gtcattgcaa cctcctgtaa tgcagcagca gcctctagaa    2400
aaaaaaatga agccttttcc catggagcca tataaccata atccctcaga agtcaaggtc    2460
ccagaattct actgggattc ttcctacagc atggctgata cagatctgt  aatggcacag    2520 caagcaaaca tagaccgcag gggcaaacgg tcaccaggaa tcttccgtcc agagcaggat    2580
cctgtaccca gaatgccgtt tgaggacccc aagagctccc ctctgcttcc tccggacctg    2640
ttaaagagtc tggctgcctt ggaggaagag gaagagctga ttttttctaa cactcctgat    2700
ctttacccgg ctctgctggg gcctctcgcc tctcttcctg gacgaagcct ttttaaatcc    2760
ttattggaga agccctcaga gctcatgtca cattcatcct ctttcctgtc cctcaccgga    2820
ttctctctca atcaggaaag atacccaaat aatagtatgt tcaatgaggt atatgggaaa    2880
aacctgacat ccagctccaa agcagaactc agtccctcaa tggccccca  ggaaacatct    2940 ctgtattccc tttttgaagg gactccgtgg tctccatcac ttcctgccag ttcagatcat    3000
tcaacaccag ccagccagtc tcctcattcc tctaacccaa gcagcctacc cagctctcct    3060
ccaacacaca accataattc tgttccattc tccaattttg gacccattgg gactccagat    3120
aacagggata gaaggactgc agatcggtgg aaaactgata gccagccat  gggtgggttt    3180 ggcattgatt atctctcagc aacgtcatcc tctgagagca gttggcatca ggccagcact    3240
ccgagtggca cctggacagg ccatggccct tccatggagg attcctctgc tgtcctcatg    3300
gaaagcctaa agaagcaaca gcatggggtc cagcagttgg ggcccaaaag acagtctgaa    3360
gaggaaggaa gcagcagtat ctgcgtagcc cacagagggc ccaggcccct gcccagctgc    3420
agtctcccag cctccacttt cagagtgaaa ttcaaggcag cacggacatg tgcccatcag    3480
gcacagaaga aaacacgacg tcgtccattt tggaagagac gaaagaaagg aaaataa      3537
```

<210> SEQ ID NO 14
<211> LENGTH: 1178
<212> TYPE: PRT
<213> ORGANISM: Homo sapiens

<400> SEQUENCE: 14

```
Met Ser Leu Gln Ser Ala Gln Tyr Leu Arg Gln Ala Glu Val Leu Lys
1               5                   10                  15

Ala Asp Met Thr Asp Ser Lys Leu Gly Pro Ala Glu Val Trp Thr Ser
            20                  25                  30

Arg Gln Ala Leu Gln Asp Leu Tyr Gln Lys Met Leu Val Thr Asp Leu
        35                  40                  45

Glu Tyr Ala Leu Asp Lys Lys Val Glu Gln Asp Leu Trp Asn His Ala
    50                  55                  60

Phe Lys Asn Gln Ile Thr Thr Leu Gln Gly Gln Ala Lys Asn Arg Ala
65                  70                  75                  80

Asn Pro Asn Arg Ser Glu Val Gln Ala Asn Leu Ser Leu Phe Leu Glu
```

```
                 85                  90                  95
Ala Ala Ser Gly Phe Tyr Thr Gln Leu Leu Gln Glu Leu Cys Thr Val
                100                 105                 110

Phe Asn Val Asp Leu Pro Cys Arg Val Lys Ser Ser Gln Leu Gly Ile
                115                 120                 125

Ile Ser Asn Lys Gln Thr His Thr Ser Ala Ile Val Lys Pro Gln Ser
                130                 135                 140

Ser Ser Cys Ser Tyr Ile Cys Gln His Cys Leu Val His Leu Gly Asp
145                 150                 155                 160

Ile Ala Arg Tyr Arg Asn Gln Thr Ser Gln Ala Glu Ser Tyr Tyr Arg
                165                 170                 175

His Ala Ala Gln Leu Val Pro Ser Asn Gly Gln Pro Tyr Asn Gln Leu
                180                 185                 190

Ala Ile Leu Ala Ser Ser Lys Gly Asp His Leu Thr Thr Ile Phe Tyr
                195                 200                 205

Tyr Cys Arg Ser Ile Ala Val Lys Phe Pro Phe Pro Ala Ala Ser Thr
                210                 215                 220

Asn Leu Gln Lys Ala Leu Ser Lys Ala Leu Glu Ser Arg Asp Glu Val
225                 230                 235                 240

Lys Thr Lys Trp Gly Val Ser Asp Phe Ile Lys Ala Phe Ile Lys Phe
                245                 250                 255

His Gly His Val Tyr Leu Ser Lys Ser Leu Glu Lys Leu Ser Pro Leu
                260                 265                 270

Arg Glu Lys Leu Glu Glu Gln Phe Lys Arg Leu Leu Phe Gln Lys Ala
                275                 280                 285

Phe Asn Ser Gln Gln Leu Val His Val Thr Val Ile Asn Leu Phe Gln
                290                 295                 300

Leu His His Leu Arg Asp Phe Ser Asn Glu Thr Glu Gln His Thr Tyr
305                 310                 315                 320

Ser Gln Asp Glu Gln Leu Cys Trp Thr Gln Leu Leu Ala Leu Phe Met
                325                 330                 335

Ser Phe Leu Gly Ile Leu Cys Lys Cys Pro Leu Gln Asn Glu Ser Gln
                340                 345                 350

Glu Glu Ser Tyr Asn Ala Tyr Pro Leu Pro Ala Val Lys Val Ser Met
                355                 360                 365

Asp Trp Leu Arg Leu Arg Pro Arg Val Phe Gln Glu Ala Val Val Asp
                370                 375                 380

Glu Arg Gln Tyr Ile Trp Pro Trp Leu Ile Ser Leu Leu Asn Ser Phe
385                 390                 395                 400

His Pro His Glu Glu Asp Leu Ser Ser Ile Ser Ala Thr Pro Leu Pro
                405                 410                 415

Glu Glu Phe Glu Leu Gln Gly Phe Leu Ala Leu Arg Pro Ser Phe Arg
                420                 425                 430

Asn Leu Asp Phe Ser Lys Gly His Gln Gly Ile Thr Gly Asp Lys Glu
                435                 440                 445

Gly Gln Gln Arg Arg Ile Arg Gln Arg Leu Ile Ser Ile Gly Lys
                450                 455                 460

Trp Ile Ala Asp Asn Gln Pro Arg Leu Ile Gln Cys Glu Asn Glu Val
465                 470                 475                 480

Gly Lys Leu Leu Phe Ile Thr Glu Ile Pro Glu Leu Ile Leu Glu Asp
                485                 490                 495

Pro Ser Glu Ala Lys Glu Asn Leu Ile Leu Gln Glu Thr Ser Val Ile
                500                 505                 510
```

```
Glu Ser Leu Ala Ala Asp Gly Ser Pro Gly Leu Lys Ser Val Leu Ser
            515                 520                 525

Thr Ser Arg Asn Leu Ser Asn Asn Cys Asp Thr Gly Glu Lys Pro Val
    530                 535                 540

Val Thr Phe Lys Glu Asn Ile Lys Thr Arg Glu Val Asn Arg Asp Gln
545                 550                 555                 560

Gly Arg Ser Phe Pro Pro Lys Glu Val Lys Ser Gln Thr Glu Leu Arg
                565                 570                 575

Lys Thr Pro Val Ser Glu Ala Arg Lys Thr Pro Val Thr Gln Thr Pro
            580                 585                 590

Thr Gln Ala Ser Asn Ser Gln Phe Ile Pro Ile His His Pro Gly Ala
        595                 600                 605

Phe Pro Pro Leu Pro Ser Arg Pro Gly Phe Pro Pro Thr Tyr Val
            610                 615                 620

Ile Pro Pro Pro Val Ala Phe Ser Met Gly Ser Gly Tyr Thr Phe Pro
625                 630                 635                 640

Ala Gly Val Ser Val Pro Gly Thr Phe Leu Gln Pro Thr Ala His Ser
                645                 650                 655

Pro Ala Gly Asn Gln Val Gln Ala Gly Lys Gln Ser His Ile Pro Tyr
                660                 665                 670

Ser Gln Gln Arg Pro Ser Gly Pro Gly Pro Met Asn Gln Gly Pro Gln
        675                 680                 685

Gln Ser Gln Pro Pro Ser Gln Gln Pro Leu Thr Ser Leu Pro Ala Gln
    690                 695                 700

Pro Thr Ala Gln Ser Thr Ser Gln Leu Gln Val Gln Ala Leu Thr Gln
705                 710                 715                 720

Gln Gln Gln Ser Pro Thr Lys Ala Val Pro Ala Leu Gly Lys Ser Pro
                725                 730                 735

Pro His His Ser Gly Phe Gln Gln Tyr Gln Gln Ala Asp Ala Ser Lys
            740                 745                 750

Gln Leu Trp Asn Pro Pro Gln Val Gln Gly Pro Leu Gly Lys Ile Met
        755                 760                 765

Pro Val Lys Gln Pro Tyr Tyr Leu Gln Thr Gln Asp Pro Ile Lys Leu
    770                 775                 780

Phe Glu Pro Ser Leu Gln Pro Val Met Gln Gln Pro Leu Glu
785                 790                 795                 800

Lys Lys Met Lys Pro Phe Pro Met Glu Pro Tyr Asn His Asn Pro Ser
                805                 810                 815

Glu Val Lys Val Pro Glu Phe Tyr Trp Asp Ser Ser Tyr Ser Met Ala
            820                 825                 830

Asp Asn Arg Ser Val Met Ala Gln Gln Ala Asn Ile Asp Arg Arg Gly
        835                 840                 845

Lys Arg Ser Pro Gly Ile Phe Arg Pro Glu Gln Asp Pro Val Pro Arg
    850                 855                 860

Met Pro Phe Glu Asp Pro Lys Ser Ser Pro Leu Leu Pro Pro Asp Leu
865                 870                 875                 880

Leu Lys Ser Leu Ala Ala Leu Glu Glu Glu Glu Leu Ile Phe Ser
                885                 890                 895

Asn Thr Pro Asp Leu Tyr Pro Ala Leu Leu Gly Pro Leu Ala Ser Leu
            900                 905                 910

Pro Gly Arg Ser Leu Phe Lys Ser Leu Leu Glu Lys Pro Ser Glu Leu
        915                 920                 925
```

-continued

```
Met Ser His Ser Ser Ser Phe Leu Ser Leu Thr Gly Phe Ser Leu Asn
    930             935             940

Gln Glu Arg Tyr Pro Asn Asn Ser Met Phe Asn Glu Val Tyr Gly Lys
945             950             955             960

Asn Leu Thr Ser Ser Ser Lys Ala Glu Leu Ser Pro Ser Met Ala Pro
            965             970             975

Gln Glu Thr Ser Leu Tyr Ser Leu Phe Glu Gly Thr Pro Trp Ser Pro
        980             985             990

Ser Leu Pro Ala Ser Ser Asp His Ser Thr Pro Ala Ser Gln Ser Pro
        995             1000            1005

His Ser Ser Asn Pro Ser Ser Leu Pro Ser Ser Pro Pro Thr His
    1010            1015            1020

Asn His Asn Ser Val Pro Phe Ser Asn Phe Gly Pro Ile Gly Thr
    1025            1030            1035

Pro Asp Asn Arg Asp Arg Arg Thr Ala Asp Arg Trp Lys Thr Asp
    1040            1045            1050

Lys Pro Ala Met Gly Gly Phe Gly Ile Asp Tyr Leu Ser Ala Thr
    1055            1060            1065

Ser Ser Ser Glu Ser Ser Trp His Gln Ala Ser Thr Pro Ser Gly
    1070            1075            1080

Thr Trp Thr Gly His Gly Pro Ser Met Glu Asp Ser Ser Ala Val
    1085            1090            1095

Leu Met Glu Ser Leu Lys Lys Gln Gln His Gly Val Gln Gln Leu
    1100            1105            1110

Gly Pro Lys Arg Gln Ser Glu Glu Glu Gly Ser Ser Ser Ile Cys
    1115            1120            1125

Val Ala His Arg Gly Pro Arg Pro Leu Pro Ser Cys Ser Leu Pro
    1130            1135            1140

Ala Ser Thr Phe Arg Val Lys Phe Lys Ala Ala Arg Thr Cys Ala
    1145            1150            1155

His Gln Ala Gln Lys Lys Thr Arg Arg Arg Pro Phe Trp Lys Arg
    1160            1165            1170

Arg Lys Lys Gly Lys
    1175
```